United States Patent
Bebernitz et al.

(10) Patent No.: US 8,394,772 B2
(45) Date of Patent: Mar. 12, 2013

(54) GLYCOSIDE DERIVATIVE AND USES THEREOF

(75) Inventors: Gregory Raymond Bebernitz, Stow, MA (US); Mark Gary Bock, Boston, MA (US); Debnath Bhuniya, Howrah (IN); Laxmikant Datrange, Bangalore (IN); Suresh Eknath Kurhade, Pune (IN); P. Venkata Palle, Pune (IN); Dumbala Srinivas Reddy, Hyderabad (IN)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/395,139

(22) PCT Filed: Oct. 20, 2010

(86) PCT No.: PCT/EP2010/065802
§ 371 (c)(1),
(2), (4) Date: Mar. 9, 2012

(87) PCT Pub. No.: WO2011/048148
PCT Pub. Date: Apr. 28, 2011

(65) Prior Publication Data
US 2012/0196813 A1    Aug. 2, 2012

(30) Foreign Application Priority Data
Oct. 20, 2009  (IN) ................ 2172/DEL/09

(51) Int. Cl.
*A01N 43/04* (2006.01)
*A61K 31/70* (2006.01)
*C07H 1/00* (2006.01)

(52) U.S. Cl. ................ 514/23; 536/1.11

(58) Field of Classification Search ............ None
See application file for complete search history.

(56) References Cited

FOREIGN PATENT DOCUMENTS

| | | |
|---|---|---|
| EP | 1 609 785 A1 | 12/2005 |
| EP | 1 731 494 A1 | 12/2006 |
| EP | 2 048 150 A1 | 4/2009 |
| WO | 97/19084 A1 | 5/1997 |
| WO | 01/27128 A1 | 4/2001 |
| WO | 2004/089927 A1 | 10/2004 |
| WO | 2008/013322 A1 | 1/2008 |
| WO | 2008/101939 A1 | 8/2008 |

OTHER PUBLICATIONS

Koh et al., Circulation, 2008; 117: 3238-3249.*
Adachi et al., Metabolism, vol. 49, No. 8, 2000, 990-995.*
Huber et al.; "Synthesis of Potential Glucosidase-Inhibitors: D-Xylopyranoside-5-spiro-1'-cyclopropanes"; Helvetica Chimica Acta; 73(5):1329-1337 (1990).
Mascitti et al.; "Syntheses of C-5-spirocyclic C-glycoside SGLT2 inhibitors"; Tetrahedron Letters; 51 (14):1880-1883 (2010).
Robinson et al.; "C-Aryl glycoside inhibitors of SGLT2: Exploration of sugar modifications including C-5 spirocyclization"; Bioorganic & Medicinal Chemistry Letters; 20(5):1569-1572 (2010).

* cited by examiner

*Primary Examiner* — Traviss C McIntosh, III
(74) *Attorney, Agent, or Firm* — Joshua Roth

(57) ABSTRACT

This invention relates to compounds represented by formula (I):

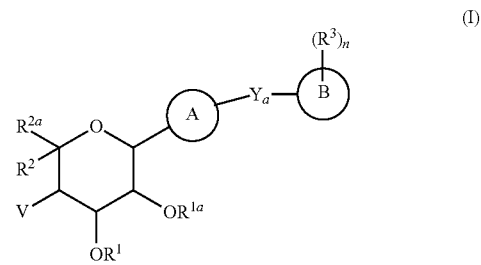

wherein the variables are defined as herein above, which are useful for treating diseases and conditions mediated by the sodium D-glucose co-transporter (SGLT), e.g. diabetes. The invention also provides methods of treating such diseases and conditions, and compositions etc. for their treatment.

18 Claims, No Drawings

GLYCOSIDE DERIVATIVE AND USES THEREOF

This application is a U.S. National Phase filing of International Serial No. PCT/EP2010/065802 filed Oct. 20, 2010, and claims priority to Indian Application Serial No. 2172/DEL/09 filed Oct. 20, 2009, the contents of which are incorporated herein by reference in their entirety.

BACKGROUND OF THE INVENTION

Diabetes mellitus is a metabolic disorder characterized by recurrent or persistent hyperglycemia (high blood glucose) and other signs, as distinct from a single disease or condition. Glucose level abnormalities can result in serious long-term complications, which include cardiovascular disease, chronic renal failure, retinal damage, nerve damage (of several kinds), microvascular damage and obesity.

Type 1 diabetes, also known as Insulin Dependent Diabetes Mellitus (IDDM), is characterized by loss of the insulin-producing β-cells of the islets of Langerhans of the pancreas leading to a deficiency of insulin. Type-2 diabetes previously known as adult-onset diabetes, maturity-onset diabetes, or Non-Insulin Dependent Diabetes Mellitus (NIDDM)—is due to a combination of increased hepatic glucose output, defective insulin secretion, and insulin resistance or reduced insulin sensitivity (defective responsiveness of tissues to insulin).

Chronic hyperglycemia can also lead to onset or progression of glucose toxicity characterized by decrease in insulin secretion from β-cell, insulin sensitivity; as a result diabetes mellitus is self-exacerbated [*Diabetes Care,* 1990, 13, 610].

Chronic elevation of blood glucose level also leads to damage of blood vessels. In diabetes, the resultant problems are grouped under "microvascular disease" (due to damage of small blood vessels) and "macrovascular disease" (due to damage of the arteries). Examples of microvascular disease include diabetic retinopathy, neuropathy and nephropathy, while examples of macrovascular disease include coronary artery disease, stroke, peripheral vascular disease, and diabetic myonecrosis.

Diabetic retinopathy, characterized by the growth of weakened blood vessels in the retina as well as macular edema (swelling of the macula), can lead to severe vision loss or blindness. Retinal damage (from microangiopathy) makes it the most common cause of blindness among non-elderly adults in the US. Diabetic neuropathy is characterized by compromised nerve function in the lower extremities. When combined with damaged blood vessels, diabetic neuropathy can lead to diabetic foot. Other forms of diabetic neuropathy may present as mononeuritis or autonomic neuropathy. Diabetic nephropathy is characterized by damage to the kidney, which can lead to chronic renal failure, eventually requiring dialysis. Diabetes mellitus is the most common cause of adult kidney failure worldwide. A high glycemic diet (i.e., a diet that consists of meals that give high postprandial blood sugar) is known to be one of the causative factors contributing to the development of obesity.

Type 2 diabetes is characterized by insulin resistance and/or inadequate insulin secretion in response to elevated glucose level. Therapies for type 2 diabetes are targeted towards increasing insulin sensitivity (such as TZDs), hepatic glucose utilization (such as biguanides), directly modifying insulin levels (such as insulin, insulin analogs, and insulin secretagogues), increasing incretin hormone action (such as exenatide and sitagliptin), or inhibiting glucose absorption from the diet (such as alpha glucosidase inhibitors) [*Nature* 2001, 414, 821-827].

Glucose is unable to diffuse across the cell membrane and requires transport proteins. The transport of glucose into epithelial cells is mediated by a secondary active cotransport system, the sodium-D-glucose co-transporter (SGLT), driven by a sodium-gradient generated by the Na+/K+-ATPase. Glucose accumulated in the epithelial cell is further transported into the blood across the membrane by facilitated diffusion through GLUT transporters [*Kidney International* 2007, 72, S27-S35].

SGLT belongs to the sodium/glucose co-transporter family SLCA5. Two different SGLT isoforms, SGLT1 and SGLT2, have been identified to mediate renal tubular glucose reabsorption in humans [*Curr. Opinion in Investigational Drugs* (2007): 8(4), 285-292 and references cited herein]. Both of them are characterized by their different substrate affinity. Although both of them show 59% homology in their amino acid sequence, they are functionally different. SGLT1 transports glucose as well as galactose, and is expressed both in the kidney and in the intestine, while SGLT2 is found exclusively in the S1 and S2 segments of the renal proximal tubule. As a consequence, glucose filtered in the glomerulus is reabsorbed into the renal proximal tubular epithelial cells by SGLT2, a low-affinity/high-capacity system, residing on the surface of epithelial cell lining in S1 and S2 tubular segments. Much smaller amounts of glucose are recovered by SGLT1, as a high-affinity/low-capacity system, on the more distal segment of the proximal tubule. In healthy human, more than 99% of plasma glucose that is filtered in the kidney glomerulus is reabsorbed, resulting in less than 1% of the total filtered glucose being excreted in urine. It is estimated that 90% of total renal glucose absorption is facilitated by SGLT2; remaining 10% is likely mediated by SGLT1 [*J. Parenter. Enteral Nutr.* 2004, 28, 364-371].

SGLT2 was cloned as a candidate sodium glucose co-transporter, and its tissue distribution, substrate specificity, and affinities are reportedly very similar to those of the low-affinity sodium glucose co-transporter in the renal proximal tubule. A drug with a mode of action of SGLT2 inhibition will be a novel and complementary approach to existing classes of medication for diabetes and its associated diseases to meet the patient's needs for both blood glucose control, while preserving insulin secretion. In addition, SGLT2 inhibitors which lead to loss of excess glucose (and thereby excess calories) may have additional potential for the treatment of obesity.

Indeed small molecule SGLT2 inhibitors have been discovered and the anti-diabetic therapeutic potential of such molecules has been reported in literature [T-1095 (Diabetes, 1999, 48, 1794-1800, Dapagliflozin (Diabetes, 2008, 57, 1723-1729)].

Various O-aryl and O-heteroaryl glycosides have been reported as SGLT-2 inhibitors in patent publications such as: WO 01/74834, WO 03/020737, US04/0018998, WO 01/68660, WO 01/16147, WO 04/099230, WO 05/011592, U.S. Ser. No. 06/0,293,252 and WO 05/021566.

Various glucopyranosyl-substituted aromatic and heteroaromatic compounds have also been reported as SGLT-2 inhibitors in patent publications such as: WO 01/27128, WO 04/080990, U.S. Ser. No. 06/0,025,349, WO 05/085265, WO 05/085237, WO 06/054629 and WO 06/011502.

SGLT1 is predominantly found in the intestine and plays a major role in the absorption of D-glucose and D-galactose. Therefore, SGLT1 inhibitors have the potential to act both in the kidney as well as the intestine to reduce calorie intake and hyperglycemia.

WO2004/018491 discloses pyrazole derivatives which are SGLT1 inhibitors.

Glucopyranosyl-substituted aromatic or heteroaromatic compounds where, in general, the sugar moiety has been modified at C4, C5, or C6 positions of pyranose have been published (U.S. Ser. No. 06/0,009,400, U.S. Ser. No. 06/0,019,948, U.S. Ser. No. 06/0,035,841, U.S. Ser. No. 06/0,074,031, U.S. Ser. No. 08/0,027,014 and WO 08/016,132).

DETAILED DESCRIPTION OF THE INVENTION

This invention relates to compounds useful for treating diseases and conditions mediated by the sodium D-glucose co-transporter (SGLT), e.g. diabetes. The invention also provides methods of treating such diseases and conditions, and compounds and compositions etc. for their treatment.

The invention provides novel glycoside derivatives, their polymorphs, stereoisomers, pro-drugs, solvates, pharmaceutically acceptable salts and formulations thereof. The invention also relates to processes for the preparation of the compounds of the invention.

The compounds of the invention possess sodium-D-glucose co-transporter (SGLT) inhibition effects, which are beneficial for the prophylaxis, management, treatment, control of progression, or adjunct treatment of diseases and/or medical conditions where the inhibition of SGLT would be beneficial, such as diabetes (including Type-I and Type-II), obesity, dyslipidemia, insulin resistance, and other metabolic syndrome, and/or diabetes-related complications including retinopathy, nephropathy, neuropathy, ischemic heart disease, arteriosclerosis, β-cell dysfunction, and as therapeutic and/or prophylactic agents for obesity.

The inventors have found compounds of Formula (I) that are useful for inhibiting SGLT. Accordingly, in a first aspect of the invention, there is provided a compound of Formula (I):

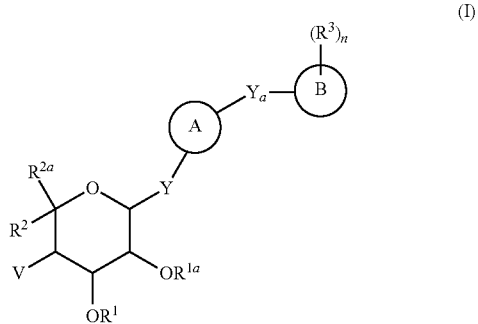

(I)

Ring A is an $C_{6-10}$aryl or a 5- to 10-membered heteroaryl; wherein the aryl or heteroaryl is optionally substituted with one or more substituents independently selected from the group consisting of a halo, hydroxy, cyano, $C_{1-6}$alkyl, $C_{3-7}$cycloalkyl, $C_{2-6}$alkenyl, $C_{2-6}$alkynyl, $C_{1-6}$alkoxy, halo$C_{1-6}$alkoxy, a 5-membered heteroaryl and a 6-membered heteroaryl;

Ring B is a $C_{6-10}$aryl or a $C_{1-10}$heteroaryl;

Y is a direct bond or O;

$Y_a$ is a bond or a $(C_1-C_6)$alkylene which is optionally substituted with one or more substituents independently selected from halo, $C_{1-4}$alkyl, halo$C_{1-4}$alkyl;

V is hydrogen, halo or —$OR^{1b}$;

$R^1$, $R^{1a}$, and $R^{1b}$ are independently selected from hydrogen, $C_{1-6}$ alkyl, $C_{6-10}$aryl-$C_{1-4}$alkyl, —$C(O)C_{6-10}$aryl or —$C(O)C_{1-6}$alkyl;

$R^2$ and $R^{2a}$ are independently selected from the group consisting of $C_{1-6}$alkyl and $C_{1-6}$alkoxy, wherein the alkyl and the alkoxy may be optionally substituted with one or more substituents which are independently selected from halo, hydroxy, $C_{1-4}$alkyl, and $C_{1-4}$alkoxy; provided that Y is a direct bond when $R^2$ and $R^{2a}$ are an optionally substituted alkyl; or $R^2$ and $R^{2a}$ taken together with the carbon to which they are attached may form a spiro 3- to 7-membered heterocyclyl or a spiro $C_{3-7}$cycloalkyl which may be optionally substituted with one or more substituents independently selected from halo, hydroxy, oxo, $C_{1-4}$alkyl, hydroxy$C_{1-4}$ alkyl, $C_{1-4}$alkoxy, $C_{1-4}$alkoxy$C_{1-4}$alkyl, halo$C_{1-4}$alkyl, $C_{1-6}$alkanoyl, carbamoyl, N—($C_{1-4}$alkyl)-carbamoyl, and N,N-di-($C_{1-4}$alkyl)-carbamoyl; and $R^3$, for each occurrence, is independently selected from the group consisting of halo, hydroxy, cyano, nitro, oxo, $C_{1-6}$alkyl, $C_{3-7}$cycloalkyl, $C_{3-7}$cycloalkyl$C_{1-4}$alkyl, $C_{1-10}$aryl, $C_{6-10}$aryl$C_{1-4}$alkyl, —$C(O)OR^6$, —$C(O)R^6$, —$C(O)NR^4R^5$, —$NR^4R^5$, —$CH_2NR^4R^5$, $C_{1-6}$ alkoxy, $C_{3-7}$ cycloalkoxy, —$S(O)_pR^6$, —$S(O)_2NR^4R^5$, —$OS(O)_2R^6$, —$CH_2C(O)OR^6$, —$CH_2C(O)NR^4R^5$, —$NR^6C(O)NR^4R^5$, —$NR^6C(O)OR^6$, $C_{6-10}$aryloxy, $C_{2-10}$heterocyclyl, $C_{2-10}$heterocyclyl$C_{1-4}$alkyl, $C_{1-10}$heteroaryl$C_{1-4}$alkyl, $C_{1-10}$heteroaryl, $C_{1-10}$heteroaryloxy, or $C_{1-10}$heterocycloxy; wherein $R^3$ may, for each occurrence, be optionally substituted with one or more substituents which are independently selected from halo, hydroxy, $C_{1-4}$alkyl, and $C_{1-4}$alkoxy;

$R^6$, for each occurrence, is independently selected from hydrogen, $C_{1-6}$ alkyl, $C_{3-7}$ cycloalkyl, $C_{3-7}$cycloalkyl$C_{1-4}$ alkyl, $C_{6-10}$aryl, $C_{1-10}$heteroaryl, and $C_{2-10}$heterocyclyl;

$R^4$ and $R^5$, for each occurrence, are independently selected from hydrogen, $C_{1-6}$ alkyl, $C_{3-7}$ cycloalkyl, $C_{3-7}$ cycloalkyl$C_{1-4}$alkyl, $C_{6-70}$aryl$C_{1-4}$alkyl, $C_{6-10}$aryl, $C_{1-10}$heteroaryl, $C_{1-10}$heteroaryl$C_{1-4}$alkyl, $C_{2-10}$heterocyclyl, and $C_{2-10}$heterocyclyl$C_{1-4}$alkyl; or $R^4$ and $R^5$ taken together along with the nitrogen to which they are bound may form a monocyclic or a bicyclic heteroaryl or heterocyclyl which may be optionally substituted with one or more halo or $C_{1-4}$alkyl;

n is 0, 1, 2, 3, or 4;

or a pharmaceutically acceptable salt thereof.

In a second aspect of the invention, the compound of Formula (I) is of Formula (I-i):

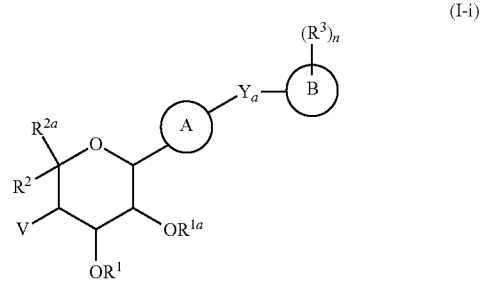

(I-i)

Ring A is an $C_{6-10}$aryl or a 5- to 10-membered heteroaryl; wherein the aryl or heteroaryl is optionally substituted with one or more substituents independently selected from the group consisting of a halo, hydroxy, cyano, $C_{1-6}$alkyl, $C_{3-7}$cycloalkyl, $C_{2-6}$alkenyl, $C_{2-6}$alkynyl, $C_{1-6}$alkoxy, halo$C_{1-6}$alkoxy, a 5-membered heteroaryl and a 6-membered heteroaryl;

Ring B is a $C_{6-10}$aryl or a $C_{1-10}$heteroaryl;

$Y_a$ is a bond or a $C_{1-3}$alkylene;

V is hydrogen, halo or —$OR^{1b}$;

$R^1$, $R^{1a}$, and $R^{1b}$ are independently selected from hydrogen, $C_{1-6}$ alkyl, $C_{6-10}$aryl-$C_{1-4}$alkyl, —$C(O)C_{6-10}$aryl or —$C(O)C_{1-6}$alkyl;

$R^2$ and $R^{2a}$ are independently selected from the group consisting of $C_{1-3}$alkyl and $C_{1-3}$alkoxy, wherein the alkyl and the alkoxy may be optionally substituted with one or more substituents which are independently selected from hydroxy, $C_{1-3}$alkyl, and $C_{1-3}$alkoxy; or $R^2$ and $R^{2a}$ taken together with the carbon to which they are attached may form a spiro 3- to 7-membered heterocyclyl or a spiro $C_{3-7}$cycloalkyl which may be optionally substituted with one or more substituents independently selected from halo, hydroxy, oxo, $C_{1-4}$alkyl, hydroxy$C_{1-4}$ alkyl, $C_{1-4}$alkoxy, $C_{1-4}$alkoxy$C_{1-4}$alkyl, halo$C_{1-4}$alkyl, $C_{1-6}$alkanoyl, carbamoyl, N—($C_{1-4}$alkyl)-carbamoyl, and N,N-di-($C_{1-4}$alkyl)-carbamoyl; and $R^3$, for each occurrence, is independently selected from the group consisting of halo, hydroxy, cyano, nitro, oxo, $C_{1-6}$alkyl, $C_{3-7}$cycloalkyl, $C_{3-7}$cycloalkyl$C_{1-4}$alkyl, $C_{6-10}$aryl, $C_{6-10}$aryl$C_{1-4}$alkyl, —$C(O)OR^6$, —$C(O)R^6$, —$C(O)NR^4R^6$, —$NR^4R^5$, —$CH_2NR^4R^5$, $C_{1-6}$ alkoxy, $C_{3-7}$ cycloalkoxy, —$S(O)_pR^6$, —$S(O)_2NR^4R^5$, —$OS(O)_2R^6$, —$CH_2C(O)OR^6$, —$CH_2C(O)NR^4R^5$, —$NR^6C(O)NR^4R^5$, —$NR^6C(O)OR^6$, $C_{6-10}$aryloxy, $C_{2-10}$heterocyclyl, $C_{2-10}$heterocyclyl$C_{1-4}$alkyl, $C_{1-10}$heteroaryl$C_{1-4}$alkyl, $C_{1-10}$heteroaryl, $C_{1-10}$heteroaryloxy, or $C_{1-10}$heterocycloxy; wherein $R^3$ may, for each occurrence, be optionally substituted with one or more substituents which are independently selected from halo, hydroxy, $C_{1-4}$alkyl, and $C_{1-4}$alkoxy;

$R^6$, for each occurrence, is independently selected from hydrogen, $C_{1-6}$ alkyl, $C_{3-7}$ cycloalkyl, $C_{3-7}$cycloalkyl$C_{1-4}$ alkyl, $C_{6-10}$aryl, $C_{1-10}$heteroaryl, and $C_{2-10}$heterocyclyl;

$R^4$ and $R^5$, for each occurrence, are independently selected from hydrogen, $C_{1-6}$ alkyl, $C_{3-7}$ cycloalkyl, $C_{3-7}$ cycloalkyl$C_{1-4}$alkyl, $C_{6-10}$aryl$C_{1-4}$alkyl, $C_{6-10}$aryl, $C_{1-10}$heteroaryl, $C_{1-10}$heteroaryl$C_{1-4}$alkyl, $C_{2-10}$heterocyclyl, and $C_{2-10}$heterocyclyl$C_{1-4}$alkyl; or $R^4$ and $R^5$ taken together along with the nitrogen to which they are bound may form a monocyclic or a bicyclic heteroaryl or heterocyclyl which may be optionally substituted with one or more halo or $C_{1-4}$alkyl;

n is 0, 1, 2, 3, or 4;

or a pharmaceutically acceptable salt thereof.

In a third aspect of the invention, the compound of Formula (I) is of Formula (I-ii):

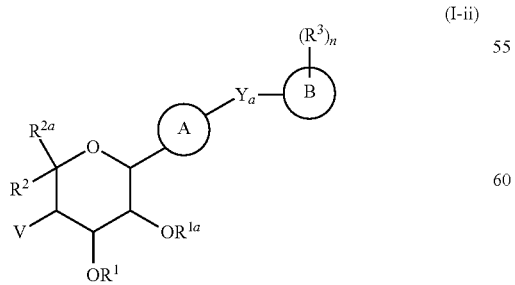

(I-ii)

Ring A is an $C_{6-10}$aryl or a 5- to 10-membered heteroaryl; wherein the aryl or heteroaryl is optionally substituted with one or more substituents independently selected from the group consisting of a halo, hydroxy, cyano, $C_{1-6}$alkyl, $C_{3-7}$cycloalkyl, $C_{2-6}$alkenyl, $C_{2-6}$alkynyl, $C_{1-6}$alkoxy, halo$C_{1-6}$alkyl, a 5-membered heteroaryl and a 6-membered heteroaryl;

Ring B is

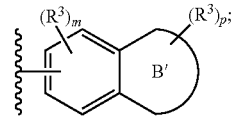

Ring B' is a 5- or 6-membered heterocycyl;

m is 0, 1, 2, 3, or 4;

p is 0, 1, 2, 3, or 4, provided that m+p is not greater than 4;

$Y_a$ is a bond or a $C_{1-3}$alkylene;

V is hydrogen, halo or —$OR^{1b}$;

$R^1$, $R^{1a}$, and $R^{1b}$ are independently selected from hydrogen, $C_{1-6}$ alkyl, $C_{6-10}$aryl-$C_{1-4}$alkyl, —$C(O)C_{6-10}$aryl or —$C(O)C_{1-6}$alkyl;

$R^2$ and $R^{2a}$ are independently selected from the group consisting of $C_{1-6}$alkyl and $C_{1-6}$alkoxy, wherein the alkyl and the alkoxy may be optionally substituted with one or more substituents which are independently selected from halo, hydroxy, $C_{1-4}$alkyl, and $C_{1-4}$alkoxy; or $R^2$ and $R^{2a}$ taken together with the carbon to which they are attached may form a spiro 4- to 6-membered heterocyclyl or a spiro $C_{3-5}$cycloalkyl which may be optionally substituted with one or more substituents independently selected from oxo, $C_{1-2}$alkyl, hydroxy$C_{1-2}$alkyl, $C_{1-2}$alkoxy$C_{1-2}$alkyl, $C_{1-3}$alkanoyl, carbamoyl, N—($C_{1-2}$alkyl)-carbamoyl, and N,N-di-($C_{1-2}$alkyl)-carbamoyl; and $R^3$, for each occurrence, is independently selected from the group consisting of halo, hydroxy, cyano, nitro, oxo, $C_{1-6}$alkyl, $C_{3-7}$cycloalkyl, $C_{3-7}$cycloalkyl$C_{1-4}$alkyl, $C_{6-10}$aryl, $C_{6-10}$aryl$C_{1-4}$alkyl, —$C(O)OR^6$, —$C(O)R^6$, —$C(O)NR^4R^5$, —$NR^4R^5$, —$CH_2NR^4R^5$, $C_{1-6}$ alkoxy, $C_{3-7}$ cycloalkoxy, —$S(O)_pR^6$, —$S(O)_2NR^4R^5$, —$OS(O)_2R^6$, —$CH_2C(O)OR^6$, —$CH_2C(O)NR^4R^6$, —$NR^6C(O)NR^4R^5$, —$NR^6C(O)OR^6$, $C_{6-10}$aryloxy, $C_{2-10}$heterocyclyl, $C_{2-10}$heterocyclyl$C_{1-4}$alkyl, $C_{1-10}$heteroaryl$C_{1-4}$alkyl, $C_{1-10}$heteroaryl, $C_{1-10}$heteroaryloxy, or $C_{1-10}$heterocycloxy; wherein $R^3$ may, for each occurrence, be optionally substituted with one or more substituents which are independently selected from halo, hydroxy, $C_{1-4}$alkyl, and $C_{1-4}$alkoxy;

$R^6$, for each occurrence, is independently selected from hydrogen, $C_{1-6}$ alkyl, $C_{3-7}$ cycloalkyl, $C_{3-7}$cycloalkyl$C_{1-4}$alkyl, $C_{6-10}$aryl, $C_{1-10}$heteroaryl, and $C_{2-10}$heterocyclyl;

$R^4$ and $R^5$, for each occurrence, are independently selected from hydrogen, $C_{1-6}$ alkyl, $C_{3-7}$ cycloalkyl, $C_{3-7}$ cycloalkyl$C_{1-4}$alkyl, $C_{6-10}$aryl$C_{1-4}$alkyl, $C_{6-10}$aryl, $C_{1-10}$heteroaryl, $C_{1-10}$heteroaryl$C_{1-4}$alkyl, $C_{2-10}$heterocyclyl, and $C_{2-10}$heterocyclyl$C_{1-4}$alkyl; or $R^4$ and $R^5$ taken together along with the nitrogen to which they are bound may form a monocyclic or a bicyclic heteroaryl or heterocyclyl which may be optionally substituted with one or more halo or $C_{1-4}$alkyl;

n is 0, 1, 2, 3, or 4;

or a pharmaceutically acceptable salt thereof.

In a fourth aspect of the invention, the compound of Formula (I) is of Formula (I-iii):

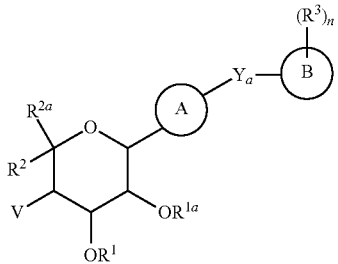

(I-iii)

Ring A is indolyl, thiophenyl, benzothiophenyl or $C_{6-10}$aryl; wherein the indolyl, thiophenyl, benzothiophenyl or $C_{6-10}$aryl may be optionally substituted with one or more substituents which are independently selected from halo, hydroxy, cyano, $C_{1-6}$alkyl, $C_{3-7}$cycloalkyl, $C_{2-6}$alkenyl, $C_{2-6}$alkynyl, $C_{1-6}$alkoxy, halo$C_{1-6}$alkoxy, a 5-membered heteroaryl and a 6-membered heteroaryl;

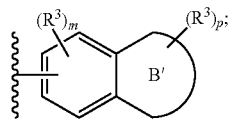

Ring B' is a 5- or 6-membered heterocycyl;
m is 0, 1, 2, 3, or 4;
p is 0, 1, 2, 3, or 4, provided that m+p is not greater than 4;
$Y_a$ is a bond or a $C_{1-3}$alkylene;
V is H, F or OH;
$R^1$ and $R^{1a}$ are both hydrogen;
$R^2$ and $R^{2a}$ are independently selected from the group consisting of $C_{1-6}$alkyl and $C_{1-6}$alkoxy, wherein the alkyl and the alkoxy may be optionally substituted with one or more substituents which are independently selected from halo, hydroxy, $C_{1-4}$alkyl, and $C_{1-4}$alkoxy; or
$R^2$ and $R^{2a}$ taken together with the carbon to which they are attached may form a spiro 4- to 6-membered heterocyclyl or a spiro $C_{3-5}$cycloalkyl which may be optionally substituted with one or more substituents independently selected from oxo, $C_{1-2}$alkyl, hydroxy$C_{1-2}$alkyl, $C_{1-2}$alkoxy$C_{1-2}$alkyl, $C_{1-3}$alkanoyl, carbamoyl, N—($C_{1-2}$alkyl)-carbamoyl, and N,N-di-($C_{1-2}$alkyl)-carbamoyl; and
$R^3$, for each occurrence, is independently selected from the group consisting of hydroxy, oxo, $C_{1-6}$alkyl, $C_{3-7}$cycloalkyl, $C_{6-10}$aryl, —C(O)OR$^6$, —C(O)R$^6$, $C_{1-6}$alkoxy and $C_{1-10}$heterocycloxy; wherein $R^3$ may, for each occurrence, be optionally substituted with one or more substituents which are independently selected from halo, hydroxy, $C_{1-4}$alkyl, and $C_{1-4}$alkoxy;
$R^6$, for each occurrence, is independently selected from hydrogen, $C_{1-3}$ alkyl, $C_{3-7}$ cycloalkyl, $C_{3-7}$cycloalkyl$C_{1-3}$ alkyl, $C_{6-10}$aryl, $C_{1-6}$heteroaryl, and $C_{2-6}$heterocyclyl;
n is 0, 1 or 2;
or a pharmaceutically acceptable salt thereof.

In a fifth aspect of the invention, the compound of Formula (I) is of Formula (I-iv):

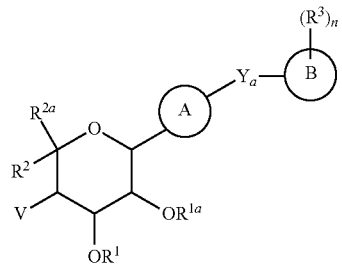

(I-iv)

Ring A is an $C_{6-10}$aryl or a 5- to 10-membered heteroaryl; wherein the aryl or heteroaryl is optionally substituted with one or more substituents independently selected from the group consisting of a halo, hydroxy, cyano, $C_{1-6}$alkyl, $C_{3-7}$cycloalkyl, $C_{2-6}$alkenyl, $C_{2-6}$alkynyl, $C_{1-6}$alkoxy, halo$C_{1-6}$alkoxy, a 5-membered heteroaryl and a 6-membered heteroaryl;
Ring B is a monocyclic $C_{6-10}$aryl or a $C_{1-10}$heteroaryl;
$Y_a$ is a bond or a $C_{1-3}$alkylene;
V is hydrogen, halo or —OR$^{1b}$;
$R^1$, $R^{1a}$, and $R^{1b}$ are independently selected from hydrogen, $C_{1-6}$ alkyl, $C_{6-10}$aryl-$C_{1-4}$alkyl, —C(O)$C_{6-10}$aryl or —C(O)$C_{1-6}$alkyl;
$R^2$ and $R^{2a}$ are independently selected from the group consisting of $C_{1-6}$alkyl and $C_{1-6}$alkoxy, wherein the alkyl and the alkoxy may be optionally substituted with one or more substituents which are independently selected from halo, hydroxy, $C_{1-4}$alkyl, and $C_{1-4}$alkoxy; or
$R^2$ and $R^{2a}$ taken together with the carbon to which they are attached may form a spiro 4- to 6-membered heterocyclyl or a spiro $C_{3-5}$cycloalkyl which may be optionally substituted with one or more substituents independently selected from oxo, $C_{1-2}$alkyl, hydroxy$C_{1-2}$alkyl, $C_{1-2}$alkoxy$C_{1-2}$alkyl, $C_{1-3}$alkanoyl, carbamoyl, N—($C_{1-2}$alkyl)-carbamoyl, and N,N-di-($C_{1-2}$alkyl)-carbamoyl; and
$R^3$, for each occurrence, is independently selected from the group consisting of halo, hydroxy, cyano, nitro, oxo, $C_{1-6}$alkyl, $C_{3-7}$cycloalkyl, $C_{3-7}$cycloalkyl$C_{1-4}$alkyl, $C_{6-10}$aryl, $C_{6-10}$aryl$C_{1-4}$alkyl, —C(O)OR$^6$, —C(O)R$^6$, —C(O)NR$^4$R$^5$, —NR$^4$R$^5$, —CH$_2$NR$^4$R$^5$, $C_{1-6}$ alkoxy, $C_{3-7}$ cycloalkoxy, —S(O)$_p$R$^6$, —S(O)$_2$NR$^4$R$^5$, —OS(O)$_2$R$^8$, —CH$_2$C(O)OR$^6$, —CH$_2$C(O)NR$^4$R$^5$, —NR$^6$C(O)NR$^4$R$^5$, —NR$^6$C(O)OR$^6$, $C_{6-10}$aryloxy, $C_{2-10}$heterocyclyl, $C_{2-10}$heterocyclyl$C_{1-4}$alkyl, $C_{1-10}$heteroaryl$C_{1-4}$alkyl, $C_{1-10}$heteroaryl, $C_{1-10}$heteroaryloxy, or $C_{1-10}$heterocycloxy; wherein $R^3$ may, for each occurrence, be optionally substituted with one or more substituents which are independently selected from halo, hydroxy, $C_{1-4}$alkyl, and $C_{1-4}$alkoxy;
$R^6$, for each occurrence, is independently selected from hydrogen, $C_{1-6}$ alkyl, $C_{3-7}$ cycloalkyl, $C_{3-7}$ cycloalkyl$C_{1-4}$alkyl, $C_{6-10}$aryl, $C_{1-10}$heteroaryl, and $C_{2-10}$heterocyclyl;
$R^4$ and $R^5$, for each occurrence, are independently selected from hydrogen, $C_{1-6}$ alkyl, $C_{3-7}$ cycloalkyl, $C_{3-7}$ cycloalkyl$C_{1-4}$alkyl, $C_{6-10}$aryl$C_{1-4}$alkyl, $C_{6-10}$aryl, $C_{1-10}$heteroaryl, $C_{1-10}$heteroaryl$C_{1-4}$alkyl, $C_{2-10}$heterocyclyl, and $C_{2-10}$heterocyclyl$C_{1-4}$alkyl; or
$R^4$ and $R^5$ taken together along with the nitrogen to which they are bound may form a monocyclic or a bicyclic heteroaryl or heterocyclyl which may be optionally substituted with one or more halo or $C_{1-4}$alkyl;
n is 0, 1, 2, 3, or 4;
or a pharmaceutically acceptable salt thereof.

In a sixth aspect of the invention, the compound of Formula (I) is of Formula (I-v):

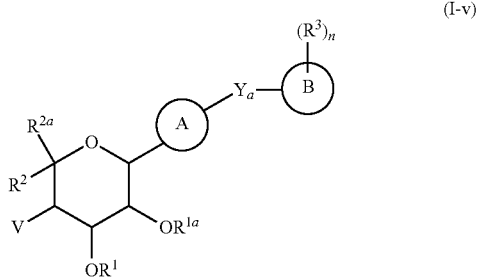

(I-v)

Ring A is indolyl, thiophenyl, benzothiophenyl or $C_{6\text{-}10}$aryl; wherein the indolyl, thiophenyl, benzothiophenyl or $C_{6\text{-}10}$aryl may be optionally substituted with one or more substituents which are independently selected from halo, hydroxy, cyano, $C_{1\text{-}6}$alkyl, $C_{3\text{-}7}$cycloalkyl, $C_{2\text{-}6}$alkenyl, $C_{2\text{-}6}$alkynyl, $C_{1\text{-}6}$alkoxy, halo$C_{1\text{-}6}$alkoxy, a 5-membered heteroaryl and a 6-membered heteroaryl;

Ring B is a monocyclic $C_{6\text{-}10}$aryl or a $C_{1\text{-}10}$heteroaryl;

$Y_a$ is a bond or a $C_{1\text{-}3}$alkylene;

V is H, F or OH;

$R^1$ and $R^{1a}$ are both hydrogen;

$R^2$ and $R^{2a}$ are independently selected from the group consisting of $C_{1\text{-}6}$alkyl and $C_{1\text{-}6}$alkoxy, wherein the alkyl and the alkoxy may be optionally substituted with one or more substituents which are independently selected from halo, hydroxy, $C_{1\text{-}4}$alkyl, and $C_{1\text{-}4}$alkoxy; or $R^2$ and $R^{2a}$ taken together with the carbon to which they are attached may form a spiro 4- to 6-membered heterocyclyl or a spiro $C_{3\text{-}5}$cycloalkyl which may be optionally substituted with one or more substituents independently selected from oxo, $C_{1\text{-}2}$alkyl, hydroxy$C_{1\text{-}2}$alkyl, $C_{1\text{-}2}$alkoxy$C_{1\text{-}2}$alkyl, $C_{1\text{-}3}$alkanoyl, carbamoyl, N—($C_{1\text{-}2}$alkyl)-carbamoyl, and N,N-di-($C_{1\text{-}2}$alkyl)-carbamoyl; and $R^3$, for each occurrence, is independently selected from the group consisting of hydroxy, oxo, $C_{1\text{-}6}$alkyl, $C_{3\text{-}7}$cycloalkyl, $C_{6\text{-}10}$aryl, —C(O)O$R^6$, —C(O)$R^6$, $C_{1\text{-}6}$alkoxy and $C_{1\text{-}4}$heterocycloxy; wherein $R^3$ may, for each occurrence, be optionally substituted with one or more substituents which are independently selected from halo, hydroxy, $C_{1\text{-}4}$alkyl, and $C_{1\text{-}4}$alkoxy;

$R^6$, for each occurrence, is independently selected from hydrogen, $C_{1\text{-}3}$ alkyl, $C_{3\text{-}7}$ cycloalkyl, $C_{3\text{-}7}$cycloalkyl$C_{1\text{-}3}$alkyl, $C_{6\text{-}10}$aryl, $C_{1\text{-}6}$heteroaryl, and $C_{2\text{-}6}$heterocyclyl;

n is 0, 1 or 2;

or a pharmaceutically acceptable salt thereof.

In a seventh aspect of the invention, the compound of Formula (I) is of Formula (I-yl):

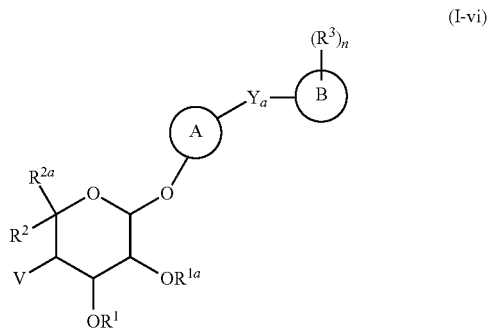

(I-vi)

Ring A is an $C_{6\text{-}10}$aryl or a 5- to 10-membered heteroaryl; wherein the aryl or heteroaryl is optionally substituted with one or more substituents independently selected from the group consisting of a halo, hydroxy, cyano, $C_{3\text{-}7}$cycloalkyl, $C_{2\text{-}6}$alkenyl, $C_{2\text{-}6}$alkynyl, $C_{1\text{-}6}$alkoxy, halo$C_{1\text{-}6}$alkoxy, a 5-membered heteroaryl and a 6-membered heteroaryl;

Ring B is a $C_{6\text{-}10}$aryl or a $C_{1\text{-}10}$heteroaryl;

$Y_a$ is a bond or a $(C_1\text{-}C_6)$alkylene which is optionally substituted with one or more substituents independently selected from halo, $C_{1\text{-}4}$alkyl, halo$C_{1\text{-}4}$alkyl;

V is hydrogen, halo or —O$R^{16}$;

$R^1$, $R^{1a}$, and $R^{1b}$ are independently selected from hydrogen, $C_{1\text{-}6}$ alkyl, $C_{6\text{-}10}$aryl-$C_{1\text{-}4}$alkyl, —C(O)$C_{6\text{-}10}$aryl or —C(O)$C_{1\text{-}6}$alkyl;

one of $R^2$ or $R^{2a}$ is a $C_{1\text{-}6}$alkyl and the other is an $C_{1\text{-}6}$alkoxy, wherein the alkyl and the alkoxy may be optionally substituted with one or more substituents which are independently selected from halo, hydroxy, $C_{1\text{-}4}$alkyl, and $C_{1\text{-}4}$alkoxy; or $R^2$ and $R^{2a}$ taken together with the carbon to which they are attached may form a spiro 3- to 7-membered heterocyclyl or a spiro $C_{3\text{-}7}$cycloalkyl which may be optionally substituted with one or more substituents independently selected from halo, hydroxy, oxo, $C_{1\text{-}4}$alkyl, hydroxy$C_{1\text{-}4}$ alkyl, $C_{1\text{-}4}$alkoxy, $C_{1\text{-}4}$alkoxy$C_{1\text{-}4}$alkyl, halo$C_{1\text{-}4}$alkyl, $C_{1\text{-}6}$alkanoyl, carbamoyl, N—($C_{1\text{-}4}$alkyl)-carbamoyl, and N,N-di-($C_{1\text{-}4}$alkyl)-carbamoyl; and $R^3$, for each occurrence, is independently selected from the group consisting of halo, hydroxy, cyano, nitro, oxo, $C_{1\text{-}6}$alkyl, $C_{3\text{-}7}$cycloalkyl, $C_{3\text{-}7}$cycloalkyl$C_{1\text{-}4}$alkyl, $C_{6\text{-}10}$aryl, $C_{6\text{-}10}$arylC1 alkyl, —C(O)O$R^6$, —C(O)$R^6$, —C(O)N$R^4R^5$, —N$R^4R^5$, —CH$_2$N$R^4R^5$, $C_{1\text{-}6}$ alkoxy, $C_{3\text{-}7}$ cycloalkoxy, —S(O)$_pR^6$, —S(O)$_2$N$R^4R^5$, —OS(O)$_2R^6$, —CH$_2$C(O)O$R^6$, —CH$_2$C(O)N$R^4R^5$, —N$R^6$C(O)N$R^4R^5$, —N$R^8$C(O)O$R^6$, $C_{6\text{-}10}$aryloxy, $C_{2\text{-}10}$heterocycyl, $C_{2\text{-}10}$heterocyclyl$C_1$alkyl, $C_{1\text{-}10}$heteroaryl$C_{1\text{-}4}$ alkyl, $C_{1\text{-}10}$heteroaryl, $C_{1\text{-}10}$heteroaryloxy, or $C_{1\text{-}10}$heterocycloxy; wherein $R^3$ may, for each occurrence, be optionally substituted with one or more substituents which are independently selected from halo, hydroxy, $C_{1\text{-}4}$alkyl, and $C_{1\text{-}4}$alkoxy;

$R^6$, for each occurrence, is independently selected from hydrogen, $C_{1\text{-}6}$ alkyl, $C_{3\text{-}7}$ cycloalkyl, $C_{3\text{-}7}$ cycloalkyl$C_{1\text{-}4}$alkyl, $C_{6\text{-}10}$aryl, $C_{1\text{-}10}$heteroaryl, and $C_{2\text{-}10}$heterocyclyl;

$R^4$ and $R^5$, for each occurrence, are independently selected from hydrogen, $C_{1\text{-}6}$ alkyl, $C_{3\text{-}7}$ cycloalkyl, $C_{3\text{-}7}$ cycloalkyl$C_{1\text{-}4}$alkyl, $C_{6\text{-}10}$aryl$C_{1\text{-}4}$alkyl, $C_{6\text{-}10}$aryl, $C_{1\text{-}10}$heteroaryl, $C_{1\text{-}10}$heteroaryl$C_{1\text{-}4}$alkyl, $C_{2\text{-}10}$heterocyclyl, and $C_{2\text{-}10}$heterocyclyl$C_1$alkyl; or $R^4$ and $R^5$ taken together along with the nitrogen to which they are bound may form a monocyclic or a bicyclic heteroaryl or heterocyclyl which may be optionally substituted with one or more halo or $C_{1\text{-}4}$alkyl;

n is 0, 1, 2, 3, or 4;

or a pharmaceutically acceptable salt thereof.

Embodiments of the compounds of Formulae (I), (I-i), (I-ii), (I-iii), (I-iv) and (I-v)

General

Various embodiments of the invention are described herein. It will be recognised that features specified in each embodiment may be combined with other specified features to provide further embodiments. Thus, combinations of the various features are herein implicitly disclosed.

The tetrahydropyran ring and its substituents $R^2$ and $R^{2a}$

In one embodiment, $R^2$ and $R^{2a}$ are independently selected from the group consisting of $C_{1-3}$alkyl and $C_{1-3}$alkoxy, wherein the alkyl and the alkoxy may be optionally substituted with one or more substituents which are independently selected from hydroxy, $C_{1-3}$alkyl, and $C_{1-3}$alkoxy; or $R^2$ and $R^{2a}$ taken together with the carbon to which they are attached may form a spiro 3- to 7-membered heterocyclyl or a spiro $C_{3-7}$cycloalkyl which may be optionally substituted with one or more substituents independently selected from halo, hydroxy, oxo, $C_{1-4}$alkyl, hydroxy$C_{1-4}$alkyl, $C_{1-4}$alkoxy, $C_{1-4}$alkoxy$C_{1-4}$alkyl, halo$C_{1-4}$alkyl, $C_{1-6}$alkanoyl, carbamoyl, N—($C_{1-4}$alkyl)-carbamoyl, and N,N-di-($C_{1-4}$alkyl)-carbamoyl.

in a further embodiment, $R^2$ and $R^{2a}$ are independently selected from the group consisting of $C_{1-5}$alkyl and $C_{1-6}$alkoxy, wherein the alkyl and the alkoxy may be optionally substituted with one or more substituents which are independently selected from halo, hydroxy, $C_{1-4}$alkyl, and $C_{1-4}$alkoxy; or $R^2$ and $R^{2a}$ taken together with the carbon to which they are attached may form a spiro 4- to 6-membered heterocyclyl or a spiro $C_{3-5}$cycloalkyl which may be optionally substituted with one or more substituents independently selected from oxo, $C_{1-2}$alkyl, hydroxy$C_{1-2}$alkyl, $C_{1-2}$alkoxy$C_{1-2}$alkyl, $C_{1-3}$alkanoyl, carbamoyl, N—($C_{1-2}$alkyl)-carbamoyl, and N,N-di-($C_{1-2}$alkyl)-carbamoyl.

In a further embodiment, $R^2$ and $R^{2a}$ are independently selected from the group consisting of $C_{1-3}$alkyl and $C_{1-3}$alkoxy, wherein the alkyl and the alkoxy may be optionally substituted with one or more substituents which are independently selected from hydroxy, $C_{1-3}$alkyl, and $C_{1-3}$alkoxy; or $R^2$ and $R^{2a}$ taken together with the carbon to which they are attached may form a spiro 4- to 6-membered heterocyclyl or a spiro $C_{3-5}$cycloalkyl which may be optionally substituted with one or more substituents independently selected from oxo, $C_{1-2}$alkyl, hydroxy$C_{1-2}$alkyl, $C_{1-2}$alkoxy$C_{1-2}$alkyl, $C_{1-3}$alkanoyl, carbamoyl, N—($C_{1-2}$alkyl)-carbamoyl, and N,N-di-($C_{1-2}$alkyl)-carbamoyl.

In a further embodiment, $R^2$ and $R^{2a}$ are independently selected from the group consisting of $C_{1-2}$alkyl and $C_{1-2}$alkoxy, wherein the alkyl and the alkoxy may be optionally substituted with one or more substituents which are independently selected from hydroxy, $C_1$alkyl and $C_1$alkoxy; or $R^2$ and $R^{2a}$ taken together with the carbon to which they are attached may form a spiro 4- to 6-membered heterocyclyl or a spiro $C_{3-5}$cycloalkyl which may be optionally substituted with one or more substituents independently selected from oxo, $C_{1-2}$alkyl, hydroxy$C_1$alkyl, $C_1$alkoxy$C_1$alkyl, $C_1$alkanoyl and carbamoyl.

In a further embodiment, one of $R^2$ or $R^{2a}$ is a $C_{1-6}$alkyl and the other is an $C_{1-6}$alkoxy, wherein the alkyl and the alkoxy may be optionally substituted with one or more substituents which are independently selected from halo, hydroxy, $C_{1-4}$alkyl, and $C_{1-4}$alkoxy.

In a further embodiment, when $R^2$ and $R^{2a}$ taken together with the carbon to which they are attached form a substituted spiro moiety, the spiro moiety has 1, 2 or 3 substituents. In a particular embodiment, the spiro moiety has 1 substituent.

In one embodiment, $R^2$ and $R^{2a}$ are selected from one of structures i to xix (wherein the black dot represents the point of attachment to the tetrahydropyran ring):

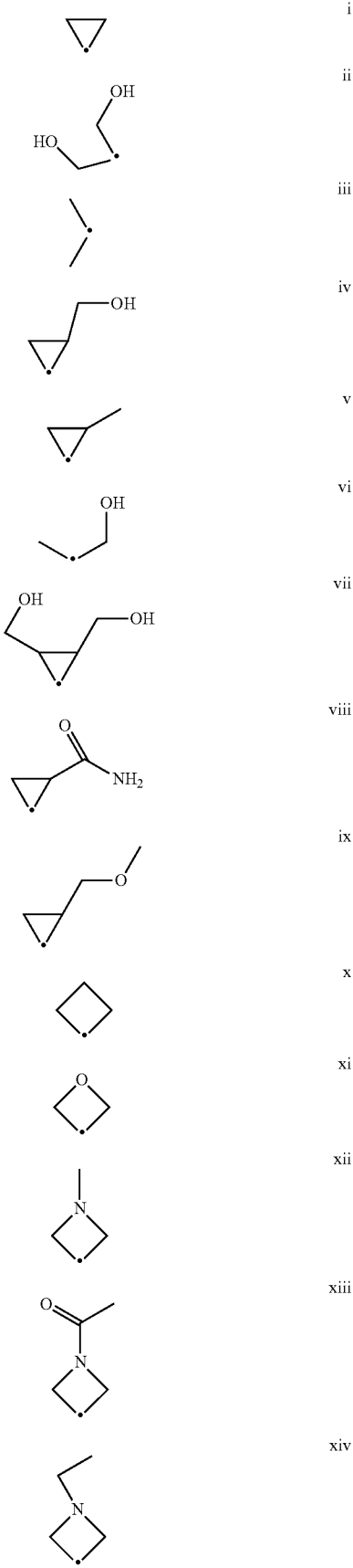

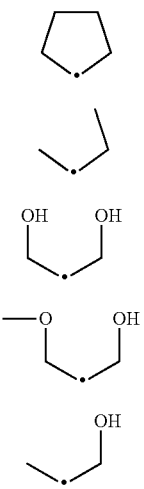

xv xvi xvii xviii xix

In a preferred embodiment, $R^2$ and $R^{2a}$ are selected from one of structures i to iv above.

V

In one embodiment, V is $OR^{1b}$.

In one embodiment, $R^{1b}$ is selected from hydrogen, $C_{1-3}$ alkyl, $C_{6-10}$aryl-$C_{1-4}$alkyl, —C(O)$C_{6-10}$aryl and —C(O)$C_{1-8}$alkyl. In a further embodiment, $R^{1b}$ is H. Thus, in one embodiment, V is OH.

In another embodiment, V is H, F or OH.

$R^1$ and $R^{1a}$

In one embodiment, $R^1$ and $R^{1a}$ are independently selected from hydrogen, $C_{1-3}$ alkyl, $C_{6-10}$aryl-$C_{1-4}$alkyl, —C(O)$C_{6-10}$aryl and —C(O)$C_{1-8}$alkyl. In a further embodiment, $R^1$ is H. In a further embodiment, $R^{1a}$ is H. In a further embodiment, $R^1$ and $R^{1a}$ are both H.

Ring A and its Substituent

In one embodiment, Ring A is substituted with one or more substituents independently selected from the group consisting of halo, hydroxy, $C_{1-3}$alkyl, $C_{2-3}$alkynyl, $C_{1-3}$alkoxy, halo$C_{1-3}$alkoxy and 5-membered heteroaryl. In a further embodiment, Ring A is substituted with one or more substituents independently selected from the group consisting of chloro, fluoro, hydroxy, methyl, methoxy, ethoxy, trifluoromethoxy and N-pyrazolyl. In a further embodiment, Ring A is substituted with one or more substituents independently selected from the group consisting of chloro, fluoro, hydroxyl, cyano, methyl, ethyl, methoxy, ethoxy, trifluoromethoxy and N-pyrazolyl. In a further embodiment, Ring A is substituted with one or more substituents independently selected from the group consisting of chloro, fluoro, methyl, ethyl and methoxy. In a further embodiment, Ring A is substituted with one or more substituents independently selected from chloro and methyl. In a further embodiment, Ring A is substituted with one or more chloro substituents.

In one embodiment, Ring A is a phenyl which is fused to a heterocycle; wherein Ring A may be optionally substituted with one or more substituents which are independently selected from halo, hydroxy, cyano, $C_{1-6}$alkyl, $C_{2-6}$alkenyl, $C_{2-6}$alkynyl, $C_{1-6}$alkoxy, halo$C_{1-6}$alkoxy, a 5-membered heteroaryl and a 6-membered heteroaryl.

In one embodiment, Ring A is indolyl, thiophenyl, benzothiophenyl or $C_{6-10}$aryl; wherein the indolyl, thiophenyl, benzothiophenyl or $C_{6-10}$aryl may be optionally substituted with one or more substituents which are independently selected from halo, hydroxy, cyano, $C_{1-6}$alkyl, $C_{2-6}$alkenyl, $C_{1-6}$alkynyl, $C_{1-6}$alkoxy, halo$C_{1-6}$alkoxy, a 5-membered heteroaryl and a 6-membered heteroaryl.

In one embodiment, Ring A is $C_{6-10}$aryl which is optionally substituted with one or more substituents which are independently selected from halo, hydroxy, cyano, $C_{1-6}$alkyl, $C_{2-6}$alkenyl, $C_{2-6}$alkynyl, $C_{1-6}$alkoxy, halo$C_{1-6}$alkoxy, a 5-membered heteroaryl and a 6-membered heteroaryl. In a further embodiment, Ring A is phenyl which is optionally substituted with one or more substituents which are independently selected from halo, hydroxy, cyano, $C_{1-6}$alkyl, $C_{2-6}$alkenyl, $C_{2-6}$alkynyl, $C_{1-6}$alkoxy, halo$C_{1-6}$alkoxy, a 5-membered heteroaryl and a 6-membered heteroaryl.

In one embodiment, Y is a direct bond.

In one embodiment, Y is O and one of $R^2$ or $R^{2a}$ is a $C_{1-6}$alkyl and the other is an $C_{1-6}$alkoxy, wherein the alkyl and the alkoxy may be optionally substituted with one or more substituents which are independently selected from halo, hydroxy, $C_{1-4}$alkyl, and $C_{1-4}$alkoxy; or $R^2$ and $R^{2a}$ taken together with the carbon to which they are attached may form a spiro 3- to 7-membered heterocyclyl or a spiro $C_{3-7}$cycloalkyl which may be optionally substituted with one or more substituents independently selected from halo, hydroxy, oxo, $C_{1-4}$alkyl, hydroxy$C_{1-4}$alkyl, $C_{1-4}$alkoxy, $C_{1-4}$alkoxy$C_{1-4}$alkyl, halo$C_{1-4}$alkyl, $C_{1-6}$alkanoyl, carbamoyl, N—($C_{1-4}$alkyl)-carbamoyl, and N,N-di-($C_{1-4}$alkyl)-carbamoyl;

In one embodiment, Y is O and one of $R^2$ or $R^{2a}$ is a $C_{1-6}$alkyl and the other is an $C_{1-6}$alkoxy, wherein the alkyl and the alkoxy may be optionally substituted with one or more substituents which are independently selected from halo, hydroxy, $C_{1-4}$alkyl, and $C_{1-4}$alkoxy.

In one embodiment, Y is O and $R^2$ and $R^{2a}$ taken together with the carbon to which they are attached may form a spiro 3- to 7-membered heterocyclyl or a spiro $C_{3-7}$cycloalkyl which may be optionally substituted with one or more substituents independently selected from halo, hydroxy, oxo, $C_{1-4}$alkyl, hydroxy$C_{1-4}$alkyl, $C_{1-4}$alkoxy, $C_{1-4}$alkoxy$C_{1-4}$alkyl, halo$C_{1-4}$alkyl, $C_{1-6}$alkanoyl, carbamoyl, N—($C_{1-4}$alkyl)-carbamoyl, and N,N-di-($C_{1-4}$alkyl)-carbamoyl.

In one embodiment, $Y_a$ is situated meta to the tetrahydropyran ring.

In one embodiment, Ring A has one substituent. In a further embodiment, Ring A is unsubstituted.

In one embodiment, Ring A is phenyl with one substituent, $Y_a$ is situated meta to the tetrahydropyran ring and the one substituent is situated para to the tetrahydropyran ring.

Linker $Y_a$

In one embodiment, $Y_a$ is a bond or a $C_{1-3}$alkylene.

In one embodiment, $Y_a$ is unsubstituted.

In one embodiment, $Y_a$ is $CH_2$.

Ring B

In one embodiment, Ring B is a $C_{6-10}$aryl.

In another embodiment Ring B is a $C_{1-10}$heteroaryl.

Bicyclic Ring B Embodiments

In one embodiment, Ring B is bicyclic. In a further embodiment, Ring B is an azulene ring. In a further embodiment, Ring B is benzothiophene.

In a further embodiment, Ring B has the structure

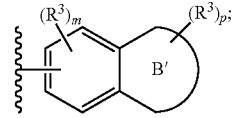

i.e. the compound is represented by Formula (IA):

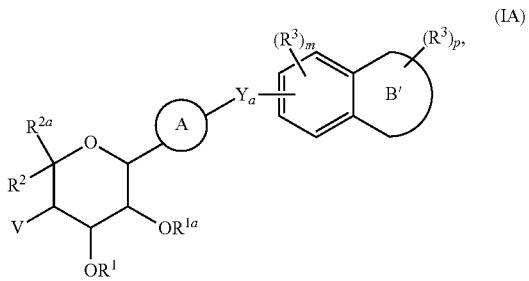

Wherein

V, $R^1$, $R^{1a}$, $R^2$, $R^{2a}$, $R^3$, and $Y_a$ are defined as in Formula (I); and Ring B' is a 5- or 6-membered heterocycyl;

m is 0, 1, 2, 3, or 4; and p is 0, 1, 2, 3, or 4, provided that m+p is not greater than 4; or a pharmaceutically acceptable salt thereof.

In one embodiment, Ring B' contains 1, 2 or 3 heteroatoms.

In one embodiment, Ring B' is selected from the group consisting of a morpholine ring, a piperidine ring, a pyrrolidine ring, a tetrahydropyran ring, a tetrahydrofuran ring, a 1,4-dioxane ring.

In one embodiment, Ring B' contains 2 heteroatoms.

In one embodiment, Ring B' contains at least one O or N heteroatom.

In one embodiment, Ring B' is 1,4-dioxane or morpholine.

Monocyclic Ring B Embodiments

In one embodiment, wherein Ring B is monocyclic. In a further embodiment, Ring B is a 5-, 6-, 7- or 8-membered ring. In a further embodiment, Ring B is a phenyl ring or a thiophene ring.

Substituents on Ring B

In one embodiment, n is 0, 1 or 2 and, if the molecule is such that the m and p labels set out above can be applied, m+p does not exceed the value of n.

In one embodiment, the compound is of Formula (IA) and m is 0 and p is 0, 1 or 2.

In one embodiment, n is 1. Thus, in the embodiment when m is 0, p is necessarily 1.

$R^3$

In one embodiment, $R^3$, for each occurrence, is independently selected from the group consisting of halo, hydroxy, cyano, nitro, oxo, $C_{1-6}$alkyl, $C_{3-7}$cycloalkyl, $C_{6-10}$aryl, $C_{6-10}$aryl$C_{1-4}$alkyl, —C(O)O$R^6$, —C(O)$R^6$, —C(O)N$R^4R^5$, —N$R^4R^5$, —CH$_2$N$R^4R^5$, $C_{1-6}$alkoxy, $C_{3-7}$ cycloalkoxy, —CH$_2$C(O)O$R^6$, —CH$_2$C(O)N$R^4R^5$, —N$R^6$C(O)N$R^4R^5$, —N$R^6$C(O)O$R^6$, $C_{6-10}$aryloxy, $C_{2-10}$heterocyclyl, $C_{1-10}$heteroaryl, $C_{1-10}$heteroaryloxy and $C_{1-10}$heterocycloxy; wherein $R^3$ may, for each occurrence, be optionally substituted with one or more substituents which are independently selected from halo, hydroxy, $C_{1-4}$alkyl, and $C_{1-4}$alkoxy.

In a further embodiment, $R^3$, for each occurrence, is independently selected from the group consisting of hydroxy, oxo, $C_{1-6}$alkyl, $C_{3-7}$cycloalkyl, $C_{6-10}$aryl, —C(O)O$R^6$, —C(O)$R^6$, $C_{1-6}$alkoxy and $C_{1-10}$heterocycloxy; wherein $R^3$ may, for each occurrence, be optionally substituted with one or more substituents which are independently selected from halo, hydroxy, $C_{1-4}$alkyl, and $C_{1-4}$alkoxy.

In a further embodiment, $R^3$, for each occurrence, is independently selected from the group consisting of hydroxy, oxo, $C_{1-3}$alkyl, $C_{3-6}$cycloalkyl, $C_{6-10}$aryl, —C(O)O$R^6$, —C(O)$R^6$, $C_{1-3}$alkoxy and $C_{1-4}$heterocycloxy; wherein $R^3$ may, for each occurrence, be optionally substituted with one or more substituents which are independently selected from halo and $C_{1-3}$alkyl.

$R^6$

In one embodiment, $R^6$, for each occurrence, is independently selected from hydrogen, $C_{1-3}$ alkyl, $C_{3-7}$ cycloalkyl, $C_{3-7}$ cycloalkyl$C_{1-3}$alkyl, $C_{6-10}$aryl, $C_{1-6}$heteroaryl, and $C_{2-6}$heterocyclyl. In a further embodiment, $R^6$ is selected from H and $C_{1-3}$ alkyl.

$R^4$ and $R^5$

In one embodiment, $R^4$ and $R^5$, for each occurrence, are independently selected from hydrogen, $C_{1-3}$ alkyl, $C_{3-7}$ cycloalkyl, $C_{3-7}$ cycloalkyl$C_{1-3}$alkyl, $C_{6-10}$aryl$C_{1-4}$alkyl, $C_{6-10}$aryl, $C_{1-7}$heteroaryl, $C_{1-7}$heteroaryl$C_{1-3}$alkyl, $C_{2-8}$heterocyclyl, and $C_{2-8}$heterocyclyl$C_{1-3}$alkyl; or $R^4$ and $R^5$ taken together along with the nitrogen to which they are bound may form a monocyclic or a bicyclic heteroaryl or heterocyclyl which may be optionally substituted with one or more halo or $C_{1-3}$alkyl. In a further embodiment, $R^4$ and $R^5$, for each occurrence, are independently selected from hydrogen and $C_{1-3}$ alkyl.

Further Embodiments

In one embodiment, the combination of $Y_a$ and the moiety

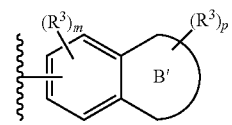

is selected from any one of structures i to xiv below.

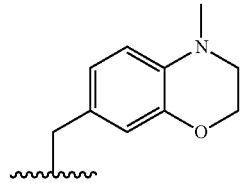

i

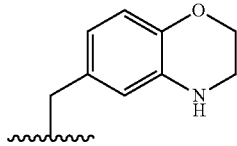

ii

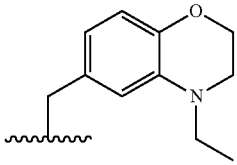

iii

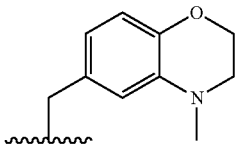

iv

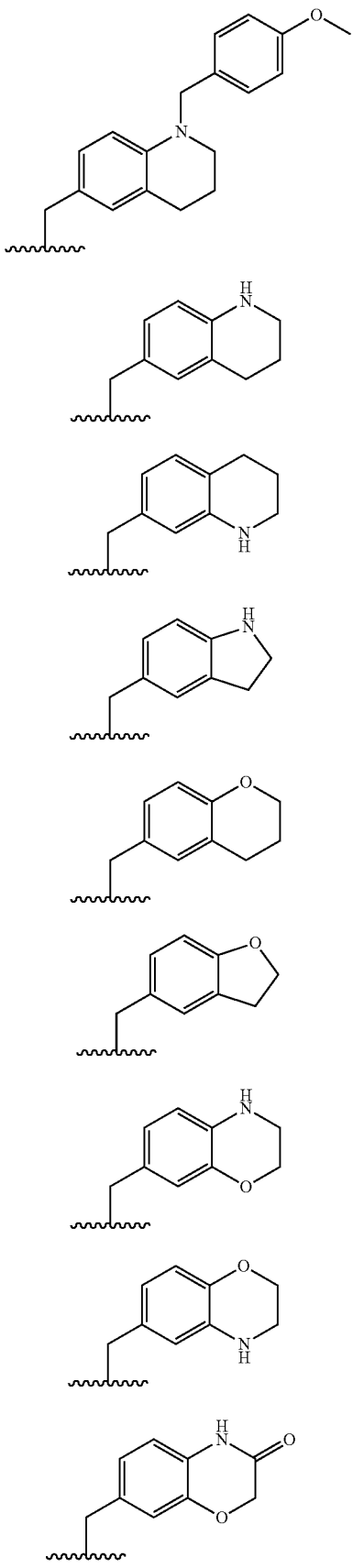

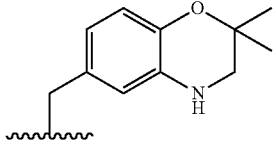

In a further embodiment, said combination is selected from any one of structures i, ii, vi, viii, ix and xi to xiv above.

Specific Compounds

In another aspect of the invention, there is provided a compound selected from compounds 1 to 70 below:

1. (5S,6R,7R,8S)-5-[4-Chloro-3-(4-ethoxy-benzyl)-phenyl]-4-oxa-spiro[2.5]octane-6,7,8-triol
2. (5S,6R,7R,8S)-5-[3-(4-Ethoxy-benzyl)-4-methyl-phenyl]-4-oxa-spiro[2.5]octane-6,7,8-triol
3. (5S,6R,7R,8S)-5-[4-Chloro-3-(4-hydroxy-benzyl)-phenyl]-4-oxa-spiro[2.5]octane-6,7,8-triol
4. (5S,6R,7R,8S)-5-(4-Chloro-3-{4-[(S)-(tetrahydro-furan-3-yl)oxy]-benzyl}-phenyl)-4-oxa spiro[2.5]octane-6,7,8-triol
5. (3S,4R,5R,6S)-6-[4-Chloro-3-(4-ethoxy-benzyl)-phenyl]-2,2-bis-hydroxymethyl-tetrahydro-pyran-3,4,5-triol
6. (3S,4R,5R,6S)-6-[4-chloro-3-(4-ethoxy-benzyl)-phenyl]-2,2-dimethyl-tetrahydro-pyran-3,4,5-triol
7. (5S,6R,7R,8S)-5-[4-Chloro-3-(4-ethoxy-benzyl)-phenyl]-1-hydroxymethyl-4-oxa-spiro[2.5]octane-6,7,8-triol
8. (5S,6R,7R,8S)-5-[3-(4-Ethoxy-benzyl)-phenyl]-1-hydroxymethyl-4-oxa-spiro[2.5]octane-6,7,8-triol
9. (3S,4S,5R)-6-[(R)-3-(4-Ethyl-benzyl)-indol-1-yl]-2,2-bis-hydroxymethyl-tetrahydro-pyran-3,4,5-triol
10. 5R,6R,7S,8S)-5-[2-(4-Methoxy-benzyl)-phenoxy]-4-oxa-spiro[2.5]octane-6,7,8-triol
11. (5S,6R,7R,8S)-5-[4-Chloro-3-(4-hydroxy-benzyl)-phenyl]-4-oxa-spiro[2.5]octane-6,7,8-triol
12. 2-(4-Ethoxy-benzyl)-4-((5S,6R,7R,8S)-6,7,8-trihydroxy-4-oxa-spiro[2.5]oct-5-yl)-benzonitrile
13. 2-[4-(Tetrahydro-furan-3-yloxy)-benzyl]-4-((5S,6R,7R,8S)-6,7,8-trihydroxy-4-oxa-spiro[2.5]oct-5-yl)-benzonitrile
14. 2-(4-Isopropoxy-benzyl)-4-((5S,6R,7R,8S)-6,7,8-trihydroxy-4-oxa-spiro[2.5]oct-5-yl)-benzonitrile
15. (5S,6R,7R,8S)-5-[4-Chloro-3-(4-methyl-benzyl)-phenyl]-4-oxa-spiro[2.5]octane-6,7,8-triol
16. (5S,6R,7R,8S)-5-[3-(4-Ethyl-benzyl)-4-methyl-phenyl]-4-oxa-spiro[2.5]octane-6,7,8-triol
17. (5S,6R,7R,8S)-5-[3-(4-Ethyl-benzyl)-phenyl]-4-oxa-spiro[2.5]octane-6,7,8-triol
18. (5S,6R,7R,8S)-5-[3-(4-Ethoxy-benzyl)-phenyl]-4-oxa-spiro[2.5]octane-6,7,8-triol
19. (5S,6R,7R,8S)-5-[3-(4-Ethoxy-benzyl)-4-ethynyl-phenyl]-4-oxa-spiro[2.5]octane-6,7,8-triol
20. (5S,6R,7R,8S)-5-{3-[5-(4-Fluoro-phenyl)-thiophen-2-ylmethyl]-4-methyl-phenyl}-4-oxa-spiro[2.5]octane-6,7,8-triol
21. (5S,6R,7R,8S)-5-[4-Chloro-3-(5-phenyl-thiophen-2-ylmethyl)-phenyl]-4-oxa-spiro[2.5]octane-6,7,8-triol
22. (5R,6R,7R,8S)-5-[7-(4-Methyl-benzyl)-benzo[b]thiophen-2-yl]-4-oxa-spiro[2.5]octane-6,7,8-triol
23. (5S,6R,7R,8S)-5-(5-Azulen-2-ylmethyl-2-hydroxy-phenyl)-4-oxa-spiro[2.5]octane-6,7,8-triol
24. (5S,6R,7R,8S)-5-(3-Benzo[b]thiophen-2-ylmethyl-4-chloro-phenyl)-4-oxa-spiro[2.5]octane-6,7,8-triol
25. (5R,6R,7R,8S)-5-[4-(4-Methoxy-benzyl)-thiophen-2-yl]-4-oxa-spiro[2.5]octane-6,7,8-triol 26. (5R,6R,7S,8S)-5-[3-(4-Ethyl-benzyl)-indol-1-yl]-4-oxa-spiro[2.5]octane-6,7,8-triol
27. (5S,6R,7R,8S)-5-[4-Chloro-3-(4-ethoxy-benzyl)-phenyl]-1-methyl-4-oxa-spiro[2.5]octane-6,7,8-triol
28. (5S,6R,7R,8S)-5-[4-Chloro-3-(4-ethoxy-benzyl)-phenyl]-1,2-bis-hydroxymethyl-4-oxa-spiro[2.5]octane-6,7,8-triol
29. (5S,6R,7R,8S)-5-[4-Chloro-3-(4-ethoxy-benzyl)-phenyl]-6,7,8-tri hydroxy-4-oxa-spiro[2.5]octane-1-carboxylic acid amide
30. (5S,6R,7R,8S)-5-[4-Chloro-3-(4-ethoxy-benzyl)-phenyl]-1-methoxymethyl-4-oxa-spiro[2.5]octane-6,7,8-triol
31. (3S,4R,5R,6S)-6-[3-(4-Ethyl-benzyl)-phenyl]-2,2-dimethyl-tetrahydro-pyran-3,4,5-triol
32. (6S,7R,8R,9S)-6-[4-Chloro-3-(4-ethoxy-benzyl)-phenyl]-5-oxa-spiro[3.5]nonane-7,8,9-triol
33. (6S,7R,8R,9S)-6-[4-Chloro-3-(4-ethoxy-benzyl)-phenyl]-2,5-dioxa-spiro[3.5]nonane-7,8,9-triol
34. (6S,7R,8R,9S)-6-[4-Chloro-3-(4-ethoxy-benzyl)-phenyl]-7,8,9-trihydroxy-5-oxa-2-aza-spiro[3.5]nonan-1-one
35. (6S,7R,8R,9S)-6-[4-Chloro-3-(4-ethoxy-benzyl)-phenyl]-2-methyl-5-oxa-2-aza-spiro[3.5]nonane-7,8,9-triol
36. 1-{(6S,7R,8R,9S)-6-[4-Chloro-3-(4-ethoxy-benzyl)-phenyl]-7,8,9-trihydroxy-5-oxa-2-aza-spiro[3.5]non-2-yl}-ethanone
37. (6S,7R,8R,9S)-6-[4-Chloro-3-(4-ethoxy-benzyl)-phenyl]-2-ethyl-5-oxa-2-aza-spiro[3.5]nonane-7,8,9-triol
38. (7S,8R,9R,10S)-7-[4-Chloro-3-(4-ethoxy-benzyl)-phenyl]-6-oxa-spiro[4.5]decane-8,9,10-triol
39. (3S,4R,5R,6S)-6-[4-Chloro-3-(4-ethoxy-benzyl)-phenyl]-2-ethyl-2-methyl-tetrahydro-pyran-3,4,5-triol
40. (3S,4R,5R,6S)-6-[4-Chloro-3-(4-ethoxy-benzyl)-phenyl]-2,2-bis-hydroxymethyl-tetrahydro-pyran-3,4,5-triol
41. (3S,4R,5R,6S)-6-[4-Chloro-3-(4-ethoxy-benzyl)-phenyl]-2-hydroxymethyl-2-methoxymethyl-tetrahydro-pyran-3,4,5-triol
42. (3S,4R,5R,6S)-6-[4-Chloro-3-(4-ethoxy-benzyl)-phenyl]-2-hydroxymethyl-2-methyl-tetrahydro-pyran-3,4,5-triol
43. (2S,3R,4R,5S)-2-[4-Chloro-3-(4-ethoxy-benzyl)-phenyl]-3,4,5-trihydroxy-1,8-dioxa-10-aza-spiro[5.5]undecan-9-one
44. (3S,4R,5R,6S)-6-[4-Chloro-3-(4-ethoxy-benzyl)-phenyl]-2,2-bis-methoxymethyl-tetrahydro-pyran-3,4,5-triol
45. (5S,6R,7R)-5-[4-Chloro-3-(4-ethoxy-benzyl)-phenyl]-8-fluoro-4-oxa-spiro[2.5]octane-6,7-diol
46. (3S,4R,5R,6S)-6-[4-Chloro-3-(4-ethoxy-benzyl)-phenyl]-2-fluoromethyl-2-hydroxymethyl-tetrahydro-pyran-3,4,5-triol
47. (3R,4R,5R,6S)-6-[4-Chloro-3-(4-ethoxy-benzyl)-phenyl]-2,2-dimethyl-tetrahydro-pyran-3,4,5-triol
48. (3S,4R,5R,6S)-6-[4-Chloro-3-(4-cyclopropyl-benzyl)-phenyl]-2,2-dimethyl-tetrahydro-pyran-3,4,5-triol
49. (3S,4R,5R,6S)-6-[4-Chloro-3-(4-ethoxy-benzyl)-phenyl]-2,2-diethyl-tetrahydro-pyran-3,4,5-triol
50. (7S,8R,9R,10S)-7-[4-Chloro-3-(4-ethoxy-benzyl)-phenyl]-8,9,10-trihydroxy-6-oxa-1,3-diaza-spiro[4.5]decane-2,4-dione
51. (3S,4R,5R,6S)-6-[4-Chloro-3-(4-ethoxy-benzyl)-phenyl]-2-hydroxymethyl-2-methoxy-tetrahydro-pyran-3,4,5-triol
52. (3S,4R,5R,6S)-6-[4-Chloro-3-(4-ethoxy-benzyl)-phenyl]-2-methoxy-2-methyl-tetrahydro-pyran-3,4,5-triol
53. (3S,4R,5R,6S)-6-[4-Chloro-3-(4-ethoxy-benzyl)-phenyl]-2-fluoro-2-hydroxymethyl-tetrahydro-pyran-3,4,5-triol
54. (5S,6R,7R,8S)-5-[4-Chloro-3-(4-methyl-3,4-dihydro-2H-benzo[1,4]oxazin-7-ylmethyl)-phenyl]-4-oxa-spiro[2.5]octane-6,7,8-triol
55. (3S,4R,5R,6S)-6-[4-Chloro-3-(3,4-dihydro-2H-benzo[1,4]oxazin-6-ylmethyl)-phenyl]-2,2-bis-hydroxymethyl-tetrahydro-pyran-3,4,5-triol
56. (5S,6R,7R,8S)-5-[4-Chloro-3-(3,4-dihydro-2H-benzo[1,4]oxazin-6-ylmethyl)-phenyl]-4-oxa-spiro[2.5]octane-6,7,8-triol
57. (5S,6R,7R,8S)-5-[4-Chloro-3-(2,3-dihydro-benzo[1,4]dioxin-6-ylmethyl)-phenyl]-4-oxa-spiro[2.5]octane-6,7,8-triol
58. 7-[2-Chloro-5-((5S,6R,7R,8S)-6,7,8-trihydroxy-4-oxa-spiro[2.5]oct-5-yl)-benzyl]-4H-benzo[1,4]oxazin-3-one
59. (3S,4R,5R,6S)-6-[4-Chloro-3-(3,4-dihydro-2H-benzo[1,4]oxazin-6-ylmethyl)-phenyl]-2-hydroxymethyl-2-methyl-tetrahydro-pyran-3,4,5-triol
60. (2S,3R,4S)-2-[4-Chloro-3-(3,4-dihydro-2H-benzo[1,4]oxazin-6-ylmethyl)-phenyl]-6,6-bis-hydroxymethyl-tetrahydro-pyran-3,4-diol
61. (2S,3R,4S)-2-[4-Chloro-3-(2,2-dimethyl-3,4-dihydro-2H-benzo[1,4]oxazin-6-ylmethyl)-phenyl]-6,6-bis-hydroxymethyl-tetrahydro-pyran-3,4-diol
62. 6-[2-Chloro-5-((2S,3R,4R,5S)-3,4,5-trihydroxy-6,6-dimethyl-tetrahydro-pyran-2-yl)-benzyl]-3,4-dihydro-2H-benzo[1,4]oxazine-2-carboxylic acid
63. (3S,4R,5R,6S)-6-[4-Chloro-3-(3,4-dihydro-2H-benzo[1,4]oxazin-6-ylmethyl)-phenyl]-2,2-dimethyl-tetrahydro-pyran-3,4,5-triol
64. (3S,4R,5R,6S)-6-[3-(3,4-Dihydro-2H-benzo[1,4]oxazin-6-ylmethyl)-4-methyl-phenyl]-2,2-dimethyl-tetrahydro-pyran-3,4,5-triol
65. (2S,3R,4S)-2-[3-(2,2-Dimethyl-3,4-dihydro-2H-benzo[1,4]oxazin-6-ylmethyl)-4-methoxy-phenyl]-6,6-bis-hydroxymethyl-tetrahydro-pyran-3,4-diol
66. 6-[2-Methoxy-5-((2S,3R,4R,5S)-3,4,5-trihydroxy-6,6-dimethyl-tetrahydro-pyran-2-yl)-benzyl]-3,4-dihydro-2H-benzo[1,4]oxazine-2-carboxylic acid
67. (3S,4R,5R,6S)-6-[4-Chloro-5-(3,4-dihydro-2H-benzo[1,4]oxazin-6-ylmethyl)-2-hydroxy-phenyl]-2,2-dimethyl-tetrahydro-pyran-3,4,5-triol
68. (3S,4R,5R,6S)-6-[3-(3,4-Dihydro-2H-benzo[1,4]oxazin-6-ylmethyl)-4-ethyl-phenyl]-2,2-dimethyl-tetrahydro-pyran-3,4,5-triol
69. (5R,6R,7S,8S)-5-[2-(4-Methyl-benzyl)-phenoxy]-4-oxa-spiro[2.5]octane-6,7,8-trial
70. (5S,6R,7S,8S)-5-[2-(4-Methoxy-benzyl)-thiophen-3-yloxy]-4-oxa-spiro[2.5]octane-6,7,8-triol; or or a pharmaceutically acceptable salt thereof.

Preferably, the compound is one of compounds 1 to 7.
Particularly preferred compounds are the following:
(5S,6S,7R,8S)-6,7,8-tris(benzyloxy)-5-(4-chloro-3-(4-ethoxybenzyl)phenyl)-4-oxaspiro[2.5]octane,
(5S,6R,7R,8S)-5-[4-Chloro-3-(4-ethoxy-benzyl)-phenyl]-4-oxa-spiro[2.5]octane-6,7,8-triol,
(5S,6R,7R,8S)-5-[3-(4-Ethoxy-benzyl)-4-methyl-phenyl]-4-oxa-spiro[2.5]octane-6,7,8-triol,
Acetic acid (5S,6S,7R,8S)-7,8-diacetoxy-5-[4-chloro-3-(4-ethoxy-benzyl)-phenyl]-4-oxa-spiro[2.5]oct-6-yl ester,
Acetic acid (5S,6S,7R,8S)-7,8-diacetoxy-5-[4-chloro-3-(4-hydroxy-benzyl)-phenyl]-4-oxa-spiro[2.5]oct-6-yl ester,
(5S,6R,7R,8S)-5-[4-Chloro-3-(4-hydroxy-benzyl)-phenyl]-4-oxa-spiro[2.5]octane-6,7,8-triol,
(5S,6S,7R,8S)-5-(4-chloro-3-(4-((S)-tetrahydrofuran-3-yloxy)benzyl)phenyl)-4-oxaspiro[2.5]octane-6,7,8-triyl triacetate, (5S,6R,7R,8S)-5-(4-Chloro-3-{4-[(S)-(tetrahydro-furan-3-yl)oxy]-benzyl}-phenyl)-4-oxa spiro[2.5]octane-6,7,8-triol,
((3S,4R,5S,6S)-3,4,5-tris(benzyloxy)-6-(4-chloro-3-(4-ethoxybenzyl)phenyl)tetrahydro-2H-pyran-2,2-diyl)dimethanol,
(3S,4R,5R,6S)-6-[4-Chloro-3-(4-ethoxy-benzyl)-phenyl]-2,2-bis-hydroxymethyl-tetrahydro-pyran-3,4,5-triol,
(3S,4R,5R,6S)-6-[4-chloro-3-(4-ethoxy-benzyl)-phenyl]-2,2-dimethyl-tetrahydro-pyran-3,4,5-triol,
{(5S,6S,7R,8S)-6,7,8-Tris-benzyloxy-5-[4-chloro-3-(4-ethoxy-benzyl)-phenyl]-4-oxa-spiro[2.5]oct-1-yl}-methanol,
{(5S,6S,7R,8S)-6,7,8-Tris-benzyloxy-5-[3-(4-ethoxy-benzyl)-phenyl]-4-oxa-spiro[2.5]oct-1-yl}-methanol,
(5S,6R,7R,8S)-5-[4-Chloro-3-(4-ethoxy-benzyl)-phenyl]-1-hydroxymethyl-4-oxa-spiro[2.5]octane-6,7,8-triol,
(5S,6R,7R,8S)-5-[3-(4-Ethoxy-benzyl)-phenyl]-1-hydroxymethyl-4-oxa-spiro[2.5]octane-6,7,8-triol,
((3S,4S,5R,6S)-3,4,5-tris(benzyloxy)-6-(3-(4-ethylbenzyl)-1H-indol-1-yl)tetrahydro-2H-pyran-2,2-diyl)dimethanol,
3S,4S,5R)-6-[(R)-3-(4-Ethyl-benzyl)-indol-1-yl]-2,2-bis-hydroxymethyl-tetrahydro-pyran-3,4,5-triol,
(6R,7S,8S)-6,7,8-tris(benzyloxy)-5-(2-(4-methoxybenzyl)phenoxy)-4-oxaspiro[2.5]octane,
5R,6R,7S,8S)-5-[2-(4-Methoxy-benzyl)-phenoxy]-4-oxa-spiro[2.5]octane-6,7,8-triol,
(3S,4R,5R,6S)-6-[4-Chloro-3-(3,4-dihydro-2H-benzo[1,4]oxazin-6-ylmethyl)-phenyl]-2,2-bis-hydroxymethyl-tetrahydro-pyran-3,4,5-triol,
(3S,4R,5R,6S)-6-[3-(4-Ethoxy-benzyl)-4-methoxy-phenyl]-2,2-bis-hydroxymethyl-tetrahydro-pyran-3,4,5-triol,
(3S,4R,5R,6S)-6-(3-Chroman-6-ylmethyl-4-ethyl-phenyl)-2,2-bis-hydroxymethyl-tetrahydro-pyran-3,4,5-triol,
(5S,6R,7R,8S)-5-[3-(2,3-Dihydro-benzo[1,4]dioxin-6-ylmethyl)-4-ethyl-phenyl]-4-oxa-spiro[2.5]octane-6,7,8-triol,
(5S,6R,7R,8S)-6-[4-Cyclopropyl-3-(2,3-dihydro-benzo[1,4]dioxin-6-ylmethyl)-phenyl]-4-oxa-spiro[2.5]octane-6,7,8-triol,
(5S,6R,7R,8S)-5-[4-Bromo-3-(2,3-dihydro-benzo[1,4]dioxin-6-ylmethyl)-phenyl]-4-oxa-spiro[2.5]octane-6,7,8-triol,
(5S,6R,7R,8S)-5-[4-Chloro-3-(2,3-dihydro-benzo[1,4]dioxin-6-ylmethyl)-phenyl]-4-oxa-spiro[2.5]octane-6,7,8-triol,
(5S,6R,7R,8S)-5-(4-Chloro-3-chroman-6-ylmethyl-phenyl)-4-oxa-spiro[2.5]octane-6,7,8-triol,
(5S,6R,7R,8S)-5-[3-(4-Ethoxy-benzyl)-4-methoxy-phenyl]-4-oxa-spiro[2.5]octane-6,7,8-triol,
{(3S,4R,5S,6S)-3,4,5-tris-benzyloxy-6-[4-chloro-3-(4-ethoxy-benzyl)-phen yl]-2-methyl-tetrahydro-pyran-2-yl}-methanol,
(3S,4R,5R,6S)-6-[4-chloro-3-(4-ethoxy-benzyl)-phenyl]-2-hydroxy methyl-2-methyl-tetrahydro-pyran-3,4,5-triol,
(3S,4R,5S,6S)-3,4,5-tris-benzyloxy-6-[4-chloro-3-(4-ethoxy-benzyl)-phenyl]-2-hydroxymethyl-tetrahydro-pyran-2-ol,
(3S,4R,5R,6S)-6-[4-Chloro-3-(4-ethoxy-benzyl)-phenyl]-2-hydroxymethyl-tetrahydro-pyran-2,3,4,5-tetraol,
(3S,4R,5R,6S)-6-[4-Chloro-3-(4-ethoxy-benzyl)-phenyl]-2-hydroxymethyl-2-methoxy-tetrahydro-pyran-3,4,5-triol,
(6S,7S,8R,9S)-7,8,9-tris-benzyloxy-6-[4-chloro-3-(4-ethoxy-benzyl)-phenyl]-2,5-dioxa-spiro[3.5]nonane,
(6S,7R,8R,9S)-6-[4-chloro-3-(4-ethoxy-benzyl)-phenyl]-2,5-dioxa-spiro[3.5]nonane-7,8,9-triol,
(6S,7R,8R,9S)-6-(3-Chroman-6-ylmethyl-4-ethyl-phenyl)-2,5-dioxa-spiro[3.5]nonane-7,8,9-triol,
(5S,6S,7R,8S)-5-(4-chloro-3-(4-(pyrrolidin-1-yl)benzyl)phenyl)-4-oxaspiro[2.5]octane-6,7,8-triyl triacetate,
5S,6R,7R,8S)-5-[4-chloro-3-(4-pyrrolidin-1-yl-benzyl)-phenyl]-4-oxa-spiro[2.5]octane-6,7,8-triol,
(5S,6R,7R,8S)-5-{3-[4-(Benzyl-ethyl-amino)-benzyl]-4-chloro-phenyl}-4-oxa-spiro[2.5]octane-6,7,8-triol,
(5S,6R,7R,8S)-5-[4-Chloro-3-(4-ethylamino-benzyl)-phenyl]-4-oxa-spiro[2.5]octane-6,7,8-triol,
(5S,6R,7R,8S)-5-[4-chloro-3-(3,4-dihydro-2H-benzo[1,4]oxazin-6-ylmethyl)-phenyl]-4-oxa-spiro[2.5]octane-6,7,8-triol,
Acetic acid (5S,6S,7R,8S)-7,8-diacetoxy-5-[4-chloro-3-(4-hydroxy-3-nitro-benzyl)-phenyl]-4-oxa-spiro[2.5]oct-6-yl ester,
Acetic acid (5S,6S,7R,8S)-6,7-diacetoxy-5-[4-chloro-3-(3-oxo-3,4-dihydro-2H-benzo[1,4]oxazin-6-ylmethyl)-phenyl]-4-oxa-spiro[2.5]oct-8-yl ester,
Acetic acid (5S,6S,7R,8S)-6,7-diacetoxy-5-[4-chloro-3-(3,4-dihydro-2H-benzo[1,4]oxazin-6-ylmethyl)-phenyl]-4-oxa-spiro[2.5]oct-8-yl ester, and
(5S,6R,7R,8S)-5-[4-chloro-3-(3,4-dihydro-2H-benzo[1,4]oxazin-6-ylmethyl)-phenyl]-4-oxa-spiro[2.5]octane-6,7,8-triol,
or a pharmaceutically accept salt thereof.

Compounds of Formula (I), (IA), (I-i), (I-iii), (I-iv) and (I-v) Etc. and Derivatives Thereof As used herein, the terms "compound of the invention" and "compound of Formula (I)" etc. include pharmaceutically acceptable derivatives thereof and polymorphs, isomers and isotopically labelled variants thereof. Furthermore, the term "compounds of the invention" and "compound of Formula (I)" etc. include compounds of formulae (I), (IA), (I-i), (I-ii), (I-iii), (I-iv) and (I-v), and the embodiments thereof disclosed herein.

Pharmaceutically Acceptable Derivatives

The term "pharmaceutically acceptable derivative" includes any pharmaceutically acceptable salt, solvate, hydrate or prodrug of a compound of Formula (I). In one embodiment, the pharmaceutically acceptable derivatives are pharmaceutically acceptable salts, solvates or hydrates of a compound of Formula (I). The invention includes pharmaceutically acceptable derivatives of Formula (I).

Pharmaceutically Acceptable Salts

The term "pharmaceutically acceptable salt" includes a salt prepared from pharmaceutically acceptable non-toxic acids or bases including inorganic or organic acids and bases.

Compounds of Formula (I) which contain basic, e.g. amino, groups are capable of forming pharmaceutically acceptable salts with acids. In one embodiment, pharmaceutically acceptable acid addition salts of the compounds of Formula (I) include, but are not limited to, those of inorganic acids such as hydrohalic acids (e.g. hydrochloric, hydrobromic and hydroiodic acid), sulfuric acid, nitric acid, and phosphoric acids. In one embodiment, pharmaceutically acceptable acid addition salts of the compounds of Formula (I) include, but are not limited to, those of organic acids such as aliphatic, aromatic, carboxylic and sulfonic classes of organic acids, examples of which include: aliphatic monocarboxylic acids such as formic acid, acetic acid, propionic acid or butyric acid; aliphatic hydroxy acids such as lactic acid, citric acid, tartaric acid or malic acid; dicarboxylic acids such as maleic acid or succinic acid; aromatic carboxylic acids such as benzoic acid, p-chlorobenzoic acid, phenylacetic acid, diphenylacetic acid or triphenylacetic acid; aromatic hydroxyl acids such as o-hydroxybenzoic acid, p-hydroxybenzoic acid, 1-hydroxynaphthalene-2-carboxylic acid or 3-hydroxynaphthalene-2-carboxylic acid; and sulfonic acids such as methanesulfonic acid, ethanesulfonic acid or benzenesulfonic acid. Other pharmaceutically acceptable acid addition salts of the compounds of Formula (I) include, but are not limited to, those of glycolic acid, glucuronic acid, furoic acid, glutamic acid, anthranilic acid, salicylic acid, mandelic acid, embonic (pamoic) acid, pantothenic acid, stearic acid, sulfanilic acid, algenic acid, and galacturonic acid.

Compounds of Formula (I) which contain acidic, e.g. carboxyl, groups are capable of forming pharmaceutically acceptable salts with bases. In one embodiment, pharmaceutically acceptable basic salts of the compounds of Formula (I) include, but are not limited to, metal salts such as alkali metal or alkaline earth metal salts (e.g. sodium, potassium, magnesium or calcium salts) and zinc or aluminium salts. In one embodiment, pharmaceutically acceptable basic salts of the compounds of Formula (I) include, but are not limited to, salts formed with ammonia or pharmaceutically acceptable organic amines or heterocyclic bases such as ethanolamines (e.g. diethanolamine), benzylamines, N-methyl-glucamine, amino acids (e.g. lysine) or pyridine.

Hemisalts of acids and bases may also be formed, e.g. hemisulphate salts.

Pharmaceutically acceptable salts of compounds of Formula (I) may be prepared by methods well-known in the art.

For a review of pharmaceutically acceptable salts, see Stahl and Wermuth, Handbook of Pharmaceutical Salts: Properties, Selection and Use (Wiley-VCH, Weinheim, Germany, 2002).

Solvates & Hydrates

The compounds of the invention may exist in both unsolvated and solvated forms. The term "solvate" includes molecular complexes comprising a compound of the invention and one or more pharmaceutically acceptable solvent molecules such as water or $C_{1-6}$ alcohols, e.g. ethanol. The term "hydrate" means a "solvate" where the solvent is water. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

Prodrugs

The invention includes prodrugs of the compounds of Formula (I). Prodrugs are derivatives of compounds of Formula (I) (which may have little or no pharmacological activity themselves), which can, when administered in vivo, be converted into compounds of Formula (I).

Prodrugs can, for example, be produced by replacing functionalities present in the compounds of Formula (I) with appropriate moieties which are metabolized in vivo to form a compound of Formula (I). The design of prodrugs is well-known in the art, as discussed in Bundgaard, *Design of Prodrugs* 1985 (Elsevier), *The Practice of Medicinal Chemistry* 2003, 2nd Ed, 561-585 and Leinweber, *Drug Metab. Res.* 1987, 18: 379. A discussion of prodrugs is provided in Higuchi, T., et al., "Prodrugs as Novel Delivery Systems," A.C.S. Symposium Series, Vol. 14, and in Bioreversible Carriers in Drug Design, ed. Edward B. Roche, Anglican Pharmaceutical Association and Pergamon Press, 1987.

Examples of prodrugs of compounds of Formula (I) are esters and amides of the compounds of Formula (I). For example, where the compound of Formula (I) contains a carboxylic acid group (—COOH), the hydrogen atom of the carboxylic acid group may be replaced in order to form an ester (e.g. the hydrogen atom may be replaced by $C_{1-6}$alkyl). Where the compound of Formula (I) contains an alcohol group (—OH), the hydrogen atom of the alcohol group may be replaced in order to form an ester (e.g. the hydrogen atom may be replaced by —C(O)$C_{1-6}$alkyl. Where the compound of Formula (I) contains a primary or secondary amino group, one or more hydrogen atoms of the amino group may be replaced in order to form an amide (e.g. one or more hydrogen atoms may be replaced by —C(O)$C_{1-6}$alkyl).

In one embodiment of the present invention, the prodrug is selected from a group comprising, esters and hydrates.

Amorphous & crystalline forms

The compounds of the invention may exist in solid states from amorphous through to crystalline forms. All such solid forms are included within the invention.

Isomeric Forms

Compounds of the invention may exist in one or more geometrical, optical, enantiomeric, diastereomeric and tautomeric forms, including but not limited to cis- and trans-forms, E- and Z-forms, R-, S- and meso-forms, keto-, and enol-forms. All such isomeric forms are included within the invention. The isomeric forms may be in isomerically pure or enriched form, as well as in mixtures of isomers (e.g. racemic or diastereomeric mixtures).

Accordingly, the invention provides:
stereoisomeric mixtures of compounds of Formula (I);
a diastereomerically enriched or diastereomerically pure isomer of a compound of Formula (I); or
an enantiomerically enriched or enantiomerically pure isomer of a compound of Formula (I).

Where appropriate isomers can be separated from their mixtures by the application or adaptation of known methods (e.g. chromatographic techniques and recrystallisation techniques). Where appropriate isomers can be prepared by the application or adaptation of known methods (e.g. asymmetric synthesis).

Unless otherwise indicated, the present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, such as HPLC using a chiral column. When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are non-superimposeable mirror images of one another.

Isotopic Labeling

The invention includes pharmaceutically acceptable isotopically-labelled corn pounds of Formula (I) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^{2}H$ and $^{3}H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{38}S$. Certain isotopically-labelled compounds of Formula (I), for example, those incorporating a radioactive isotope, are useful in drug and/or substrate tissue distribution studies. The radioactive isotopes $^3$H and $^{14}$C are particularly useful for this purpose in view of their ease of incorporation and ready means of detection.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labelled compounds of Formula (I) can generally be prepared by conventional techniques known to those skilled in the art or by processes analogous to those described herein using an appropriate isotopically-labelled reagent in place of the non-labelled reagent previously employed.

Therapeutic Definitions

As used herein, "treatment" includes curative and prophylactic treatment. As used herein, a "patient" means an animal, preferably a mammal, preferably a human, in need of treatment.

The amount of the compound of the invention administered should be a therapeutically effective amount where the compound or derivative is used for the treatment of a disease or condition or a prophylactically effective amount where the compound or derivative is used for the prevention of a disease or condition.

The term "therapeutically effective amount" used herein refers to the amount of compound needed to treat or ameliorate a targeted disease or condition or a symptom thereof. The term "prophylactically effective amount" used herein refers to the amount of compound needed to prevent a targeted disease or condition or a symptom thereof. The exact dosage will generally be dependent on the patient's status at the time of administration. Factors that may be taken into consideration when determining dosage include the severity of the disease state in the patient, the general health of the patient, the age, weight, gender, diet, time, frequency and route of administration, drug combinations, reaction sensitivities and the patient's tolerance or response to therapy. The precise amount can be determined by routine experimentation, but may ultimately lie with the judgement of the clinician. Generally, an effective dose will be from 0.01 mg/kg/day (mass of drug compared to mass of patient) to 1000 mg/kg/day, e.g. 1 mg/kg/day to 100 mg/kg/day or 1 mg/kg/day to 10 mg/kg/day. Compositions may be administered individually to a patient or may be administered in combination with other agents, drugs or hormones.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians. As used herein, the term "disorder" is synonymous with "condition".

Treatment of Diseases and Conditions

Compounds of Formula (I) have been found to be inhibitors of SGLT. As used herein, inhibition of SGLT means inhibition exclusively of SGLT2, inhibition exclusively of SGLT1 or inhibition of both SGLT1 and SGLT2.

The invention provides a compound of Formula (I) for use in therapy. The invention further provides a pharmaceutical composition comprising a compound of Formula (I) in combination with a pharmaceutically acceptable excipient.

The invention further provides a method for the treatment of a disease or condition mediated by the sodium D-glucose co-transporter, comprising the step of administering a therapeutically effective amount of a compound of Formula (I) to a patient. The invention also provides the use of a compound of Formula (I) in the manufacture of a medicament for the treatment of a disease or condition mediated by the sodium D-glucose co-transporter. The invention also provides a compound of Formula (I) for use in treating a disease or condition mediated by the sodium D-glucose co-transporter.

The SGLT inhibitory activity of the compounds of the invention may be demonstrated by the SGLT2 and SGLT1 assays disclosed hereinbelow. Preferred compounds of the invention have an $IC_{50}$ in the SGLT2 assay of <100 nM, in one embodiment <30 nM, in one embodiment <20 nM, in one embodiment <10 nM, in another embodiment <5 nM, and in another embodiment <1 nM, and in another embodiment <0.5 nM. In another embodiment, preferred compounds of the invention have an $IC_{50}$ in the SGLT1 assay of <10,000 nM, in one embodiment <1500 nM, in one embodiment <1000 nM, in one embodiment <700 nM, in another embodiment <500 nM and in another embodiment <200 nM.

The present invention also provides a method of treating diabetes comprising administering a compound of Formula (I), or a pharmaceutically acceptable salt thereof, to a subject in need thereof.

In another embodiment, the invention provides a method of treating a disease or condition mediated by the sodium D-glucose co-transporter in a mammal, comprising administering to the mammal in need thereof a therapeutically effective amount of a compound of Formula (I), or a pharmaceutically acceptable salt thereof.

The compounds of the present invention are useful as both prophylactic and therapeutic treatments for diseases or conditions related to the inhibition of SGLT-2 and SGLT-1.

Diseases and Conditions Mediated by the Sodium D-Glucose Co-Transporter

The invention is useful for the treatment of a disease or disorder mediated by the sodium D-glucose co-transporter. Diseases and conditions mediated by the sodium D-glucose co-transporter include: metabolic disorders, retinopathy, nephropathy, diabetic foot, ulcers, macroangiopathies, metabolic acidosis or ketosis, reactive hypoglycaemia, hyperinsulinaemia, glucose metabolic disorder, insulin resistance, metabolic syndrome (such as dyslipidemia, obesity, insulin resistance, hypertension, microalbuminemia, hyperuricaemia, and hypercoagulability), dyslipidaemias of different origins, atherosclerosis and related diseases, high blood pressure, chronic heart failure, edema, hyperuricaemia, Syndrome X, diabetes, insulin resistance, decreased glucose tolerance (also known as impaired glucose tolerance, IGT), non-insulin-dependent diabetes mellitus, Type II diabetes, Type I diabetes, diabetic complications, body weight disorders, weight loss, body mass index and leptin related diseases. In one embodiment, the diseases and conditions include metabolic syndrome (such as dyslipidemia, obesity, insulin resistance, hypertension, microalbuminemia, hyperuricaemia, and hypercoagulability), Syndrome X, diabetes, insulin resistance, decreased glucose tolerance (also known as impaired glucose tolerance, IGT), non-insulin-dependent diabetes mellitus, Type II diabetes, Type I diabetes, diabetic complications, body weight disorders, weight loss, body mass index and leptin related diseases. In one embodiment, the disease or disorder is decreased glucose tolerance, Type II diabetes or obesity.

Compounds of formula (I) may be also suitable for preventing beta-cell degeneration such as apoptosis or necrosis of pancreatic beta cells, for improving or restoring the functionality of pancreatic cells, increasing the number and size of pancreatic beta cells, for use as diuretics or antihypertensives and for the prevention and treatment of acute renal failure.

As a further aspect, the invention relates to a method for treating a disorder selected from type I and type II diabetes mellitus, complications of diabetes, comprising administration of an effective amount of a compound of formula (I) or a pharmaceutically acceptable salt thereof.

As used herein a patient is suffering from "obesity" if the patient exhibits at least one of:
- a body mass index (BMI), i.e. the patient's mass (in kg) divided by the square of the patient's height (in m), of 30 or more;
- an absolute waist circumference of >102 cm in men or >88 cm in women;
- a waist-to-hip ratio>0.9 in men or >0.85 in women; or
- a percent body fat>25% in men or >30% in women.

As used herein a patient is suffering from "Type II diabetes" if they meet the World Health Organisation criteria for Diabetes diagnosis (Definition and diagnosis of diabetes mellitus and intermediate hyperglycaemia, WHO, 2006), i.e. the patient exhibits at least one of:
- a fasting plasma glucose≧7.0 mmol/l (126 mg/dl); or
- a venous plasma glucose 211.1 mmol/l (200 mg/dl) 2 hours after ingestion of 75 g oral glucose load.

As used herein a patient is suffering from "IGT" if they meet the World Health Organisation criteria for IGT diagnosis (Definition and diagnosis of diabetes mellitus and intermediate hyperglycaemia, WHO, 2006), i.e. the patient exhibits both of:
- a fasting plasma glucose<7.0 mmol/l (126 mg/dl); and
- a venous plasma glucose≧7.8 and <11.1 mmol/l (200 mg/dl) 2 hours after ingestion of 75 g oral glucose load.

Administration & Formulation

General

For pharmaceutical use, the compounds of the invention may be administered as a medicament by enteral or parenteral routes, including intravenous, intramuscular, subcutaneous, transdermal, airway (aerosol), oral, intranasal, rectal, vaginal and topical (including buccal and sublingual) administration. The compounds of Formula (I) should be assessed for their biopharmaceutical properties, such as solubility and solution stability (across pH), permeability, etc., in order to select the most appropriate dosage form and route of administration for treatment of the proposed indication.

The compounds of the invention may be administered as crystalline or amorphous products. The compounds of the invention may be administered alone or in combination with one or more other compounds of the invention or in combination with one or more other drugs (or as any combination thereof). Generally, they will be administered as a formulation in association with one or more pharmaceutically acceptable excipients. The term "excipient" includes any ingredient other than the compound(s) of the invention which may impart either a functional (e.g drug release rate controlling) and/or a non-functional (e.g. processing aid or diluent) characteristic to the formulations. The choice of excipient will to a large extent depend on factors such as the particular mode of administration, the effect of the excipient on solubility and stability, and the nature of the dosage form.

The present invention provides a pharmaceutical composition comprising a compound according to Formula (I) and a pharmaceutically acceptable excipient.

Typical pharmaceutically acceptable excipients include:
- diluents, e.g. lactose, dextrose, sucrose, mannitol, sorbitol, cellulose and/or glycine;
- lubricants, e.g. silica, talcum, stearic acid, its magnesium or calcium salt and/or polyethyleneglycol;
- binders, e.g. magnesium aluminum silicate, starch paste, gelatin, tragacanth, methylcellulose, sodium carboxymethylcellulose and/or polyvinylpyrrolidone;
- disintegrants, e.g. starches, agar, alginic acid or its sodium salt, or effervescent mixtures; and/or
- absorbants, colorants, flavors and/or sweeteners.

A thorough discussion of pharmaceutically acceptable excipients is available in Gennaro, *Remington: The Science and Practice of Pharmacy* 2000, 20th edition (ISBN: 0683306472).

Accordingly, in one embodiment, the present invention provides a pharmaceutical composition comprising a compound of Formula (I) and a pharmaceutically acceptable excipient.

Oral Administration

The compounds of the invention may be administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid plugs, solid microparticulates, semi-solid and liquid (including multiple phases or dispersed systems) such as tablets; soft or hard capsules containing multi- or nano-particulates, liquids (e.g. aqueous solutions), emulsions or powders; lozenges (including liquid-filled); chews; gels; fast dispersing dosage forms; films; ovules; sprays; and buccal/mucoadhesive patches.

Formulations suitable for oral administration may also be designed to deliver the compounds of Formula (I) in an immediate release manner or in a rate-sustaining manner, wherein the release profile can be delayed, pulsed, controlled, sustained, or delayed and sustained or modified in such a manner which optimises the therapeutic efficacy of the said compounds. Means to deliver compounds in a rate-sustaining manner are known in the art and include slow release polymers that can be formulated with the said compounds to control their release.

Examples of rate-sustaining polymers include degradable and non-degradable polymers that can be used to release the said compounds by diffusion or a combination of diffusion and polymer erosion. Examples of rate-sustaining polymers include hydroxypropyl methylcellulose, hydroxypropyl cellulose, methyl cellulose, ethyl cellulose, sodium carboxymethyl cellulose, polyvinyl alcohol, polyvinyl pyrrolidone, xanthum gum, polymethacrylates, polyethylene oxide and polyethylene glycol.

Liquid (including multiple phases and dispersed systems) formulations include emulsions, suspensions, solutions, syrups and elixirs. Such formulations may be presented as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Liang and Chen, *Expert Opinion in Therapeutic Patents* 2001, 11(6): 981-986.

The formulation of tablets is discussed in H. Lieberman and L. Lachman, *Pharmaceutical Dosage Forms: Tablets* 1980, vol. 1 (Marcel Dekker, New York).

Parenteral Administration

The compounds of the invention can be administered parenterally.

The compounds of the invention may be administered directly into the blood stream, into subcutaneous tissue, into muscle, or into an internal organ. Suitable means for administration include intravenous, intraarterial, intrathecal, intraventricular, intraurethral, intrasternal, intracranial, intramuscular, intrasynovial and subcutaneous. Suitable devices for administration include needle (including microneedle) injectors, needle-free injectors and infusion techniques.

Parenteral formulations are typically aqueous or oily solutions. Where the solution is aqueous, excipients such as sugars (including but restricted to glucose, mannitol, sorbitol, etc.) salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water (WFI).

Parenteral formulations may include implants derived from degradable polymers such as polyesters (i.e. polylactic acid, polylactide, polylactide-co-glycolide, polycapro-lactone, polyhydroxybutyrate), polyorthoesters and polyanhydrides. These formulations may be administered via surgical incision into the subcutaneous tissue, muscular tissue or directly into specific organs.

The preparation of parenteral formulations under sterile conditions, for example, by lyophilisation, may readily be accomplished using standard pharmaceutical techniques well known to those skilled in the art.

The solubility of compounds of Formula (I) used in the preparation of parenteral solutions may be increased by the use of appropriate formulation techniques, such as the incorporation of co-solvents and/or solubility-enhancing agents such as surfactants, micelle structures and cyclodextrins.

Inhalation & Intranasal Administration

The compounds of the invention can be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler, as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

Formulations for inhaled/intranasal administration may be formulated to be immediate and/or modified release using, for example, PGLA. Modified release formulations include delayed-, sustained-, pulsed-, controlled-, targeted and programmed release.

Transdermal Administration

Suitable formulations for transdermal application include a therapeutically effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Combination Therapy

A compound of formula (I) of the present invention may be usefully combined with another pharmacologically active compound, or with two or more other pharmacologically active compounds, for use in therapy. For example, a compound of the formula (I), or a pharmaceutically acceptable salt thereof, as defined above, may be administered simultaneously, sequentially or separately in combination with one or more agents for the treatment of disorders previously listed.

Therapeutic agents which are suitable for such a combination include, for example, antidiabetic agents such as metformin, sulphonylureas (e.g. glibenclamide, tolbutamide, glimepiride), nateglinide, repaglinide, thiazolidinediones (e.g. rosiglitazone, pioglitazone), PPAR-gamma-agonists (e.g. GI 262570) and antagonists, PPAR-gamma/alpha modulators (e.g. KRP 297), alpha-glucosidase inhibitors (e.g. acarbose, voglibose), DPPIV inhibitors (e.g. LAF237, MK-431), alpha2-antagonists, insulin and insulin analogues, GLP-1 and GLP-1 analogues (e.g. exendin-4) or amylin. The list also includes inhibitors of protein tyrosinephosphatase 1, substances that affect deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, lipid lowering agents such as for example HMG-CoA-reductase inhibitors (e.g. simvastatin, atorvastatin), fibrates (e.g. bezafibrate, fenofibrate), nicotinic acid and the derivatives thereof, PPAR-alpha agonists, PPAR-delta agonists, ACAT inhibitors (e.g. avasimibe) or cholesterol absorption inhibitors such as, for example, ezetimibe, bile acid-binding substances such as, for example, cholestyramine, inhibitors of ileac bile acid transport, HDL-raising compounds such as CETP inhibitors or ABC1 regulators or active substances for treating obesity, such as sibutramine or tetrahydrolipostatin, dexfenfluramine, axokine, antagonists of the cannabinoidi receptor, MCH-1 receptor antagonists, MC4 receptor agonists, NPY5 or NPY2 antagonists or β3-agonists such as SB-418790 or AD-9677 and agonists of the 5HT2c receptor.

Moreover, combinations with drugs for influencing high blood pressure, chronic heart failure or atherosclerosis such as e.g. A-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte aggregation inhibitors and others or combinations thereof are suitable. Examples of angiotensin II receptor antagonists are candesartan cilexetil, potassium losartan, eprosartan mesylate, valsartan, telmisartan, irbesartan, EXP-3174, L-158809, EXP-3312, olmesartan, medoxomil, tasosartan, KT-3-671, GA-0113, RU-64276, EMD-90423, BR-9701, etc. Angiotensin II receptor antagonists are preferably used for the treatment or prevention of high blood pressure and complications of diabetes, often combined with a diuretic such as hydrochlorothiazide.

A combination with uric acid synthesis inhibitors or uricosurics is suitable for the treatment or prevention of gout.

A combination with GABA-receptor antagonists, Na-channel blockers, topiramat, protein-kinase C inhibitors, advanced glycation end product inhibitors or aldose reductase inhibitors may be used for the treatment or prevention of complications of diabetes.

Such combinations may offer significant advantages, including synergistic activity, in therapy.

The present invention thus provides:

The use of an agent selected from the group consisting of insulin, insulin derivative or mimetic; insulin secretagogue; insulinotropic sulfonylurea receptor ligand; PPAR ligand; insulin sensitizer; biguanide; alpha-glucosidase inhibitors; GLP-1, GLP-1 analog or mimetic; DPPIV inhibitor; HMG-CoA reductase inhibitor; squalene synthase inhibitor; FXR or LXR ligand; cholestyramine; fibrates; nicotinic acid, and aspirin in the manufacture of a medicament for the treatment of a disease or condition in a subject mediated by the sodium D-glucose co-transporter, wherein the agent is administered in combination with a compound according to Formula (I);

The use of a compound according to Formula (I) in the manufacture of a medicament for the treatment of a disease or condition in a subject mediated by the sodium D-glucose co-transporter, wherein the compound is administered in combination with an agent selected from the group consisting of insulin, insulin derivative or mimetic; insulin secretagogue; insulinotropic sulfonylurea receptor ligand; PPAR ligand; insulin sensitizer; biguanide; alpha-glucosidase inhibitors; GLP-1, GLP-1 analog or mimetic; DPPIV inhibitor; HMG-CoA reductase inhibitor; squalene synthase inhibitor; FXR or LXR ligand; cholestyramine; fibrates; nicotinic acid, and aspirin, and The use of a compound according to any one of claims 1 to 36 in combination with an agent selected from the group consisting of insulin, insulin derivative or mimetic; insulin secretagogue; insulinotropic sulfonylurea receptor ligand; PPAR ligand; insulin sensitizer; biguanide; alpha-glucosidase inhibitors; GLP-1, GLP-1 analog or mimetic; DPPIV inhibitor; HMG-CoA reductase inhibitor; squalene synthase inhibitor; FXR or LXR ligand; cholestyramine; fibrates; nicotinic acid, and aspirin in the manufacture of a medicament for treating a disease or condition in a subject mediated by the sodium D-glucose co-transporter, Wherein the diseases or conditions may be as described herein.

The present invention also provides a pharmaceutical composition comprising a therapeutically effective amount of a compound of Formula (I) in combination with a therapeutically effective amount of insulin, insulin derivative or mimetic; insulin secretagogue; insulinotropic sulfonylurea receptor ligand; PPAR ligand; insulin sensitizer; biguanide; alpha-glucosidase inhibitors; GLP-1, GLP-1 analog or mimetic; DPPIV inhibitor; HMG-CoA reductase inhibitor; squalene synthase inhibitor; FXR or LXR ligand; cholestyramine; fibrates; nicotinic acid; or aspirin. In another embodiment, the invention provides a product comprising a compound of Formula (I) and an agent selected from the group consisting of insulin, insulin derivative or mimetic; insulin secretagogue; insulinotropic sulfonylurea receptor ligand; PPAR ligand; insulin sensitizer; biguanide; alpha-glucosidase inhibitors; GLP-1, GLP-1 analog or mimetic; DPPIV inhibitor; HMG-CoA reductase inhibitor; squalene synthase inhibitor; FXR or LXR ligand; cholestyramine; fibrates; nicotinic acid, and aspirin for simultaneous, separate or sequential use in therapy.

Chemical Definitions

As used herein, the term "alkyl" refers to a fully saturated branched or unbranched hydrocarbon moiety. Preferably the alkyl comprises 1 to 20 carbon atoms, more preferably 1 to 16 carbon atoms, 1 to 10 carbon atoms, 1 to 6 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, or n-decyl.

"Alkylene" refers to a straight or branched divalent hydrocarbon chain consisting solely of carbon and hydrogen atoms, having from one to twelve carbon atoms, preferably one to 6 carbon atoms, and linking the rest of the molecule to a radical group. Examples of alkylene groups include methylene, ethylene, propylene, n-butylene, and the like. The alkylene is attached to the rest of the molecule through a single bond and to the radical group through a single bond. The points of attachment of the alkylene to the rest of the molecule and to the radical group can be through one carbon or any two carbons within the chain.

"Halogen" or "halo" may be fluoro, chloro, bromo or iodo.

The term "alkenyl" refers to a monovalent hydrocarbon having at least one carbon-carbon double bond. The term "$C_2$-$C_6$alkenyl" refers to a monovalent hydrocarbon having two to six carbon atoms and comprising at least one carbon-carbon double bond.

The term "alkynyl" refers to a monovalent hydrocarbon having at least one carbon-carbon triple bond. The term "$C_2$-$C_6$-alkynyl" refers to a monovalent hydrocarbon having two to six carbon atoms and comprising at least one carbon-carbon triple bond.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Preferably, alkoxy groups have about 1-6, more preferably about 1-4 carbons.

Alkyl, alkenyl, alkynyl, and alkoxy groups, containing the requisite number of carbon atoms, can be unbranched or branched. The requisite number of carbon may be represented as $C_{1-6}$, $C_{1-4}$, etc.

The term "aryl" refers to monocyclic or bicyclic aromatic hydrocarbon groups having 6-10 carbon atoms in the ring portion. Non-limiting examples include phenyl and naphthyl.

The term "aryl" also refers to a group in which an aryl ring is fused to one or more cycloalkyl or heterocyclyl rings, where the radical or point of attachment is on the aryl ring. Nonlimiting examples include 2,3-dihydro-1H-indene, 1,2,3,4-tetrahydronaphthyl and 3,4-dihydro-2H-benzo[b][1,4]oxazinyl.

The term "arylalkyl" refers to an aryl group which is linked to another moiety via an alkyl group which may be branched or unbranched. Examples of arylalkyl groups include benzyl, 2-phenyl-ethyl, 2-(naphth-2-yl)-butan-1-yl, and the like.

The term "aryloxy" refers to an aryl group which is linked to another moiety through an oxygen atom, such as phenoxy.

As used herein, the term "heterocyclyl" refers to an optionally substituted, saturated or unsaturated non-aromatic ring or ring system, e.g., which is a 4-, 5-, 6-, or 7-membered monocyclic, 7-, 8-, 9-, 10-, 11-, or 12-membered bicyclic or 10-, 11-, 12-, 13-, 14- or 15-membered tricyclic ring system and contains at least one heteroatom selected from O, S and N, where the N and S can also optionally be oxidized to various oxidation states.

The heterocyclic group can be attached at a heteroatom or a carbon atom. The heterocyclyl can include fused or bridged rings as well as spirocyclic rings. Examples of heterocycles include dihydrofuranyl, [1,3]dioxolane, 1,4-dioxane, 1,4-dithiane, piperazinyl, 1,3-dioxolane, imidazolidinyl, imidazolinyl, pyrrolidine, dihydropyran, oxathiolane, dithiolane, 1,3-dioxane, 1,3-dithianyl, oxathianyl, thiomorpholinyl, oxiranyl, aziridinyl, oxetanyl, azetidinyl, tetrahydrofuranyl, pyrrolidinyl, tetrahydropyranyl, piperidinyl, morpholinyl, piperazinyl, azepinyl, oxapinyl, oxazepinyl and diazepinyl. As used herein, the term "cycloalkyl" refers to saturated or partially unsaturated (but not aromatic) monocyclic, bicyclic or tricyclic hydrocarbon groups of 3-12 carbon atoms, preferably 3-9, or 3-7 carbon atoms, Exemplary monocyclic hydrocarbon groups include, but are not limited to, cyclopropyl, cyclobutyl, cyclopentyl, cyclopentenyl, cyclohexyl or cyclohexenyl. Exemplary bicyclic hydrocarbon groups include bornyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, or bicyclo[2.2.2]octyl. Exemplary tricyclic hydrocarbon groups include adamantyl.

The term "heterocycloxy" refers to a heterocyclyl which is linked to another moiety through an oxygen atom, e.g. piperazin-2-yloxy.

As used herein, the term "heteroaryl" refers to a 5-14 membered monocyclic- or bicyclic- or polycyclic-aromatic ring system having 1 to 8 heteroatoms selected from N, O or S. Preferably, the heteroaryl is a 5-10 or 5-7 membered ring system. Examples of monocyclic heteroaryl groups include pyridyl, thienyl, furanyl, pyrrolyl, pyrazolyl, imidazoyl, oxazolyl, isoxazolyl, thiazolyl, isothiazolyl, triazolyl, oxadiazolyl, thiadiazolyl and tetrazolyl. Examples of bicyclic heteroaryl groups include indolyl, benzofuranyl, quinolyl, isoquinolyl indazolyl, indolinyl, isoindolyl, indolizinyl, benzamidazolyl, and quinolinyl.

The term "heteroaryl" also refers to a group in which a heteroaromatic ring is fused to one or more cycloalkyl, or heterocyclyl rings, where the radical or point of attachment is on the heteroaromatic ring. Nonlimiting examples include 5,6,7,8-tetrahydroquinoline and 6,7-dihydro-5H-pyrrolo[3,2-d]pyrimidine.

A heteroaryl group may be mono-, bi-, tri-, or polycyclic, preferably mono-, bi-, or tricyclic, more preferably mono- or bicyclic.

The term "heteroarylalkyl" refers to an heteroaryl group which is linked to another moiety via an alkyl group which may be branched or unbranched. Examples of heteroarylalkyl groups include 2-(pyridin-3-yl)-ethyl, 3-(quinolin-7-yl)-butan-1-yl, and the like.

The term "heteroaryloxy" refers to a heteroaryl group which is linked to another moiety through an oxygen atom, such as pyridin-3-lyoxy.

"Heteroaryl" and "heterocyclyl" is also intended to include oxidized S or N, such as sulfinyl, sulfonyl and N-oxide of tertiary ring nitrogen.

Unless indicated explicitly otherwise, where combinations of groups are referred to herein as one moiety, e.g. arylalkyl, the last mentioned group contains the atom by which the moiety is attached to the rest of the molecule.

An "amino" group as used herein refers to —NH$_2$. The term "N-(alkyl)amino" refers to an amino group in which one hydrogen is replaced by an alkyl group. For example, N—(C$_{1-6}$alkyl)amino refers to an amino group in which one of the hydrogens has been replaced with an alkyl group having from 1 to 6 carbon atoms. The term "N,N-di-(alkyl) amino" refers to an amino group in which both hydrogens have been replaced by an alkyl group which may be the same or different. For example, N,N-di-(C$_{1-6}$alkyl)amino refers to an amino group in which both of the hydrogens have been replaced with an alkyl group which may be the same or different having from 1 to 6 carbon atoms.

A "carbamoyl" group as used herein refers to —C(O)NH$_2$. The term "N-(alkyl)-carbamoyl" refers to a carbamoyl group in which one hydrogen is replaced by an alkyl group. For example, N—(C$_{1-6}$alkyl)-carbamoyl refers to a carbamoyl group in which one of the hydrogens has been replaced with an alkyl group having from 1 to 6 carbon atoms. The term "N,N-di-(alkyl)-carbamoyl" refers to a carbamoyl group in which both hydrogens have been replaced by an alkyl group which may be the same or different. For example, N,N-di-(C$_{1-6}$alkyl)-carbamoyl refers to a carbamoyl group in which both of the hydrogens have been replaced with an alkyl group which may be the same or different having from 1 to 6 carbon atoms.

The term "alkanoyl" refers to a group having the formula —C(O)—R, wherein R is an alkyl group. For example, C$_{1-6}$alkanoyl refers to an alkanoyl group which has from one to six carbon atoms, such as acetyl, isopropyl-carbonyl, and the like.

General

The term "comprising" encompasses "including" as well as "consisting", e.g. a composition "comprising" X may consist exclusively of X or may include something additional, e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x±10%.

Whenever appropriate, terms used in the singular will also include the plural and vice versa.

Unless it is explicitly stated that a group is substituted or may optionally be substituted, it is to be understood that the group is unsubstituted.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

Synthesis

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973.

Salts of compounds of the present invention having at least one salt-forming group may be prepared in a manner known per se. For example, salts of compounds of the present invention having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g. by treating the compounds with an acid or a suitable anion exchange reagent. Internal salts of compounds of the present invention containing acid and basic salt-forming groups, e.g. a free carboxy group and a free amino group, may be formed, e.g. by the neutralisation of salts, such as acid addition salts, to the isoelectric point, e.g. with weak bases, or by treatment with ion exchangers.

Salts can be converted in customary manner into the free compounds; metal and ammonium salts can be converted, for example, by treatment with suitable acids, and acid addition salts, for example, by treatment with a suitable basic agent.

Mixtures of isomers obtainable according to the invention can be separated in a manner known per se into the individual isomers; diastereoisomers can be separated, for example, by partitioning between polyphasic solvent mixtures, recrystallisation and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods, e.g. using chromatographic methods, distribution methods, (re-) crystallization, and the like.

The following applies in general to all processes mentioned hereinbefore and hereinafter.

All the above-mentioned process steps can be carried out under reaction conditions that are known per se, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methycyclohexane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

All starting materials, building blocks, reagents, acids, bases, dehydrating agents, solvents and catalysts utilized to synthesize the compounds of the present invention are either commercially available or can be produced by organic synthesis methods known to one of ordinary skill in the art (Houben-Weyl 4$^{th}$ Ed. 1952, Methods of Organic Synthesis, Thieme, Volume 21).

Typically, the compounds of Formula (I), (I-i), (I-ii), (I-iii), (I-iv), (I-v), (IA), (IIb), (IIc), (IId), (IIe), (IIf), (IIg), (IIh) and (IIi), can be prepared according to the Schemes provided infra.

Method of Preparation

In the following schemes, embodiments of Formula (I) wherein V is $OR^{1b}$ have been illustrated. It is possible to perform many of these reactions with hydrogen or halo V groups so as to obtain the other embodiments of Formula (I) (which are not shown explicitly). Schemes 1-7 describe methods of synthesizing compounds of Formula (I) wherein Y is a direct bond. Scheme 8 describes a method of preparing compounds of Formula (I) wherein Y is O.

Scheme 1:

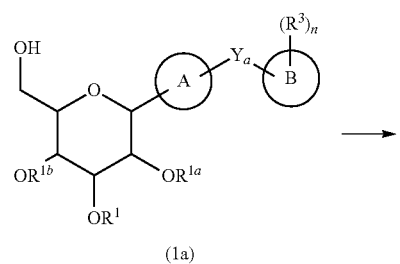

(1a)

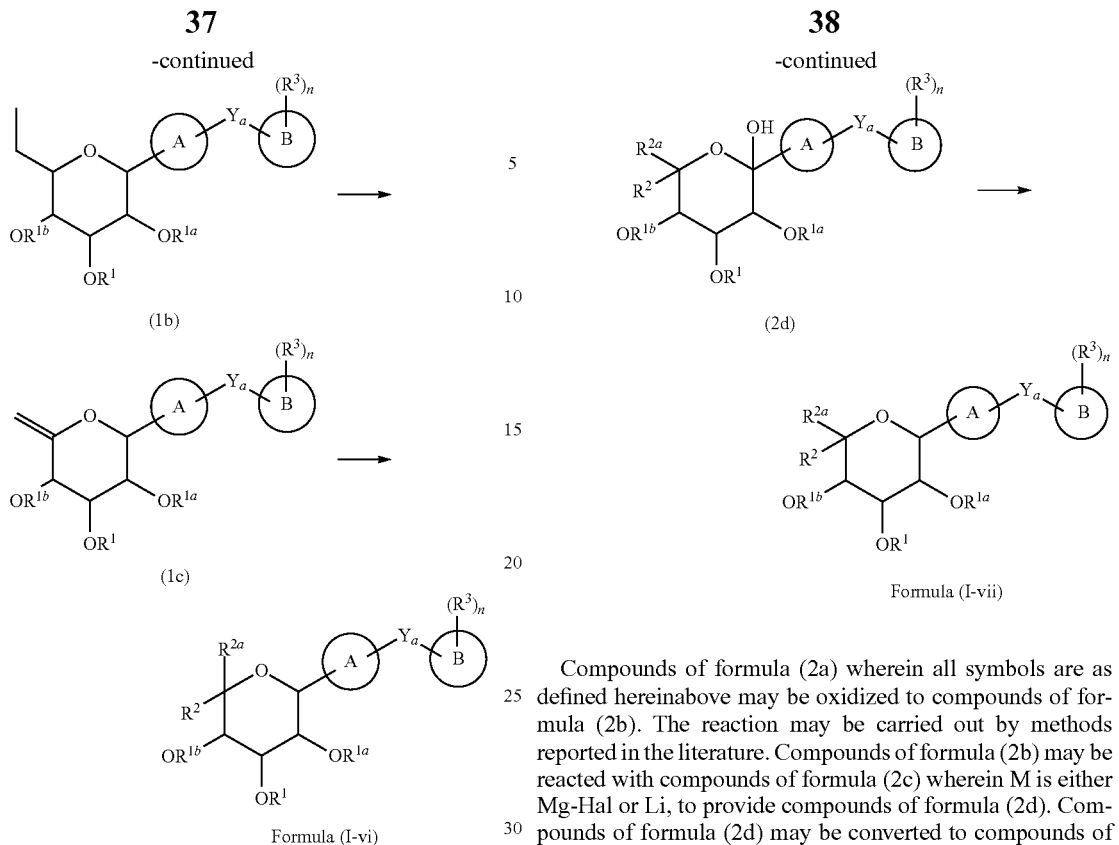

(1b)

(1c)

Formula (I-vi)

Compounds of formula (1a) wherein all symbols are defined hereinabove may be converted to compounds of formula (1b). The reaction may be carried by methods reported in the literature. Compounds of formula (1b) may be dehydrohalogenated in the presence of a base and a solvent to provide compounds of formula (1c). Compounds of formula (1c) may be converted to compounds of Formula (I-vi) wherein $R^{2a}$ and $R^2$ represents a cyclopropyl ring which may be unsubstituted or substituted and all other symbols are as defined herein. Said reaction may be carried out using reagents and conditions well documented in the literature.

Scheme 2:

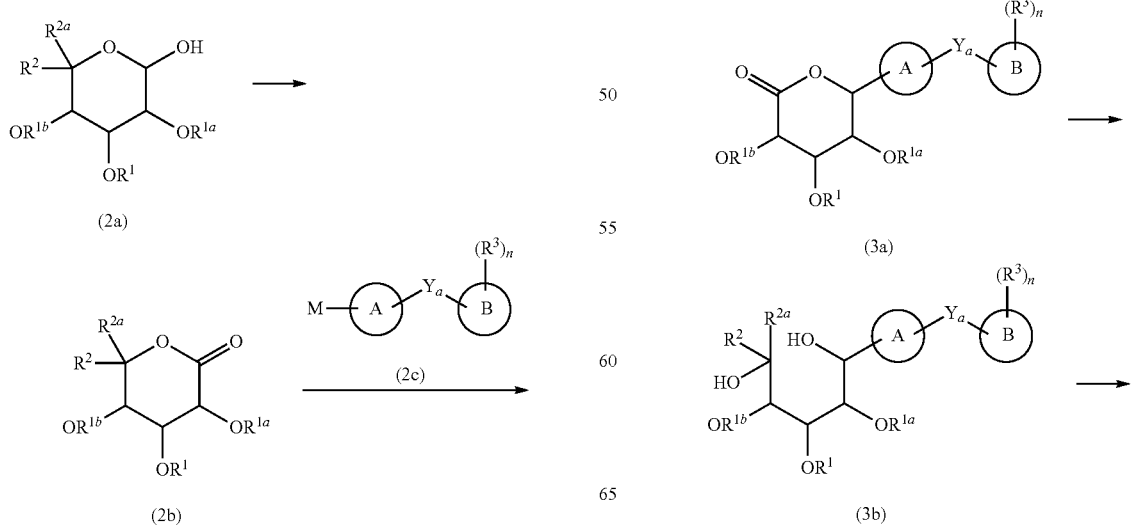

(2a)

(2b)

(2d)

Formula (I-vii)

Compounds of formula (2a) wherein all symbols are as defined hereinabove may be oxidized to compounds of formula (2b). The reaction may be carried out by methods reported in the literature. Compounds of formula (2b) may be reacted with compounds of formula (2c) wherein M is either Mg-Hal or Li, to provide compounds of formula (2d). Compounds of formula (2d) may be converted to compounds of Formula (I-vii), wherein all symbols are as defined hereinabove, by methods reported in the literature.

Scheme 3:

(1c)

(3a)

(3b)

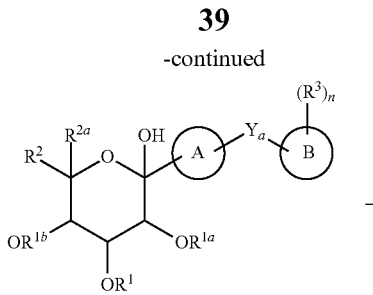

(2d)

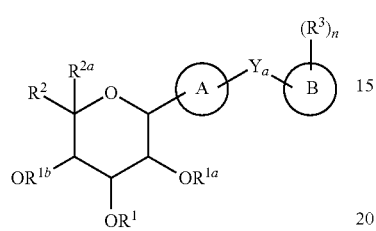

Formula (I-vii)

Compounds of formula (1c) wherein all symbols are defined hereinabove may be converted to compounds of formula (3a). The reaction may be carried under ozonolysis conditions or by dihydroxylation followed by periodate cleavage. Compounds of formula (3a) may be converted to compounds of formula (3b) using corresponding Grignard reagents. Compounds of formula (3b) may be oxidized and cyclized to obtain compounds of formula (2d). Compounds of formula (2d) may be converted to compounds of Formula (I-vii) as described hereinabove.

Scheme 4:

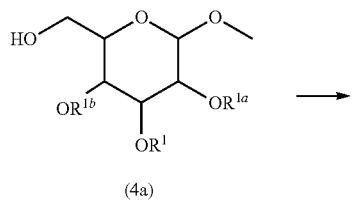

(4a)

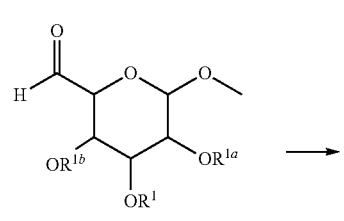

(4b)

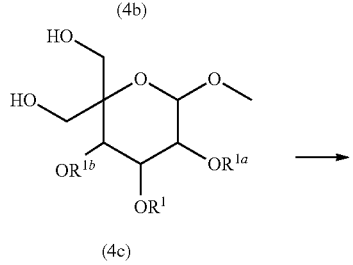

(4c)

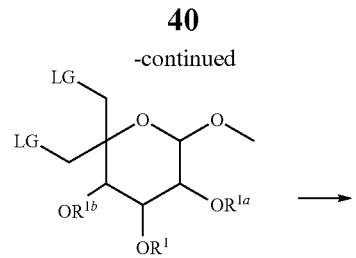

(4d)

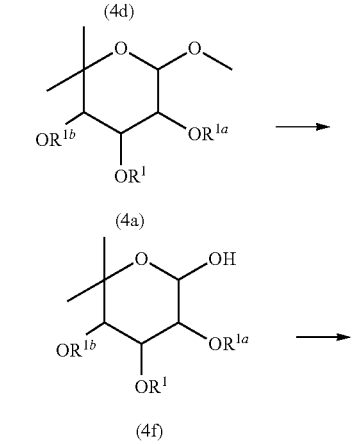

(4e)

(4f)

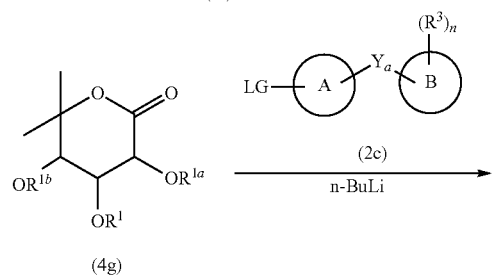

(4g)

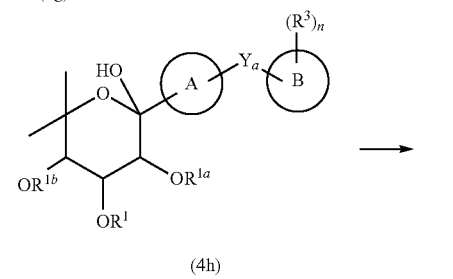

(4h)

Formula (I-viii)

Compounds of formula (4a) wherein all symbols are defined hereinabove may be oxidized to obtain an aldehyde of formula (4b). Compounds of formula (4b) may be converted to bis-hydroxymethyl derivative of formula (4c). Compounds of formula (4c) may be converted to compounds of formula (4d) wherein LG is a leaving group such as halogen, mesyl or tosyl. The compounds of formula (4d) may be converted to compounds of formula (4e) which may be further demethylated to obtain compounds of formula (4f) and oxidized to obtain compounds of formula (4g). Compounds of formula (4g) may be converted to compounds of Formula (I-viii) as described for Scheme 2.

Scheme 5:

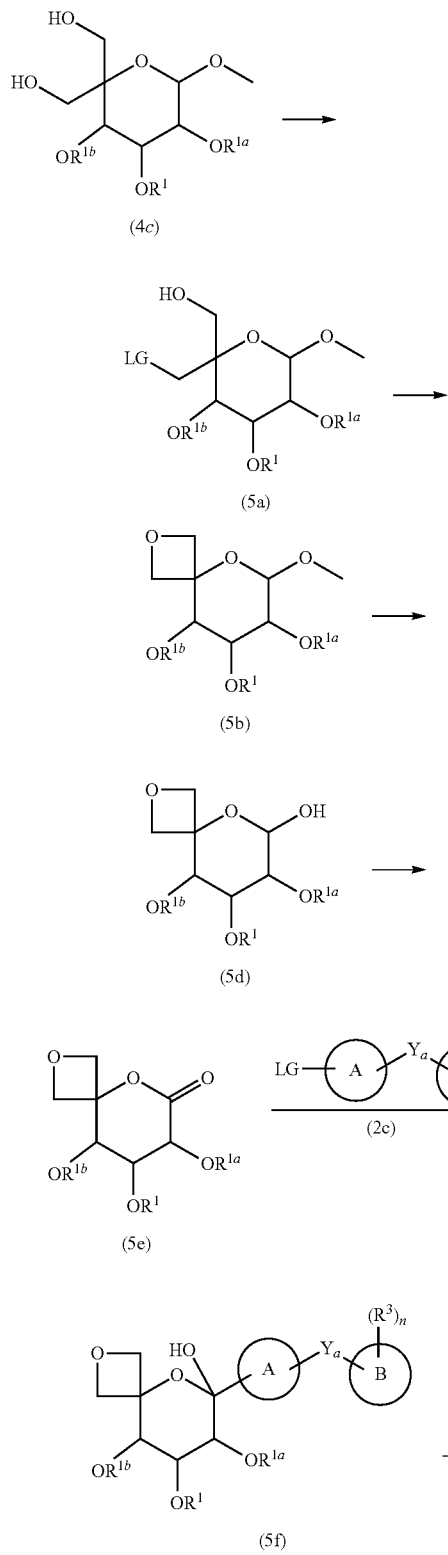

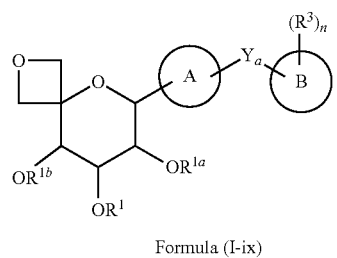

Formula (I-ix)

Compounds of formula (4c) may be selectively converted to compounds of formula (5a) wherein LG is a leaving group such as halogen, mesyl or tosyl and all symbols are defined hereinabove. Compounds of formula (5a) may be cyclized to obtain compounds of formula (5b) which may be demethylated to obtain compounds of formula (5d). Compounds of formula (5d) may be oxidized to obtain compounds of formula (5e). Compounds of formula (5e) may be converted to compounds of Formula (I-ix) as described for Scheme 2.

Scheme 6:

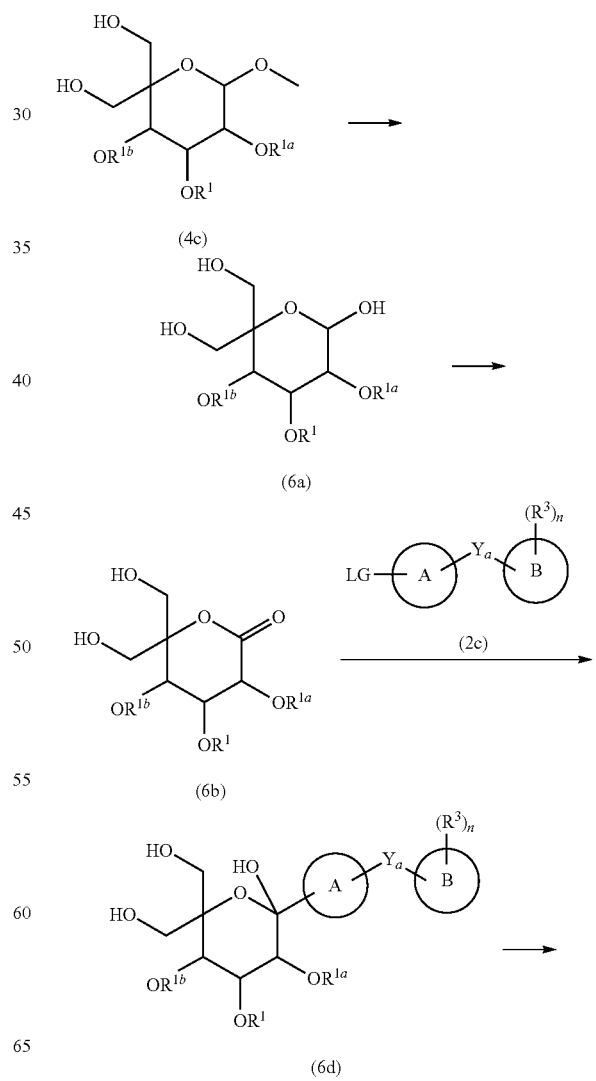

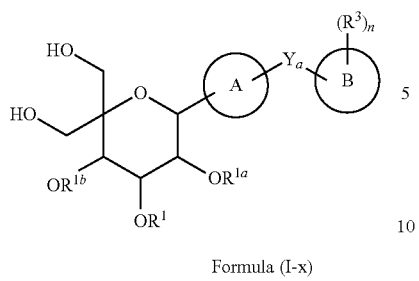

Formula (I-x)

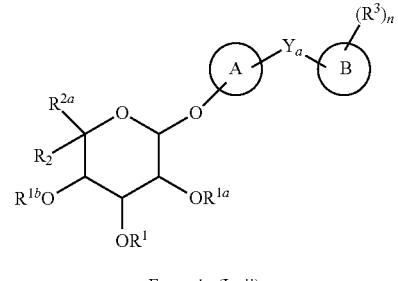

Formula (I-xii)

Compounds of formula (4c) wherein all symbols are defined hereinabove may be demethylated to obtain compounds of formula (6a) and oxidized to obtain compounds of formula (6b). Compounds of formula (6b) may be converted to compounds of Formula (I-x) as described in Scheme 2.

Compounds of formula (7a) wherein all the symbols are as defined hereinabove may be reacted with compounds of formula (7b) wherein all the symbols are as defined hereinabove using reagents for the synthesis of O-glycosides well known in the literature, to provide compounds of Formula (I-xii) wherein there is an oxygen linker between Ring A and the tetrahydropyran ring, and all other symbols are as defined hereinabove.

It will be appreciated that compounds of formula (I) may be prepared by derivatisation of other compounds of formula (I) by transformations well known to those skilled in the art, e.g. functional groups as substitutents on Y may be transformed to different functional groups such as an ester function being converted to an acid, amide, hydroxymethyl, keto, aldehyde as well as an ester. The said conversions may be carried out using reagents and conditions well documented in the literature.

It will be understood that the processes detailed above and elsewhere herein are solely for the purpose of illustrating the invention and should not be construed as limiting. A process utilizing similar or analogous reagents and/or conditions known to one skilled in the art may also be used to obtain a compound of the invention.

Any mixtures of final products or intermediates obtained can be separated on the basis of the physico-chemical differences of the constituents, in a known manner, into the pure final products or intermediates, for example by chromatography, distillation, fractional crystallization, or by the formation of a salt if appropriate or possible under the circumstances.

The following Examples are intended to illustrate the invention and are not to be construed as being limitations thereon. If not mentioned otherwise, all evaporations are performed under reduced pressure. The structure of final products, intermediates and starting materials is confirmed by standard analytical methods, e.g., microanalysis, melting point (m.p.) and spectroscopic characteristics, e.g. MS and NMR. Abbreviations used are those conventional in the art.

Methods for Preparing Aglycons

The following aglycons can be coupled with a sugar using the method described in hereinabove and in the examples.

4-Methyl-3,4-dihydro-2H-benzo[b][1,4]oxazine

Scheme 7:

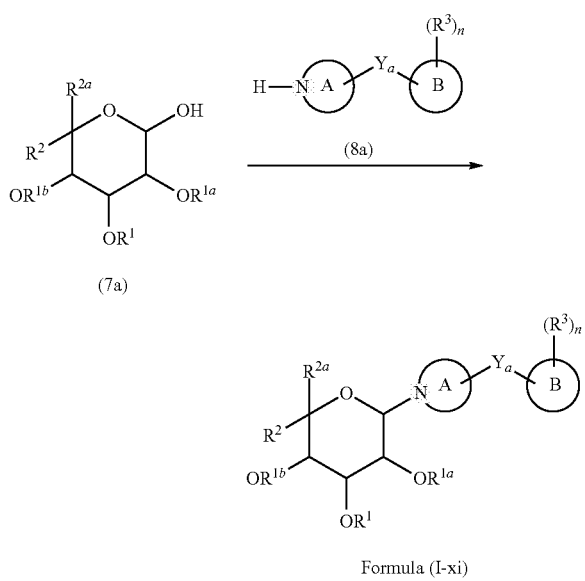

Formula (I-xi)

Compounds of formula (7a) wherein all the symbols are as defined hereinabove may be reacted with compounds of formula (8a) wherein all the symbols are as defined hereinabove, to provide compounds of Formula (I-xi) wherein all symbols are as defined hereinabove.

Scheme 8:

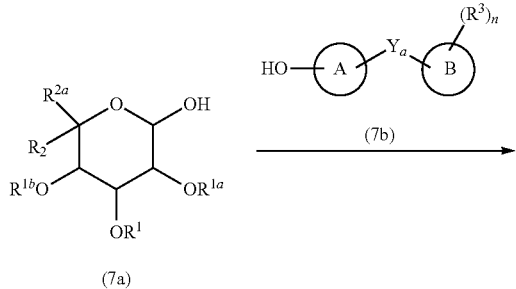

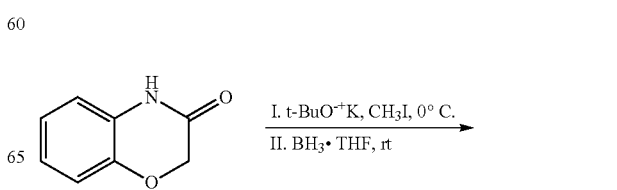

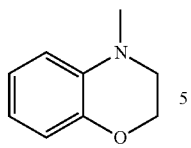

Step I. To a stirred solution of 4H-Benzo[1,4]oxazin-3-one (2.5 g, 16.77 mmol) in DMF (10 mL) was added potassium tert-butoxide (2.81 g, 25.16 mmol) at 0° C. After stirring for 5 min, methyl iodide (3.54 g, 25.16 mmol) was added and the reaction mixture was stirred for another 3 h. The reaction was quenched by addition of water and extracted with ethyl acetate (30×2 ml). The organic layer was washed with water (20 mL), and evaporated to get a crude product 2.2 g.

Step II. To a stirred solution of 4-methyl-4H-benzo[1,4]oxazin-3-one (2.18 g, 13.37 mmol) in THF (5 mL) was added borane-tetrahydrofuran complex (4.02 g, 46.8 mmol) at room temperature. After stirring the solution for 2 h, the reaction mixture was refluxed for 4 h. After complete conversion, reaction mixture was quenched by adding MeOH (10 ml) and evaporated the solvents. The residue obtained was extracted with ethyl acetate (30×2 ml) and the organic layer was washed with water (20 mL), brine (20 mL) and evaporation of solvent gave 4-methyl-3,4-dihydro-2H-benzo[1,4]oxazine 2.0 g.

MS (ES) m/z 150.2 (M+1).

4-Ethyl-3,4-dihydro-2H-benzo[b][1,4]oxazine

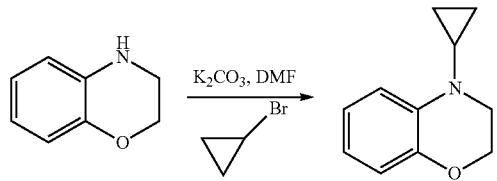

Step I. To a stirred suspension LiAlH₄ (7.6 g, 201 mmol) in THF at 0° C. was added 4H-benzo[1,4]oxazin-3-one (15 g, 100 mmol) in 30 ml of THF and stirred for 4 h at room temperature. After cooling, excess of LiAlH₄ was quenched by the addition of EtOAc followed by aq. NH₄Cl solution. The residue was filtered through a celite bed and usual work up followed by evaporation of the solvent resulted in 3,4-dihydro-2H-benzo[1,4]oxazine (12 g) which was used as such for the next step.

MS (ES) m/z 136 (M+1)

Step II: To a stirred solution of 3,4-dihydro-2H-benzo[1,4]oxazine (4.0 g, 29.6 mmol) in DMF (20 ml) was added potassium carbonate (10.22 g, 74.0 mmol). After stirring for five min. Iodo-ethane (3.5 ml, 44.4 mmol) was added and heated to 60° C. for overnight. Reaction mixture was cooled to room temperature, quenched by the addition of water (20 ml), extracted with ethyl acetate (3×25 ml). The organic layer was washed with water (30 ml), brine (30 ml), dried over sodium sulfate, concentrated and purified by silica gel column chromatography to furnish 4-ethyl-3,4-dihydro-2H-benzo[1,4]oxazine (2.7 g).

¹H NMR (400 MHz, CD₃OD): δ 1.10 (t, J=6.8 Hz, 3H), 3.26-3.33 (m, 4H), 4.16 (t, J=4.4 Hz, 2H), 4.40 (s, 2H), 6.52-6.58 (m, 1H), 6.60-6.80 (m, 3H).

MS (ES) m/z 163.2 (M+1)

4-Cyclopropyl-3,4-dihydro-2H-benzo[b][1,4]oxazine

Step I. To a stirred solution of 3,4-dihydro-2H-benzo[1,4]oxazine (5 g, 37.0 mmol) in DMF (20 mL) was added potassium tert-butoxide (6.22 g, 55.55 mmol) at 0° C. After stirring for 5 min, bromo-cyclopropane (4.44 ml, 55.55 mmol) was added and the reaction mixture was stirred for another 4 h at room temperature. The reaction was quenched by addition of water and extracted with ethyl acetate (50×2 ml). The organic layer was washed with water (20 mL), concentrated and purified by silica gel column chromatography to furnish 4-Cyclopropyl-3,4-dihydro-2H-benzo[1,4]oxazine (4.42 g).

MS (ES) m/z 176 (M+1).

4-Trifluoroacetyl-3,4-dihydro-2,2-dimethyl-2H-benzo[b][1,4]oxazine

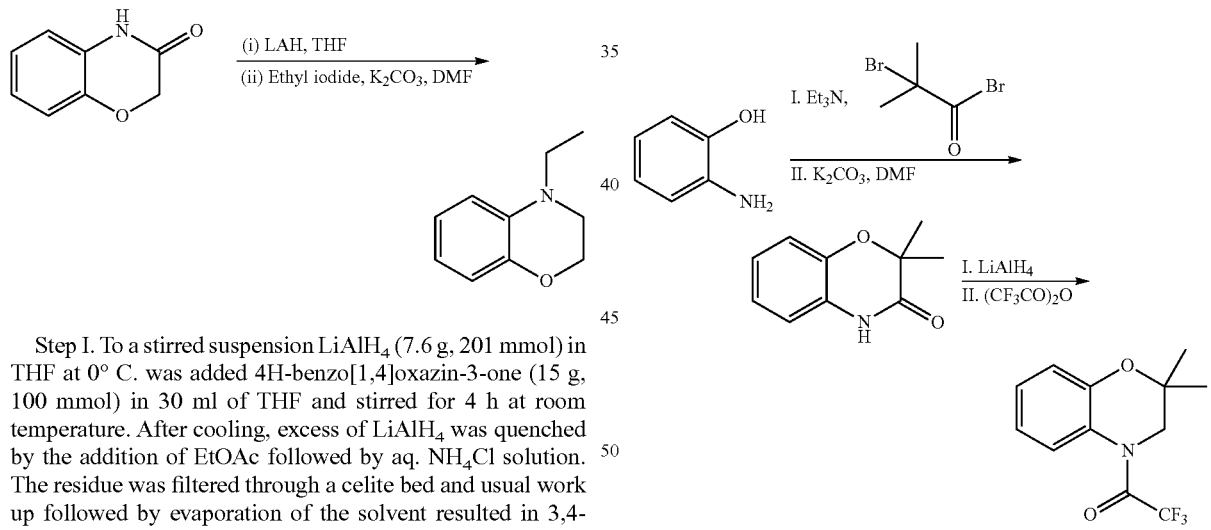

Step I. To a stirred solution of 2-aminophenol (10 g, 9.2 mmol) in DCM (92 ml) at 0° C. was added 2-bromoisobutyryl bromide (11.4 ml, 9.17 mmol) followed by triethyl amine (12.7 ml, 9.2 mmol) and stirred the reaction mixture at 0° C. for 4 h. Reaction mixture was diluted with DCM 100 ml and then washed with water 100 ml dried over sodium sulfate, concentrated on rotavap to give 2-Bromo-N-(2-hydroxy-phenyl)-2-methyl-propionamide (21.8 g) brown solid which was used for next reaction without purification Step II. To a stirred solution of 2-Bromo-N-(2-hydroxyphenyl)-2-methyl-propionamide (21.8 g, 84.4 mmol) in DMF (85 ml) at 25° C. was added potassium carbonate (23.32 g, 168.99 mmol) and stirred the reaction mixture at 80° C. for 4 h. After TLC reaction mixture was filtered through celite and diluted with ethyl acetate 500 ml and then washed with water (100 ml×3), brine (100 ml), dried over anhydrous sodium sulfate, concentrated to give 2,2-dimethyl-4H-benzo[1,4]oxazin-3-one (12.64 g) as brown solid which was purified by column chromatography to furnish 8.5 g pure compound.

MS (EI) m/z 178.2 (M+1)

Step III. To a stirred solution of LAH (3.01 g, 79.10 mmol) in THF (80 ml) at 0° C. was added 2,2-dimethyl-4H-benzo[1,4]oxazin-3-one (7.00 g, 39.5 mmol) in portions and stirred the reaction mixture at 25° C. for 1 h and then 50° C. for 3 h. Reaction mixture was quenched by the addition cold saturated sodium sulfate solution and it was filtered through celite and extracted with DCM (100 ml×2), washed with brine (50 ml), dried over sodium sulfate, concentrated to give 2,2-dimethyl-3,4-dihydro-2H-benzo[1,4]oxazine (6.09 g), which was used as such for the next reaction without purification MS (EI) ink 164.2 (M+1)

Step IV. To a stirred solution of 2,2-dimethyl-3,4-dihydro-2H-benzo[1,4]oxazine (6 g, 36.8 mmol) in DCM (75 ml) at 0° C. was added trifluoroacetic anhydride (6.2 ml, 44.2 mmol) followed by triethyl amine (6.2 ml, 44.2 mmol) and stirred the reaction mixture at 0° C. for 2 h. Reaction mixture was diluted with DCM (100 ml) and then washed with water (100 ml×2), brine (100 ml), dried over anhydrous sodium sulfate, concentrated on to give 1-(2,2-dimethyl-2,3-dihydro-benzo[1,4]oxazin-4-yl)-2,2,2-trifluoro-ethanone (9.46 g) as brown solid which was purified by column chromatography to furnish 8.7 g pure product.

MS (EI) ink 260.2 (M+1)

$^1$H NMR (400 MHz, CDCl$_3$): δ 1.38 (s, 6H), 3.65 (s, 2H), 6.86-6.96 (m, 2H), 7.12-7.16 (m, 1H), 7.97 (d, 1H).

6-Bromo-1-(4-methoxybenzyl)-1,2,3,4-tetrahydro-quinoline

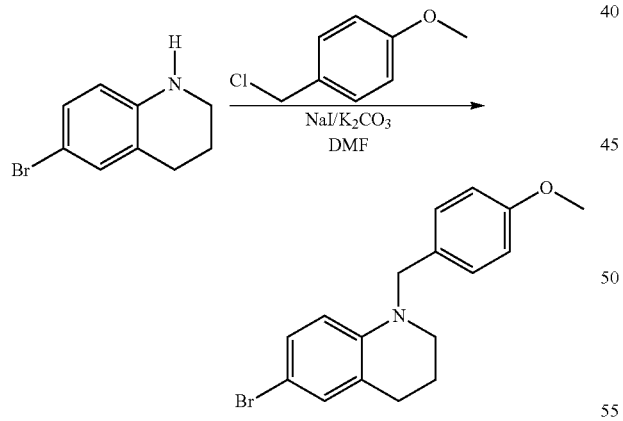

To a stirred solution of 6-bromo-1,2,3,4-tetrahydro-quinoline (3.00 g, 12.1 mmol) in dimethylformamide (25 ml) was added potassium carbonate (3.3 g, 24.1 mmol), sodium iodide (0.905 g, 6.0 mmol) and 4-methoxybenzyl chloride (2.5 ml, 18.1 mmol) and heated at 50° C. After 18 h, reaction mixture was cooled to room temperature and quenched by the addition of water and extracted with ethyl acetate (2×20 ml). The organic layer was washed with water (2×20 mL), brine (20 mL), dried over sodium sulfate, concentrated and purified by the silica gel column chromatography to furnish 6-bromo-1-(4-methoxy-benzyl)-1,2,3,4-tetrahydro-quinoline (2.5 g).

$^1$H NMR (400 MHz, CDCl$_3$): δ 1.96-2.02 (m, 2H), 2.78 (t, J=6.0 Hz, 2H), 3.46 (t, J=5.2 Hz, 2H), 3.80 (s, 3H), 4.40 (s, 2H), 6.38 (d, J=8.4 Hz, 1H), 6.86 (d, J=8.4 Hz, 2H), 7.04 (d, J=8.8 Hz, 1H), 7.07 (s, 1H), 7.15 (d, J=8.4 Hz, 2H).

MS (ES) m/z 332.1, 334.1 (M+1)

EXAMPLES

Examples 1-2

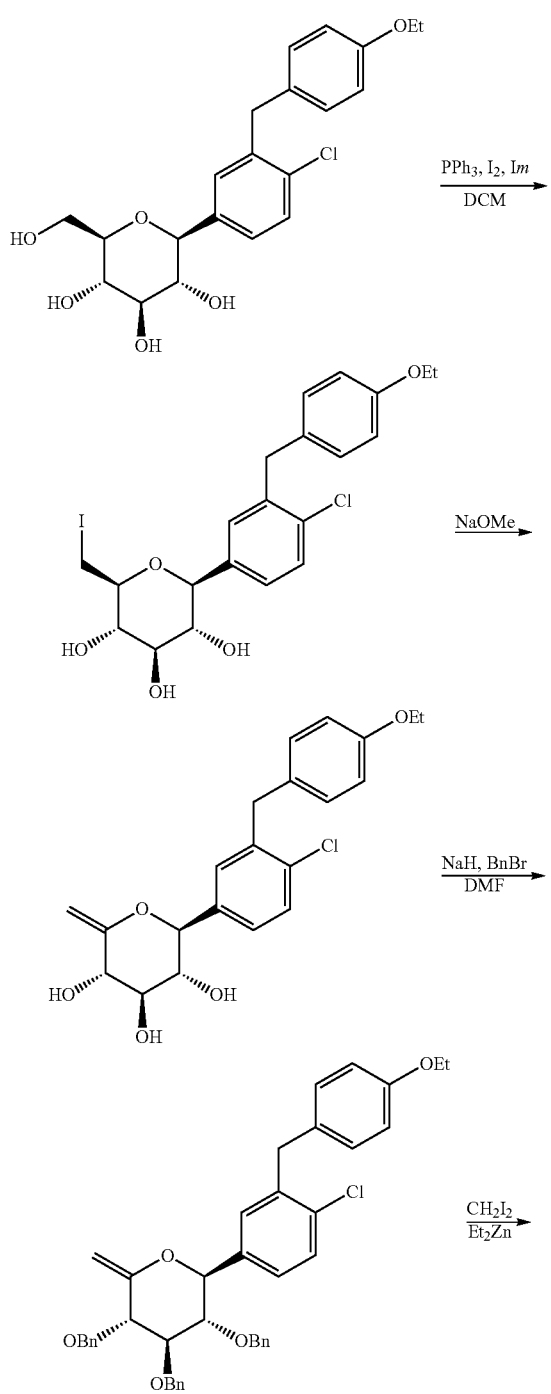

-continued

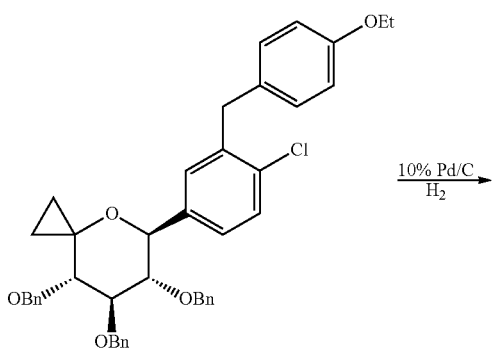

Ex. 1

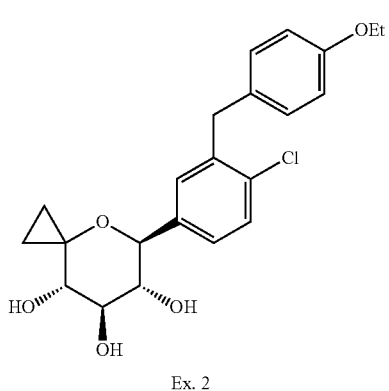

Ex. 2

Step I. To a mixture of (2S,3R,4R,5S,6R)-2-[4-chloro-3-(4-ethoxy-benzyl)-phenyl]-6-hydroxymethyl-tetrahydro-pyran-3,4,5-triol (500 mg, 0.98 mmole) (prepared according to procedure as described in J. Med. Chem. 2008; 51 (5); 1145-1149), $PPh_3$ (3.0 g, 7.3 mmole) and imidazole (650 mg, 9.5 mmole) in 50 mL of dichloromethane (DCM) was added iodine (2.4 g, 9.5 mmole) at 0° C. and refluxed for 18 hrs. The reaction mixture was diluted with water (50 mL) and extracted with dichloromethane (2×200 mL). The crude product obtained after the removal of solvent was purified using silica gel column chromatography (0.5% methanol in DCM) to furnish 3.5 g of (2S,3R,4R,5S,6S)-2-[4-chloro-3-(4-ethoxy-benzyl)-phenyl]-6-iodomethyl-tetrahydro-pyran-3,4,5-triol.

Step II. To a solution of (2S,3R,4R,5S,6S)-2-[4-chloro-3-(4-ethoxy-benzyl)-phenyl]-6-iodomethyl-tetrahydro-pyran-3,4,5-triol (2.5 g, 4.82 mmole) in dry methanol (20 mL), sodium methoxide (2.58 g, 48.2 mmole) was added at 0° C. and stirred at 45° C. for 18 hours. The reaction mixture was diluted with water (50 mL) and extracted with DCM (2×200 mL). The crude product was purified by silica gel column chromatography (1% methanol in DCM) to furnish 1.6 g of (2S,3R,4R,5S)-2-[4-chloro-3-(4-ethoxy-benzyl)-phenyl]-6-methylene-tetrahydro-pyran-3,4,5-triol.

Step III. To a solution of (2S,3R,4R,5S)-2-[4-chloro-3-(4-ethoxy-benzyl)-phenyl]-6-methylene-tetrahydro-pyran-3,4,5-triol (300 mg, 0.77 mmole) in dry DMF (3 mL), sodium hydride (166 mg, 3.46 mmole) was added at 0° C. and stirred at room temperature for 2 hours. Benzyl bromide (0.3 mL, 2.54 mmole), t-butylammoniumiodide (10 mg) was added and reaction mixture stirred at room temperature for 18 hours. The reaction mixture was diluted with water (50 mL) and extracted with DCM (2×200 mL). The crude product was purified by silica gel column chromatography (2% ethylacetate in hexane) to furnish 300 mg of (2S,3S,4R,5S)-3,4,5-tris-benzyloxy-2-[4-chloro-3-(4-ethoxy-benzyl)-phenyl]-6-methylene-tetrahydro-pyran.

$^1$H-NMR (400 M Hz, $CD_3OD$): δ 1.36 (t, J=7.2 Hz, 3H), 3.57 (t, J=9.2 Hz, 1H), 3.72 (t, J=7.2 Hz, 1H), 3.91-3.96 (m, 3H), 4.00 (s, 2H), 4.09 (d, J=6.8 Hz, 1H), 4.34 (d, J=11.2 Hz, 1H), 4.47 (d, J=9.6 Hz, 1H), 4.62-4.70 (m, 4H), 4.88 (d, J=11.2 Hz, 1H), 6.72 (d, J=8.4 Hz, 2H), 6.82 (d, J=7.2 Hz, 2H), 7.03 (d, J=8.4 Hz, 2H), 7.11-7.16 (m, 4H), 7.28-7.38 (m, 13H).

Example 1

(5S,6S,7R,8S)-6,7,8-tris(benzyloxy)-5-(4-chloro-3-(4-ethoxybenzyl)phenyl)-4-oxaspiro[2.5]octane Step IV. To a solution of (2S,3S,4R,5S)-3,4,5-tris-benzyloxy-2-[4-chloro-3-(4-ethoxy-benzyl)-phenyl]-6-methylene-tetrahydro-pyran (150 mg, 0.22 mmole) in dry diethyl ether (3 mL), 1.0M diethylzinc in hexane (1.2 mL, 1.2 mmole), diiodomethane (0.1 mL, 1.2 mmole) was added at room temperature and stirred at 40° C. in sealed vessel for 8 hours. The reaction mixture was diluted with water (20 mL) and saturated aqueous sodium bicarbonate (3 ml) and extracted with DCM (2×30 mL). The crude product was purified by silica gel column chromatography (2% ethyl acetate in hexane) to furnish 105 mg of (5S,6S,7R,8S)-6,7,8-tris-benzyloxy-5-[4-chloro-3-(4-ethoxy-benzyl)-phenyl]-4-oxa-spiro[2.5]octane.

$^1$H-NMR (400 M Hz, $CDCl_3$): δ 0.61-063 (m, 1H), 0.86-0.96 (m, 3H), 1.42 (t, J=6.8 Hz, 3H), 3.35 (t, J=8.8 Hz, 1H), 3.80 (t, J=9.2 Hz, 1H), 3.87 (d, J=9.2 Hz, 1H), 3.96-4.11 (m, 5H), 4.25 (d, J=9.6 Hz, 1H), 4.47 (d, J=10.8 Hz, 1H), 4.6.9 (d, J=11.2 Hz, 1H), 4.89 (t, J=5.6 Hz, 3H), 6.79 (d, J=8.8 Hz, 2H), 6.94 (d, J=6.0 Hz, 2H), 7.07 (d, J=8.4 Hz, 2H), 7.24-7.39 (m, 16H). MS (ES)

Example 2

(5S,6R,7R,8S)-5-[4-Chloro-3-(4-ethoxy-benzyl)-phenyl]-4-oxa-spiro[2.5]octane-6,7,8-triol Step V. To a solution of (5S,6S,7R,8S)-6,7,8-tris-benzyloxy-5-[4-chloro-3-(4-ethoxy-benzyl)-phenyl]-4-oxa-spiro [2.5]octane (70 mg, 0.10 mmole) in methanol (3 mL), 10% Pd/C (45 mg) and 2 drops of con. HCl added and stirred under hydrogen atmosphere at room temperature for 18 hours. The reaction mixture was filtered through celite bed, washed with methanol (20 mL). Crude product was purified by preparative HPLC to furnish 15 mg of the title compound.

$^1$H-NMR (400 M Hz, $CD_3OD$): δ 0.54-0.57 (m, 1H), 0.72-0.75 (m, 1H), 0.84-0.85 (m, 2H), 1.38 (t, J=7.2 Hz, 3H), 3.34-3.49 (m, 2H), 3.85 (d, J=8.8 Hz, 1H), 3.99-4.08 (m, 4H), 4.13 (d, J=9.2 Hz, 1H), 6.82 (d, J=8.4 Hz, 2H), 7.05 (d, J=8.4

Hz, 2H), 7.22 (d, J=158.0 Hz, 1H), 7.26 (s, 1H), 7.35 (d, J=8.0 Hz, 1H). MS (ES) m/z 422 (M+18).

Example 3

(5S,6R,7R,8S)-5-[3-(4-Ethoxy-benzyl)-4-methyl-phenyl]-4-oxa-spiro[2.5]octane-6,7,8-triol

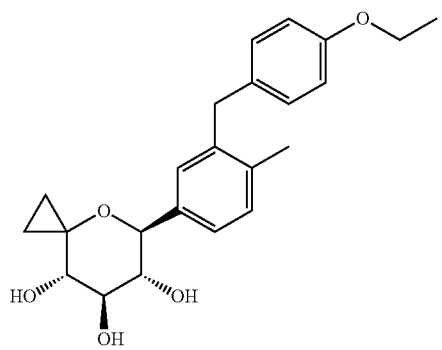 [SMILES: CCOc1ccc(Cc2cc([C@@H]3OC4(CC4)[C@@H](O)[C@H](O)[C@H]3O)ccc2C)cc1]

Prepared following procedure as described for Examples 1-2.

$^1$H-NMR (400 M Hz, CD3OD): δ 0.49-0.58 (m, 1H), 0.70-0.75 (m, 1H), 0.78-0.80 (m, 2H), 1.34 (t, J=6.8 Hz, 3H) 2.15 (s, 3H), 3.41-3.50 (m, 2H), 3.81-3.88 (m, 1H), 3.95 (s, 2H), 3.97-4.05 (m, 2H), 4.07-4.13 (d, J=9.6 Hz, 1H), 6.75 (d, J=7.6 Hz, 2H), 6.98 (d, J=8.0 Hz, 2H), 7.03-7.09 (m, 3H). MS (ES) m/z 402 (M+18).

Examples 4-6

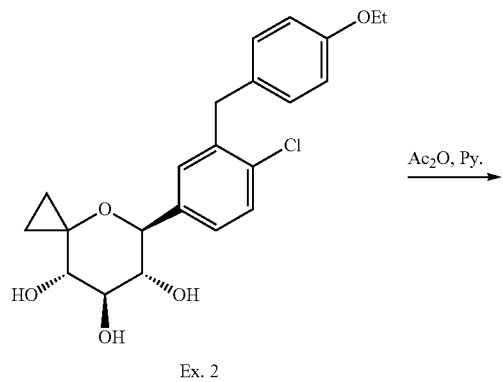

Ex. 2

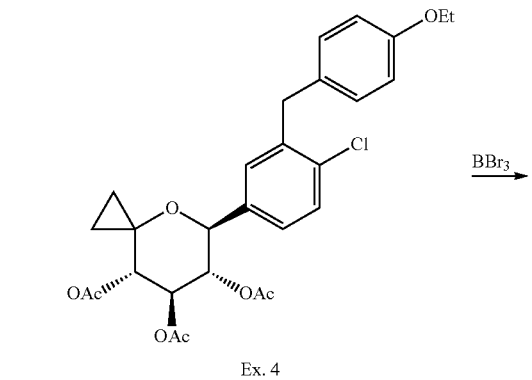

Ex. 4

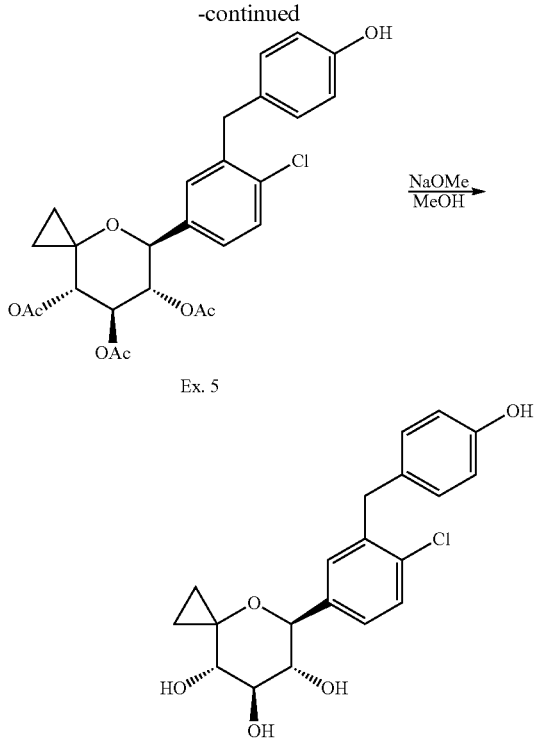

Ex. 5

Ex. 6

Example 4

Acetic acid (5S,6S,7R,8S)-7,8-diacetoxy-5-[4-chloro-3-(4-ethoxy-benzyl)-phenyl]-4-oxa-spiro[2.5]oct-6-yl ester Step 1. To a mixture of (5S,6R,7R,8S)-5-[4-Chloro-3-(4-ethoxy-benzyl)-phenyl]-4-oxa-spiro[2.5]octane-6,7,8-triol (Example 2, 400 mg, 0.99 mmole) pyridine (0.8 mL, 7.9 mmole) and DMAP (2 mg) in dichloromethane (DCM, 10 mL) was added Ac$_2$O (0.7 mL, 7.9 mmole) at room temperature and stirred for overnight. The reaction mixture was diluted with water (20 mL), washed with 1N HCl (10 mL) and extracted with dichloromethane (2×50 mL). The crude product obtained after the removal of solvent was purified using silica gel column chromatography (30% Ethyl acetate in hexane) to furnish 300 mg of Acetic acid (5S,6S,7R,8S)-7,8-diacetoxy-5-[4-chloro-3-(4-ethoxy-benzyl)-phenyl]-4-oxa-spiro[2.5]oct-6-yl ester.

Example 5

Acetic acid (5S,6S,7R,8S)-7,8-diacetoxy-5-[4-chloro-3-(4-hydroxy-benzyl)-phenyl]-4-oxa-spiro[2.5]oct-6-yl ester Step II. To a solution of Acetic acid (5S,6S,7R,8S)-7,8-diacetoxy-5-[4-chloro-3-(4-ethoxy-benzyl)-phenyl]-4-oxa-spiro[2.5]oct-6-yl ester (300 mg, 0.56 mmole) in dry dichloromethane (5 mL), BBr$_3$ (0.54 mL, 5.6 mmole) was added at −78° C. and stirred at −15° C. for 1 hour. The reaction mixture was diluted with diethyl ether (5.0 mL), stirred for 30 min. and further diluted with water (15 mL) and extracted with DCM (2×50 mL) to furnish 280 mg of Acetic acid (5S,6S,7R, 8S)-7,8-diacetoxy-5-[4-chloro-3-(4-hydroxy-benzyl)-phenyl]-4-oxa-spiro[2.5]oct-6-yl ester.

Example 6

(5S,6R,7R,8S)-5-[4-Chloro-3-(4-hydroxy-benzyl)-phenyl]-4-oxa-spiro[2.5]octane-6,7,8-triol Step III. To a solution of Acetic acid (5S,6S,7R,8S)-7,8-diacetoxy-5-[4-chloro-3-(4-hydroxy-benzyl)-phenyl]-4-oxa-spiro[2.5]oct-6-yl ester (60 mg, 0.1 mmole) in dry methanol (3 mL), sodium methoxide (3 mg) was added at room temperature and stirred for overnight. Reaction mixture evaporated to dryness. The crude product was purified by preparative HPLC to furnish 25 mg of (5S,6R,7R,8S)-5-[4-Chloro-3-(4-hydroxy-benzyl)-phenyl]-4-oxa-spiro[2.5]octane-6,7,8-triol.

$^1$H-NMR (400 M Hz, CD3OD): δ 0.41-0.44 (m, 1H), 0.60-0.63 (m, 1H), 0.69-0.72 (m, 2H), 3.20-3.34 (m, 2H), 3.73 (d, J=8.8 Hz, 1H), 3.85 (1/2ABq- J=15.6 Hz, 1H), 3.87 (1/2ABq, J=15.6 Hz, 1H), 4.02 (d, J=9.2 Hz, 1H), 6.58 (d, J=8.4 Hz, 2H), 6.90 (d, J=8.4 Hz, 2H), 7.09 (d, J=8.4 Hz, 1H), 7.21 (s, 1H), 7.22 (d, J=8.0 Hz, 1H). MS (ES) m/z 394 (M+18).

Examples 7 and 8

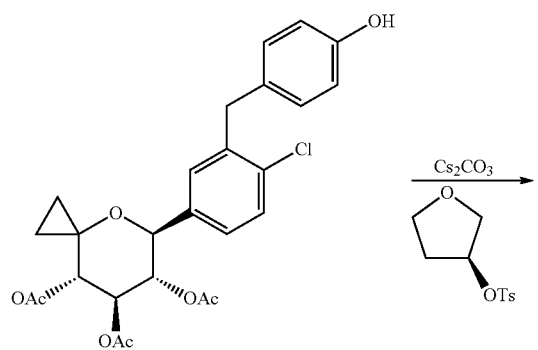
Ex. 5

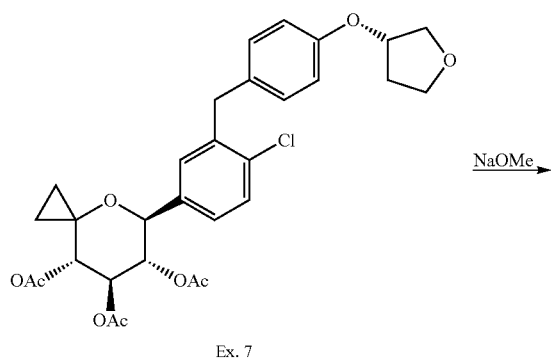
Ex. 7

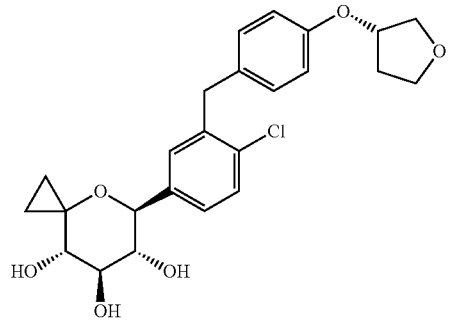
Ex. 8

Example 7

(5S,6S,7R,8S)-5-(4-chloro-3-(4-((S)-tetrahydrofuran-3-yloxy)benzyl)phenyl)-4-oxaspiro[2.5]octane-6,7,8-triyl triacetate Step I. To a solution of Acetic acid (5S,6S,7R,8S)-7,8-diacetoxy-5-[4-chloro-3-(4-hydroxy-benzyl)-phenyl]-4-oxa-spiro[2.5]oct-6-yl ester (120 mg, 0.22 mmole) in DMF (3 mL), cesium carbonate (85 mg, 0.27 mmole), Toluene-4-sulfonic acid (R)-(tetrahydro-furan-3-yl)ester (65 mg, 0.27 mmole) was added at room temperature and heated at 60° C. for 6 hours. The reaction mixture was diluted with water (20 mL), and extracted with dichloromethane (2×50 mL). Crude (5S,6S,7R,8S)-5-(4-chloro-3-(4-((S)-tetrahydrofuran-3-yloxy)benzyl)phenyl)-4-oxaspiro[2.5]octane-6,7,8-triyl triacetate obtained after the removal of solvent used for next step without purification.

Example 8

(5S,6R,7R,8S)-5-(4-Chloro-3-{4-[(S)-(tetrahydrofuran-3-yl)oxy]-benzyl}-phenyl)-4-oxa spiro[2.5]octane-6,7,8-triol Step II. To a solution of above crude product (130 mg, 0.1 mmole) in dry methanol (3 mL), sodium methoxide (6 mg) was added at room temperature and stirred for overnight. Reaction mixture evaporated to dryness. The crude product was purified by preparative HPLC to furnish 25 mg of (5S,6R,7R,8S)-5-(4-Chloro-3-{4-[(S)-(tetrahydro-furan-3-yl)oxy]-benzyl}-phenyl)-4-oxa-spiro[2.5]octane-6,7,8-triol.

$^1$H-NMR (400 M Hz, CD3OD): δ 0.19-0.52 (m, 1H), 0.68-0.70 (m, 1H), 0.78-0.80 (m, 2H), 2.06-2.07 (m, 1H), 2.10-2.18 (m, 1H), 3.26-3.42 (m, 2H), 3.79-3.99 (m, 7H), 4.09 (d, J=9.6 Hz, 1H), 4.90-4.94 (m, 1H), 6.77 (d, J=8.4 Hz, 2H), 7.08 (d, J=8.0 Hz, 2H), 7.18 (d, J=8.0 Hz, 1H), 7.22 (s, 1H), 7.31 (d, J=8.0 Hz, 1H). MS (ES) m/z 447 (M+H).

Examples 9 and 10

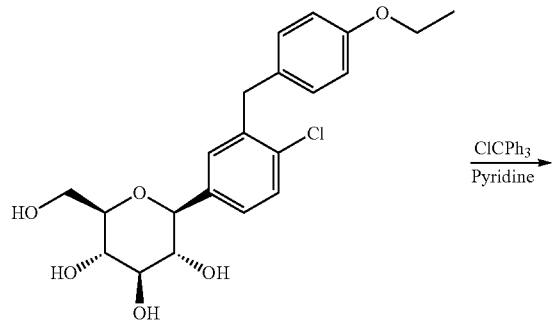

ClCPh₃ / Pyridine

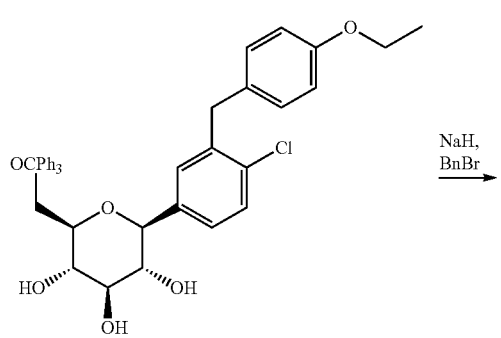

NaH, BnBr

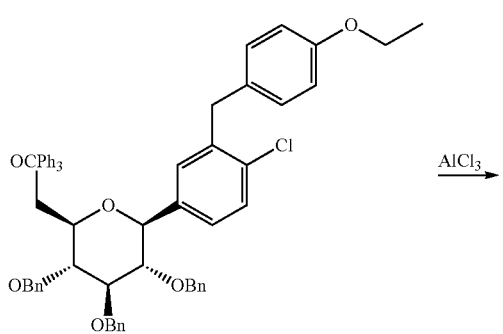

AlCl₃

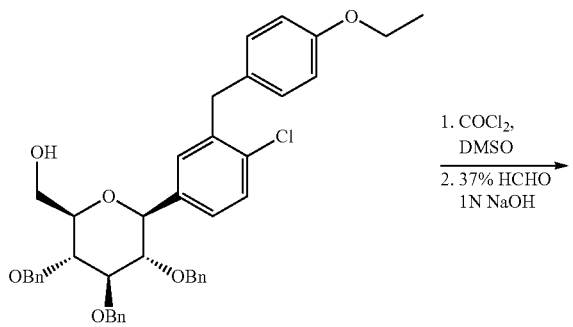

1. COCl₂, DMSO
2. 37% HCHO, 1N NaOH

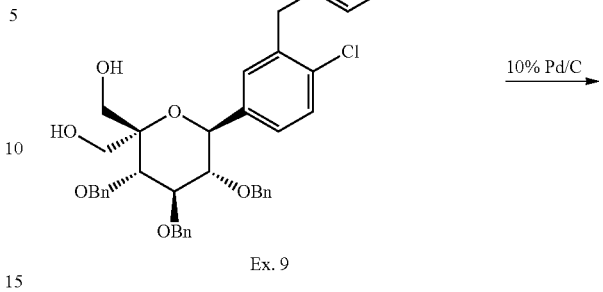

10% Pd/C

Ex. 9

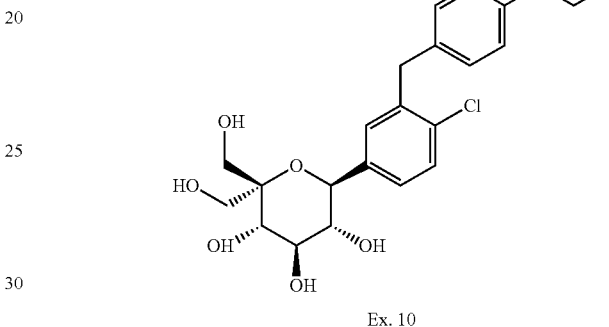

Ex. 10

Step I. To a mixture of (2S,3R,4R,5S,6R)-2-[4-chloro-3-(4-ethoxy-benzyl)-phenyl]-6-hydroxymethyl-tetrahydro-pyran-3,4,5-triol (7.0 g, 17.1 mmole) (prepared according to procedure as described in J. Med. Chem. 2008; 51 (5); 1145-1149), trityl chloride (5.2 g, 18.8 mmole) in pyridine (50 mL) was added at room temperature and refluxed for 18 hrs. The excess pyridine was evaporated; reaction mixture was diluted with water (250 mL) and washed with 1N dil. HCl (50 mL) extracted with dichloromethane (2×200 mL). The crude product obtained after the removal of solvent was purified using silica gel column chromatography (0.5% methanol in DCM) to furnish 9.8 g of (2S,3R,4R,5S,6R)-2-[4-Chloro-3-(4-ethoxy-benzyl)-phenyl]-6-trityloxymethyl-tetrahydro-pyran-3,4,5-triol.

Step II. To a solution of (2S,3R,4R,5S,6R)-2-[4-Chloro-3-(4-ethoxy-benzyl)-phenyl]-6-trityloxymethyl-tetrahydro-pyran-3,4,5-triol (9.8 g, 15 mmole) in dry DMF (50 mL), sodium hydride (3.2 g, 67.8 mmole) was added at 0° C. and stirred at room temperature for 2 hours. Benzyl bromide (5.9 mL, 49.7 mmole), TBAI (500 mg) were added and the reaction mixture stirred at room temperature for 18 hours. The reaction mixture was diluted with water (500 mL) and extracted with DCM (2×500 mL). The crude product obtained after removal of solvent to furnish 12.3 g of (2S,3S,4R,5R,6R)-3,4,5-Tris-benzyloxy-2-[4-chloro-3-(4-ethoxy-benzyl)-phenyl]-6-trityloxymethyl-tetrahydro-pyran.

Step III. To a solution of (2S,3S,4R,5R,6R)-3,4,5-Tris-benzyloxy-2-[4-chloro-3-(4-ethoxy-benzyl)-phenyl]-6-trityloxymethyl-tetrahydro-pyran (12.2 g, 17.9 mmole) in dry DCM (50 mL), AlCl₃ (2.8 gm, 21.5 mmole) in diethyl ether was added at 0° C. and stirred at room temperature for 2 hours. The reaction mixture was diluted with water (500 mL) and saturated aqueous NaHCO₃ (50 mL), extracted with DCM (2×250 mL). The crude product obtained after the removal of solvent was purified using silica gel column chromatography (10% ethyl acetate in hexane) to furnish 6.1 g of {(2R,3R,4R,5S,6S)-3,4,5-Tris-benzyloxy-6-[4-chloro-3-(4-ethoxy-benzyl)-phenyl]-tetrahydro-pyran-2-yl}-methanol.

Example 9

((3S,4R,5S,6S)-3,4,5-tris(benzyloxy)-6-(4-chloro-3-(4-ethoxybenzyl)phenyl)tetrahydro-2H-pyran-2,2-dlyl)dimethanol Step IV. To a solution of oxallyl chloride (0.05 mL, 0.72 mmole) in dry DCM (5 mL), DMSO (0.1 mL, 1.43 mmole) in DCM (1 mL) was added at −70° C. and stirred for 10 min., Solution of {(2R,3R,4R,5S,6S)-3,4,5-Tris-benzyloxy-6-[4-chloro-3-(4-ethoxy-benzyl)-phenyl]-tetrahydro-pyran-2-yl}-methanol (500 mg, 0.72 mmole) in DCM (4 mL) was added during 15 min at −70° C. and the reaction mixture stirred for 1 hour. Triethylamine (0.5 mL, 3.5 mmole) was added and allowed to stir at room temperature for 15 min. The reaction mixture was diluted with water (25 mL) and extracted with DCM (2×25 mL). The combined organic layer washed with 1N HCl (10 mL), saturated aqueous NaHCO$_3$ (10 mL), The crude product obtained after the removal of solvent was co evaporated with toluene (20×4) to furnish crude aldehyde. To this crude aldehyde 1-4 dioxane (10 mL), 1N NaOH (2 mL), 37% aq. HCHO (2 mL) were added and stirred for 72 hours at room temperature. The reaction mixture was diluted with water (25 mL) and neutralized with 1N HCl, extracted with ethyl acetate (2×25 mL). The crude product obtained after the removal of solvent was purified using silica gel column chromatography (20% ethyl acetate in hexane) to furnish 210 mg of {(3S,4R,5S,6S)-3,4,5-Tris-benzyloxy-6-[4-chloro-3-(4-ethoxy-benzyl)-phenyl]-2-hydroxymethyl-tetrahydro-pyran-2-yl}-methanol

Example 10

(3S,4R,5R,6S)-6-[4-Chloro-3-(4-ethoxy-benzyl)-phenyl]-2,2-bis-hydroxymethyl-tetrahydro-pyran-3,4,5-triol Step V. To a solution of {(3S,4R,5S,6S)-3,4,5-Tris-benzyloxy-6-[4-chloro-3-(4-ethoxy-benzyl)-phenyl]-2-hydroxymethyl-tetrahydro-pyran-2-yl}-methanol (125 mg, 0.16 mmole) in methanol (3 mL), 10% Pd/C (65 mg) and 2 drops of con. HCl were added and stirred under hydrogen atmosphere at room temperature for 18 hours. The reaction mixture was filtered through cetlie bed, washed with methanol (20 mL). The crude product was purified by preparative HPLC to furnish 25 mg of (3S,4R,5R,6S)-6-[4-Chloro-3-(4-ethoxy-benzyl)-phenyl]-2,2-bis-hydroxymethyl-tetrahydro-pyran-3,4,5-triol.

$^1$H-NMR (400 M Hz, CD3OD): δ 1.35 (t, J=6.8 Hz, 3H), 3.24 (1, J=9.2 Hz, 1H), 3.67-3.79 (m, 5H), 3.95-4.03 (m, 5H), 4.46 (d, J=9.6 Hz, 1H), 6.78 (d, J=8.4 Hz, 2H), 7.09 (d, J=8.4 Hz, 2H), 7.33-7.37 (m, 3H), MS (ES) m/z 456 (M+18).

Example 11

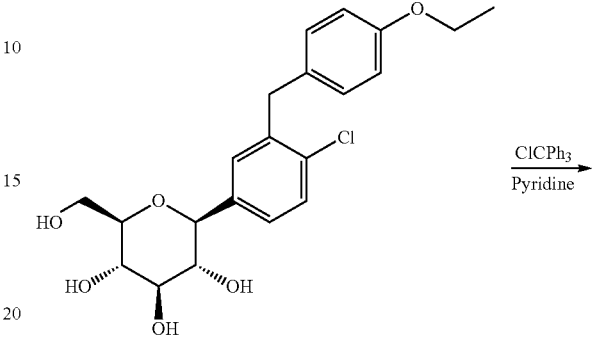

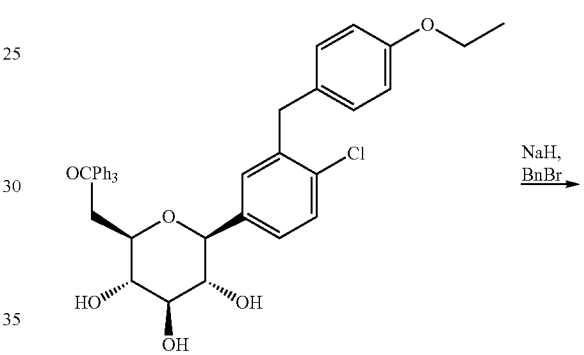

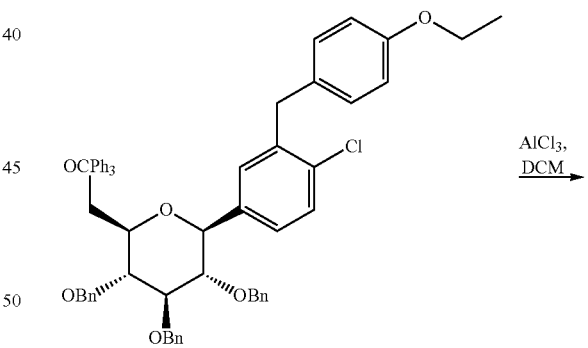

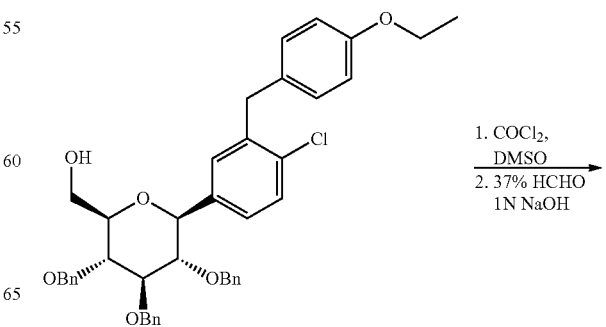

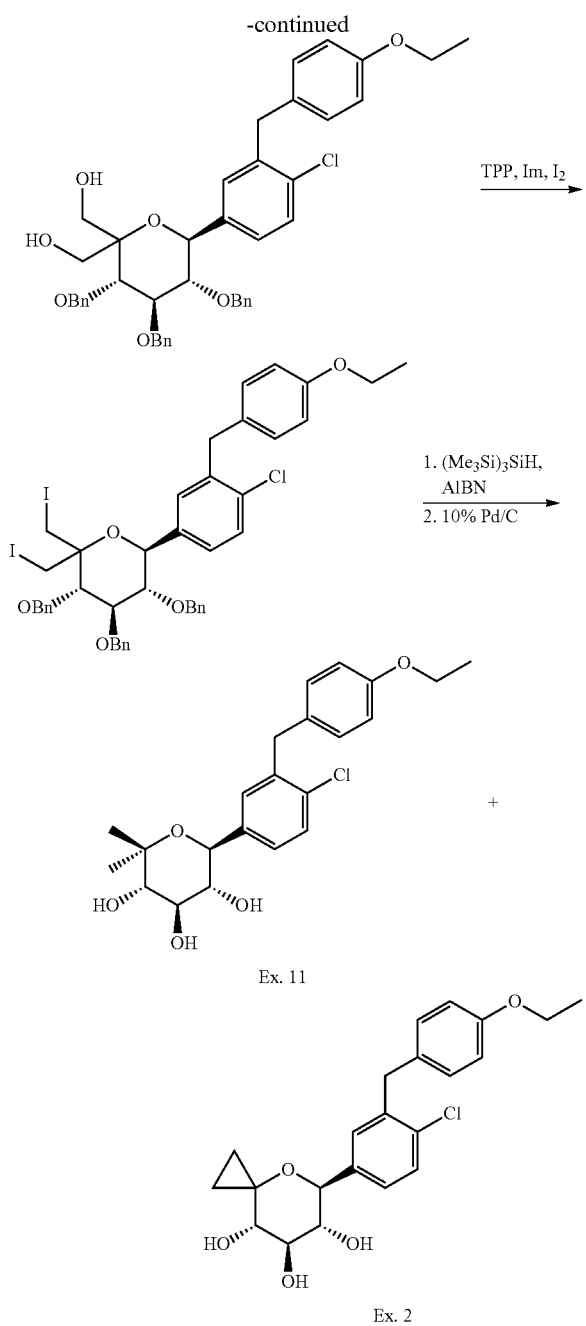

Ex. 11

Ex. 2

Step 1. To a mixture of (2S,3R,4R,5S,6R)-2-[4-chloro-3-(4-ethoxy-benzyl)-phenyl]-6-hydroxymethyl-tetrahydro-pyran-3,4,5-triol (7.0 g, 17.1 mmole, prepared according to procedure described in J. Med. Chem. 2008; 51 (5); 1145-1149), trityl chloride (5.2 g, 18.8 mmole) in pyridine (50 mL) was added at room temperature and heated at 80° C. for 18 hrs. The excess pyridine was evaporated, reaction mixture was diluted with water (250 mL), washed with 1N dil. HCl (50 mL) extracted with dichloromethane (2×200 mL). The crude product obtained after the removal of solvent was purified using silica gel column chromatography (0.5% methanol in DCM) to furnish 9.8 g of (2S,3R,4R,5S,6R)-2-[4-Chloro-3-(4-ethoxy-benzyl)-phenyl]-6-trityloxymethyl-tetrahydro-pyran-3,4,5-triol.

Step II. To a solution of (2S,3R,4R,5S,6R)-2-[4-Chloro-3-(4-ethoxy-benzyl)-phenyl]-6-trityloxymethyl-tetrahydro-pyran-3,4,5-triol (9.8 g, 15 mmole) in dry DMF (50 mL), sodium hydride (3.2 g 50% in oil, 67.8 mmole) was added at 0° C. and stirred at room temperature for 2 hours. Benzyl bromide (5.9 mL, 49.7 mmole), tetrabutylammoniuliodide (500 mg) added and the reaction mixture stirred at room temperature for 18 hours. The reaction mixture was diluted with water (500 mL) and extracted with DCM (2×500 mL). The crude product obtained after removal of solvent to furnish 12.3 g of (2S,3S,4R,5R,6R)-3,4,5-tris-benzyloxy-2-[4-chloro-3-(4-ethoxy-benzyl)-phenyl]-6-trityloxymethyl-tetrahydro-pyran.

Step III. To a solution of (2S,3S,4R,5R,6R)-3,4,5-tris-benzyloxy-2-[4-chloro-3-(4-ethoxy-benzyl)-phenyl]-6-trityloxymethyl-tetrahydro-pyran (12.2 g, 17.9 mmole) in dry DCM (50 mL), AlCl₃ (2.8 g, 21.5 mmole) in diethyl ether was added at 0° C. and stirred at room temperature for 2 hours. The reaction mixture was diluted with water (500 mL) and saturated aqueous NaHCO₃ (50 mL), extracted with DCM (2×250 mL). The crude product obtained after the removal of solvent was purified using silica gel column chromatography (10% ethyl acetate in hexane) to furnish 6.1 g of ({2R,3R,4R,5S,6S)-3,4,5-tris-benzyl oxy-6-[4-chloro-3-(4-ethoxy-benzyl)-phenyl]-tetrahydro-pyran-2-yl}-methanol.

Step IV. To a solution of oxalyl chloride (0.05 mL, 0.718 mmole) in dry DCM (5 mL), DMSO (0.1 mL, 1.43 mmole) in DCM (1 mL) was added at -70° C. and stirred for 10 min., Solution of {(2R,3R,4R,5S,6S)-3,4,5-tris-benzyloxy-6-[4-chloro-3-(4-ethoxy-benzyl)-phenyl]-tetrahydro-pyran-2-yl}-methanol (500 mg, 0.718 mmole) in DCM (4 mL) was added during 15 min at -70° C. and reaction mixture stirred for 1 hour. Triethylamine (0.5 mL, 3.5 mmole) was added and allowed stir at room temperature for 15 min. The reaction mixture was diluted with water (25 mL) and the organic layer washed with 1N HCl (10 mL), saturated aqueous NaHCO₃ (10 mL), extracted with DCM (2×25 mL). The crude product obtained after the removal of solvent was co evaporated with toluene (20×4) to furnish crude aldehyde. To this crude aldehyde, 1-4 dioxane (10 mL), 1N NaOH (2 mL), 37% aq. formaldehyde (2 mL) were added and stirred for 72 hours at room temperature. The reaction mixture was diluted with water (25 mL) and washed with 1N HCl (15 mL), extracted with ethyl acetate (2×25 mL). The crude product obtained after the removal of solvent was purified using silica gel column chromatography (20% ethyl acetate in hexane) to furnish 210 mg of {(3S,4R,5S,6S)-3,4,5-tris-benzyloxy-6-[4-chloro-3-(4-ethoxy-benzyl)-phenyl]-2-hydroxymethyl-tetrahydro-pyran-2-yl}-methanol.

Step V. To a solution of {(3S,4R,5S,6S)-3,4,5-tris-benzyloxy-6-[4-chloro-3-(4-ethoxy-benzyl)-phenyl]-2-hydroxymethyl-tetrahydro-pyran-2-yl}-methanol (250 mg, 0.35 mmole) in toluene (15 mL), triphenylphosphine (460 mg, 1.7 mmole), imidazole (120 mg, 1.7 mmole), iodine (440 mg, 1.7 mmole) was added and stirred at 80° C. for 8 hour. The reaction mixture was diluted water (25 mL) and washed with aqueous sodium thiosulfate and extracted with Ethyl acetate (2×50 mL) The crude product obtained after the removal of solvent was purified using silica gel column chromatography (10% ethyl acetate in hexane) to furnish 200 mg of (3S,4R,5S,6S)-3,4,5-tris-benzyloxy-6-[4-chloro-3-(4-ethoxy-benzyl)-phenyl]-2,2-bis-iodomethyl-tetrahydro-pyran.

Step VI. To a solution of (3S,4R,5S,6S)-3,4,5-tris-benzyloxy-6-[4-chloro-3-(4-ethoxy-benzyl)-phenyl]-2,2-bis-iodomethyl-tetrahydro-pyran (100 mg, 0.10 mmole) in toluene (2 mL), tristrimethylsilllylsilane (0.1 mL), AIBN (12 mg) was added and heated at 120° C. for 24 hour in a sealed tube. The reaction mixture was diluted with methanol and evaporated, washed with water (10 mL) and extracted with Ethyl acetate (3×15 mL). The crude product obtained after the removal of solvent to furnish 100 mg of crude (3S,4R,5S,6S)-3,4,5-tris-benzyloxy-6-[4-chloro-3-(4-ethoxy-benzyl)-phenyl]-2,2-dimethyl-tetrahydro-pyran.

Example 11

(3S,4R,5R,6S)-6-[4-chloro-3-(4-ethoxy-benzyl)-phenyl]-2,2-dimethyl-tetrahydro-pyran-3,4,5-triol Step VII. To the above crude mixture of (3S,4R,5S,6S)-3,4,5-tris-benzyloxy-6-[4-chloro-3-(4-ethoxy-benzyl)-phenyl]-2,2-dimethyl-tetrahydro-pyran (~100 mg, 0.14 mmole) in methanol (3 mL), 10% Pd/C (100 mg) and 2 drops of con. HCl added and stirred under hydrogen atmosphere at room temperature for 18 hours. The reaction mixture was filtered through cetlie bed, washed with methanol (20 mL). The crude product was purified by preparative chiral HPLC to furnish 10 mg of (3S,4R,5R,6S)-6-[4-chloro-3-(4-ethoxy-benzyl)-phenyl]-2,2-dimethyl-tetrahydro-pyran-3,4,5-triol (Ex. 11) and 20 mg of (5S,6R,7R,8S)-5-[4-chloro-3-(4-ethoxy-benzyl)-phenyl]-4-oxa-spiro[2.5]octane-6,7,8-triol (Ex. 2).

$^{1}$H-NMR (400 M Hz, DMSO-D6): δ 1.093 (s, 3H), 1.12 (s, 3H), 1.25 (t, J=7.2 Hz, 3H), 2.97-3.03 (m, 2H), 3.33-3.90 (m, 1H), 3.89-3.97 (m, 4H), 4.13 (d, J=9.6 Hz, 1H), 4.75 (d, J=6.0 Hz, 1H), 4.81 (d, J=4.4 Hz, 1H), 4.96 (d, J=4.4 Hz, 1H), 6.79 (d, J=8.8 Hz, 2H), 7.04 (d, J=8.8 Hz, 2H), 7.15 (dd, J=2 Hz, J=8.4 Hz, 1H), 7.24 (d, J=8.4 Hz, 1H), 7.31 (d, J=8.0 Hz, 1H). MS (ES) m/z 424 (M+18).

Examples 12-15

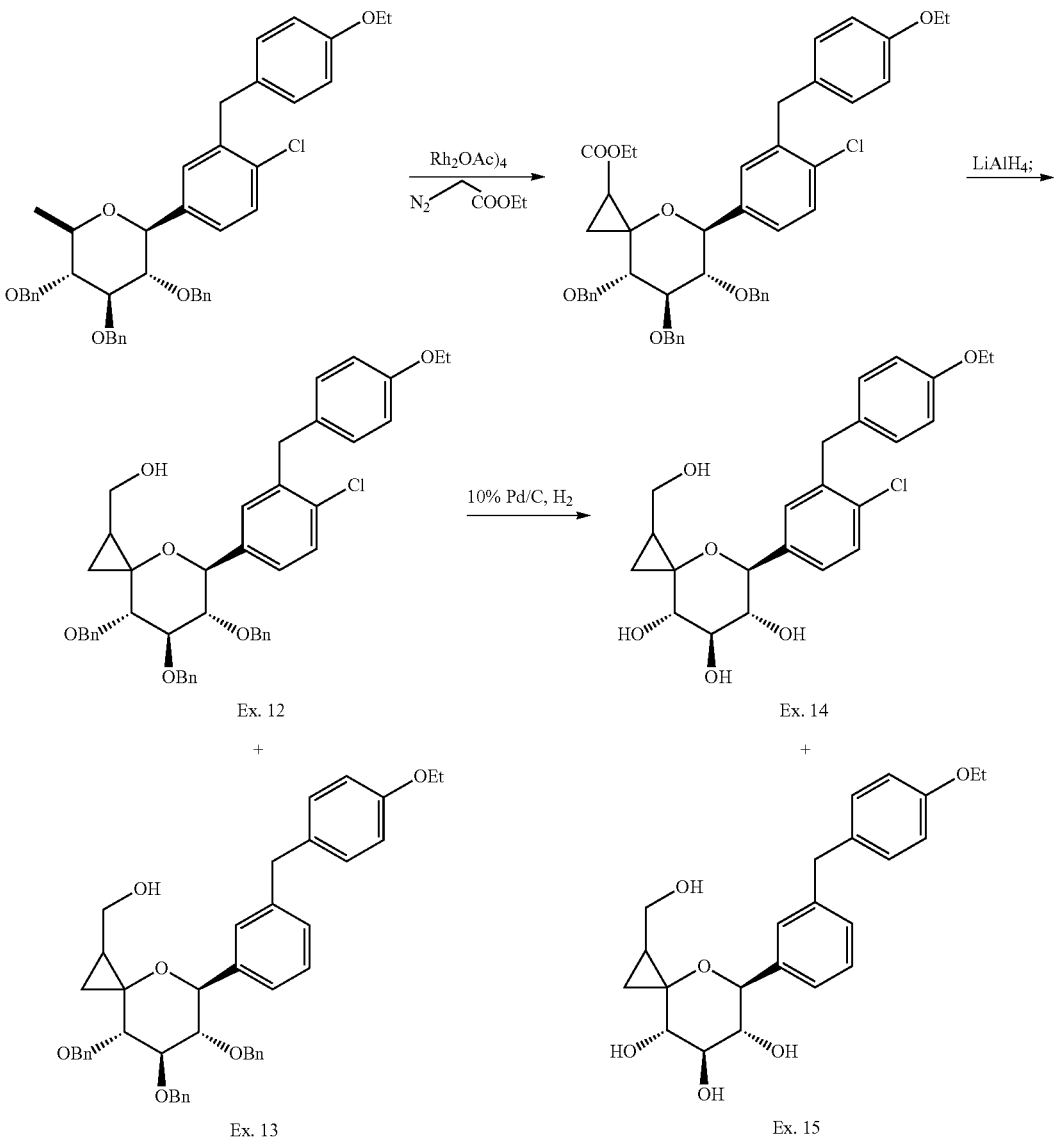

Step 1. To a solution of (2S,3S,4R,5S)-3,4,5-tris-benzyloxy-2-[4-chloro-3-(4-ethoxy-benzyl)-phenyl]-6-methylene-tetrahydro-pyran (See Ex. 1, step III, 100 mg, 0.15 mmole) and rhodium acetate dimmer (0.13 mg, 0.002 mmole)

in dry dichloromehane (5 mL), ethyl diazoacetate in dichloromethane (2 mL) was added during 3 hours at room temperature and stirred for 18 hours. The reaction mixture was diluted with water (20 mL) and extracted with DCM (2×30 mL). The crude product was purified by silica gel column chromatography (20% ethyl acetate in hexane) to furnish 50 mg of (5S,6S,7R,8S)-6,7,8-tris-benzyloxy-5-[4-chloro-3-(4-ethoxy-benzyl)-phenyl]-4-oxa-spiro[2.5]octane-1-carboxylic acid ethyl ester.

Example 12

{(5S,6S,7R,8S)-6,7,8-Tris-benzyloxy-5-[4-chloro-3-(4-ethoxy-benzyl)-phenyl]-4-oxa-spiro[2.5]oct-1-yl}-methanol; and Example {(5S,6S,7R,8S)-6,7,8-Tris-benzyloxy-5-[3-(4-ethoxy-benzyl)-phenyl]-4-oxa-spiro[2.5]oct-1-yl}-methanol Step II. To a solution of (5S,6S,7R,8S)-6,7,8-tris-benzyloxy-5-[4-chloro-3-(4-ethoxy-benzyl)-phenyl]-4-oxa-spiro[2.5]octane-1-carboxylic acid ethyl ester (350 mg, 0.46 mmole) in dry tetrahydrofuran (5 mL), lithium aluminium hydride (36 mg, 9.3 mmole) was added at 0° C. and stirred for 4 hours. The excess lithium aluminium hydride was decomposed by adding saturated aqueous sodium sulfate and extracted with Ethyl acetate (3×15 mL). The crude product obtained after the removal of solvent furnished 300 mg mixture of {(5S,6S,7R,8S)-6,7,8-Tris-benzyloxy-5-[4-chloro-3-(4-ethoxy-benzyl)-phenyl]-4-oxa-spiro[2.5]oct-1-yl}-methanol and {(5S,6S,7R,8S)-6,7,8-Tris-benzyloxy-5-(3-[4-ethoxy-benzyl)-phenyl]-4-oxa-spiro[2.5]oct-1-yl}-methanol.

Example 14

(5S,6R,7R,8S)-5-[4-Chloro-3-(4-ethoxy-benzyl)-phenyl]-1-hydroxymethyl-4-oxa-spiro[2.5]octane-6,7,8-triol; and Example 15

(5S,6R,7R,8S)-5-[3-(4-Ethoxy-benzyl)-phenyl]-1-hydroxymethyl-4-oxa-spiro[2.5]octane-6,7,8-triol Step III. To a solution of above mixture in methanol (10 mL), 10% Pd/C (110 mg) and 2 drops of con. HCl added and stirred under hydrogen atmosphere at room temperature for 18 hours. The reaction mixture was filtered through celite bed, washed with methanol (20 mL). Crude product was purified by preparative HPLC to furnish 10 mg of (5S,6R,7R,8S)-5-[4-Chloro-3-(4-ethoxy-benzyl)-phenyl]-1-hydroxymethyl-4-oxa spiro[2.5]octane-6,7,8-triol and 12 mg of (5S,6R,7R,8S)-5-[3-(4-Ethoxy-benzyl)-phenyl]1-hydroxymethyl-4-oxa-spiro[2.5]octane-6,7,8-triol.

(5S,6R,7R,8S)-5-[4-Chloro-3-(4-ethoxy-benzyl)-phenyl]-1-hydroxymethyl-4-oxa-spiro[2.5]octane-6,7,8-triol. $^1$H-NMR (400 M Hz, CD$_3$OD): (data given for major diastereomer only) δ 0.38 (t, J=6.0 Hz, 1H), 1.01 (dd, J=5.2 Hz, J=9.6 Hz, 1H), 1.37 (t, J=7.2 Hz, 3H), 1.40-1.48 (m, 1H), 3.35-3.46 (m, 2H), 3.54-3.64 (m, 2H), 3.81 (d, J=8.4 Hz, 2H), 3.95-4.02 (m, 4H), 4.10 (d, J=9.2 Hz, 1H), 6.80 (dd, J=1.6 Hz, J=6.4 Hz, 2H), 7.06 (d, J=8.8 Hz, 2H), 7.22 (dd, J=2.4 Hz, J=8.4 Hz 1H), 7.26 (d, J=1.6 Hz, 1H), 7.31-7.33 (m, 1H).

MS (ES) m/z 452 (M+18).

(5S,6R,7R,8S)-5-[3-(4-Ethoxy-benzyl)-phenyl]-1-hydroxymethyl-4-oxa-spiro[2.5]octane-6,7,8-triol. $^1$H-NMR (400 M Hz, CD$_3$OD (data given for diastereomeric mixture 60:40). δ 0.39 (t, J=6.0 Hz, 1H), 0.81 (dd, J=5.2 Hz, J=10.4 Hz, 1H), 0.89 (t, J=7.2 Hz, 1H), 0.90 (dd, J=5.2 Hz, J=9.6 Hz, 1H), 1.35 (t, J=7.2 Hz, 6H), 1.36-1.49 (m, 2H), 3.40-3.51 (m, 4H), 3.57-3.59 (m, 3H), 3.69-4.13 (m, 14H), 6.79 (d, J=8.4 Hz, 4H), 7.06-7.09 (m, 5H), 7.15-7.22 (m, 6H)

MS (ES) m/z 418 (M+18).

Examples 16 and 17

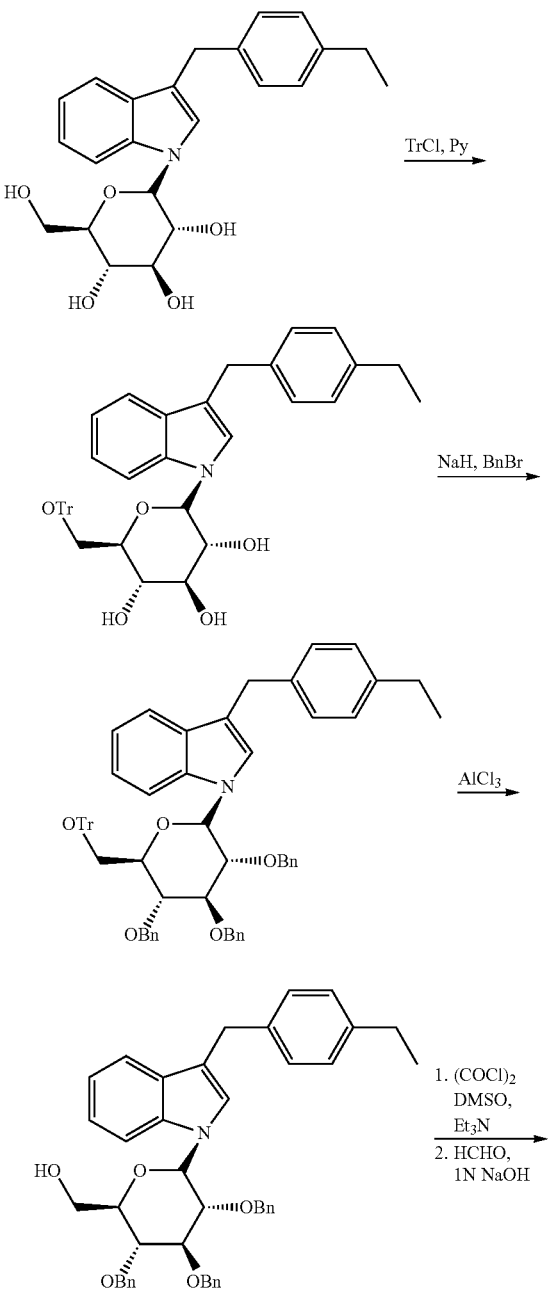

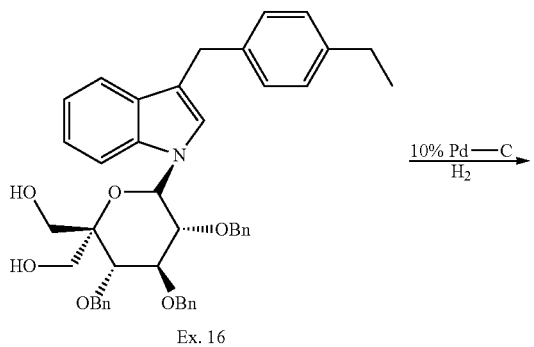

Ex. 16

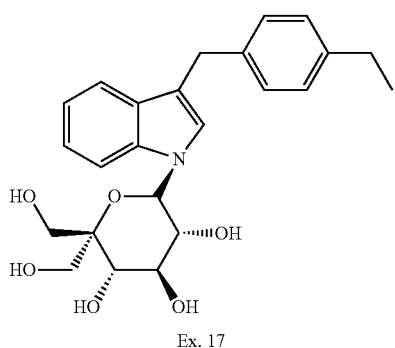

Ex. 17

Step I. To a mixture of (3R,4S,5S,6R)-2-[(R)-3-(4-ethyl-benzyl)-indol-1-yl]-6-hydroxymethyl-tetrahydro-pyran-3,4,5-triol (5.0 g, 12.5 mmole, prepared according to procedure as described in WO2008/013322), trityl chloride (3.85 g, 13.85 mmole) in pyridine (60 mL) was added at room temperature and heated at 80° C. for 18 hrs. The excess pyridine was evaporated; reaction mixture was diluted with water (250 mL) and washed with 1N dil. HCl (50 mL) extracted with dichloromethane (2×200 mL). The crude product obtained after the removal of solvent was purified using silica gel column chromatography (0.5% methanol in DCM) to furnish 6.8 of (3R,4S,5S,6R)-2-[(R)-3-(4-ethyl-benzyl)-indol-1-yl]-6-trityloxymethyl-tetrahydro-pyran-3,4,5-triol.

Step II. To a solution of (3R,4S,5S,6R)-2-[(R)-3-(4-ethyl-benzyl)-indol-1-yl]-6-trityloxymethyl-tetrahydro-pyran-3,4,5-triol (6.8 g, 110.64 mmole) in dry DMF (50 mL), sodium hydride (2.2 g, 46.8 mmole) was added at 0° C. and stirred at room temperature for 4 hours. Benzyl bromide (4.2 mL, 35.11 mmole), tetrabutylammoniumiodide (50 mg) added and reaction mixture stirred at room temperature for 18 hours. The reaction mixture was diluted with water (500 mL) and extracted with DCM (2×500 mL). The crude product obtained after removal of solvent to furnish 8.0 g of (R)-3-(4-ethyl-benzyl)-1-((3R,4S,5R,6R)-3,4,5-tris-benzyloxy-6-trityloxymethyl-tetrahydro-pyran-2-yl)-1H-indole.

Step M. To a solution of (R)-3-(4-ethyl-benzyl)-1-((3R,4S,5R,6R)-3,4,5-tris-benzyloxy-6-trityloxymethyl-tetrahydro-pyran-2-yl)-1H-indole (8.7 g, 9.5 mmole) in dry DCM (30 mL), AlCl$_3$ (1.3 gm, 9.57 mmole) in diethyl ether was added at 0° C. and stirred at room temperature for 2 hours. The reaction mixture was diluted with water (500 mL) and saturated aqueous NaHCO$_3$ (50 mL), extracted with DCM (2×250 mL). The crude product obtained after the removal of solvent was purified using silica gel column chromatography (10% ethyl acetate in hexane) to furnish 1.0 g of {(2R,3R,4S,5R)-3,4,5-Tris-benzyloxy-6-[(R)-3-(4-ethyl-benzyl)-indol-1-yl]-tetrahydro-pyran-2-yl}-methanol.

Example 16

(3S,4S,5R,6S)-3,4,5-tris(benzyloxy)-6-(3-(4-ethyl-benzyl)-1H-indol-1-yl)tetrahydro-2H-pyran-2,2-diyl) dimethanol Step IV. To a solution of oxallyl chloride (0.25 mL, 2.84 mmole) in dry DCM (10 mL), DMSO (0.43 mL, 6.14 mmole) in DCM (1 mL) was added at −70° C. and stirred for 10 min., Solution of {(2R,3R,4S,5R)-3,4,5-Tris-benzyloxy-6-[(R)-3-(4-ethyl-benzyl)-indol-1-yl]-tetrahydro-pyran-2-yl}-methanol (1.0 g, 1.49 mmole) in DCM (4 mL) was added during min at −70° C. and reaction mixture stirred for 1 hour. Triethylamine (2.1 mL, 14.9 mmole) added and allowed stir at room temperature for 15 min. The reaction mixture was diluted with water (25 mL) and extracted with DCM (2×25 mL). The crude product obtained after the removal of solvent was co evaporated with toluene (20 mL×4) to furnish crude aldehyde. To this crude aldehyde 1,4 dioxane (30 mL), 1N NaOH (20 mL), 37% aq. HCHO (20 mL) added and stirred for 72 hours. The reaction mixture was diluted with water (25 mL) and extracted with ethyl acetate (2×25 mL). The crude product obtained after the removal of solvent was purified using silica gel column chromatography (20% ethyl acetate in hexane) to furnish 350 mg {(3S,4S,5R)-3,4,5-Tris-benzyloxy-6-[(R)-3-(4-ethyl-benzyl)-indol-1-yl]-2-hydroxymethyl-tetrahydro-pyran-2-yl}-methanol.

Example 17

3S,4S,5R)-6-[(R)-3-(4-Ethyl-benzyl)-indol-1-yl]-2,2-bis-hydroxymethyl-tetrahydro-pyran-3,4,5-triol Step V. To a solution of {(3S,4S,5R)-3,4,5-tris-benzyloxy-6-[(R)-3-(4-ethyl-benzyl)-indol-1-yl]-2-hydroxymethyl-tetrahydro-pyran-2-yl}methanol (350 mg, 0.50 mmole) in methanol (10 mL), 10% Pd/C (100 mg) and 2 drops of con. HCl added and stirred under hydrogen atmosphere at room temperature for 18 hours. The reaction mixture was filtered through celite bed, washed with methanol (20 mL). The crude product was purified by preparative HPLC to furnish 10 mg of 3S,4S,5R)-6-[(R)-3-(4-Ethyl-benzyl)-indol-1-yl]-2,2-bis-hydroxymethyl-tetrahydro-pyran-3,4,5-triol $^1$H-NMR (400 M Hz, CD$_3$OD): δ1.89 (t, J=7.6 Hz, 3H), 2.58 (q, J=7.6 Hz, 2H), 3.61 (d, J=11.6 Hz, 1H), 3.70 (d, J=11.6 Hz, 1H), 3.80-3.86 (m, 4H), 3.94 (t, J=9.2 Hz, 1H), 4.0 (s, 2H), 4.15 (d, J=12.4 Hz, 1H), 5.92 (d, J=8.2 Hz, 1H), 6.97 (t, J=7.6 Hz, 1H), 7.06 (d, J=8.4 Hz, 2H), 7.11 (t, J=8.4 Hz, 1H), 7.17-7.20 (m, 2H), 7.39 (d, J=8.0 Hz, 1H), 7.60 (d, J=8.4 Hz, 1H)

MS (ES) m/z 428 (M+1). .

Examples 18 and 19

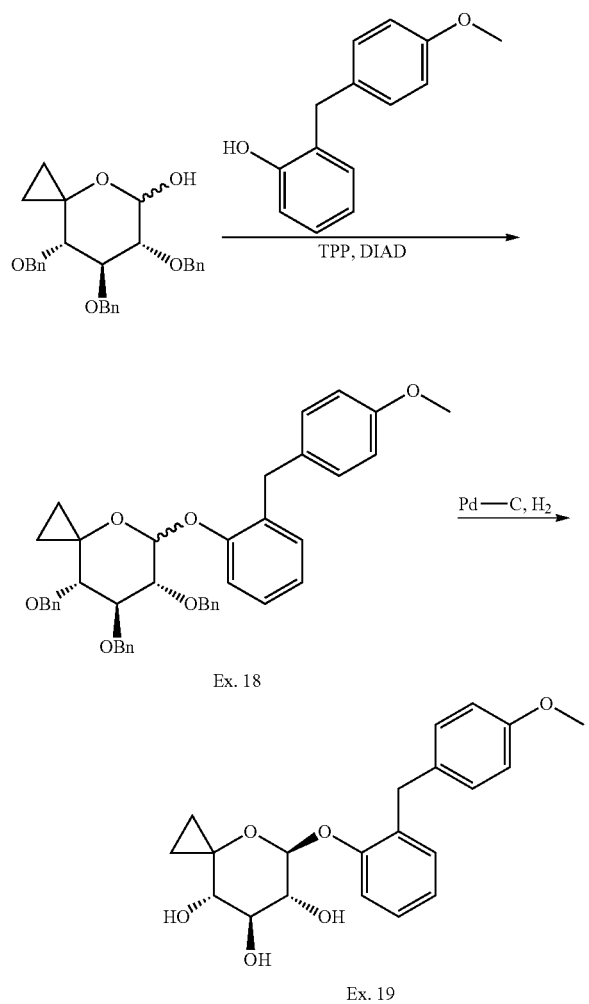

Ex. 18

Ex. 19

Example 18

(6R,7S,8S)-6,7,8-tris(benzyloxy)-5-(2-(4-methoxy-benzyl)phenoxy)-4-oxaspiro[2.5]octane Step I. (6R,7S,8S)-6,7,8-Tris-benzyloxy-4-oxaspiro[2.5]octan-5-ol (prepared according to an analogous procedure as described in *J. Org. Chem.* 2002, 67, 3733; *Helv. Chim, Acta* 1990, 73, 1329; *Tetrahedron Lett.* 1998, 39, 2021) (220 mg, 0.49 mmol) 2-(4-methoxybenzyl)-phenol (105 mg, 0.49 mmol) and triphenyl phosphine (155 mg, 0.59 mmol) were mixed under argon atmosphere followed by the addition of dry THF. The contents were cooled to 0° C. and DIAD (0.12 ml, 0.59 mmol) was added drop wise. The reaction mixture was refluxed for 12 hours and quenched with 1N dil. HCl (2 mL) and extracted with ethyl acetate (10×3 mL). Organic layer was washed with brine, dried over $Na_2SO_4$, concentrated under reduced pressure to give the crude product which was purified by flash column chromatography using 1:4 (Ethyl acetate:Hexane) as eluent to yield 200 mg of 5R,6R,7S,8S)-6,7,8-tris-benzyloxy-5-[2-(4-methoxy-benzyl)-phenoxy]-4-oxa-spiro[2.5]octane.

Example 19

5R,6R,7S,8S)-5-[2-(4-Methoxy-benzyl)-phenoxy]-4-oxa-spiro[2.5]octane-6,7,8-triol Step II. To a solution of (5R,6R,7S,8S)-6,7,8-tris-benzyloxy-5-[2-(4-methoxy-benzyl)-phenoxy]-4-oxa-spiro[2.5]octane (190 mg, 0.29 mmol) in methanol (5 ml) was added 10% Pd/C (60 mg) and stirred under hydrogen atmosphere at room temperature overnight. The reaction mixture was filtered through celite bed, washed with methanol (20 mL). The crude product was purified by preparative HPLC to furnish the title compound (22 mg).

$^1$H-NMR (400 MHz, DMSO-$d_6$): δ 0.60-0.64 (m, 2H), 0.71-73 (m, 2H), 3.25-3.29 (m, 1H), 3.44 (dd, J=7.2, 5.6 Hz, 1H), 3.60 (dd, J=8.4, 4.8 Hz, 1H), 3.70 (s, 3H), 3.80 (d, J=14.4 Hz, 1H), 3.97 (d, J=14.4 Hz, 1H), 4.81 (d, J=7.6 Hz, 1H), 5.08 (br d, J=5.2 Hz, 1H), 5.16 (br s, 1H), 5.41 (br s, 1H), 6.81 (d, J=8.4 Hz, 2H), 6.87 (d, J=8.4 Hz, 1H), 6.90 (d, J=7.6 Hz, 1H), 7.06-7.14 (m, 2H), 7.17 (d, J=8.4 Hz, 2H).
MS (ES) m/z 390.1.0 (M+H).

Following examples were prepared by using procedures analogous to those used to prepare Examples 9-10:

| Example 20 | 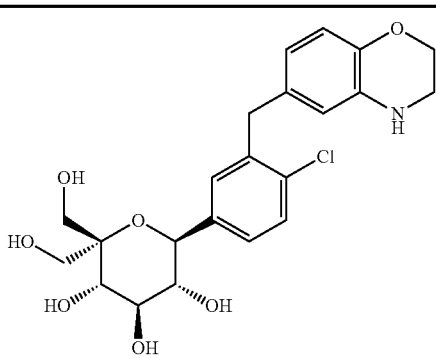 (3S,4R,5R,6S)-6-[4-Chloro-3-(3,4-dihydro-2H-benzo[1,4]oxazin-6-ylmethyl)-phenyl]-2,2-bis-hydroxymethyl-tetrahydro-pyran-3,4,5-triol | $^1$H NMR (400 MHz, $CD_3OD$): δ 3.20-3.40 (m, 4H), 3.66-3.84 (m, 4H), 3.90 (q, J = 14.2 Hz, 2H), 4.06 (d, J = 12.8 Hz, 1H), 4.15 (t, J = 4.4 Hz. 2H), 4.47 (d, J = 9.6 Hz, 1H), 6.44 (dd, J = 2.0, 8.0 Hz, 1H), 6.46 (d, J = 1.6 Hz, 1H), 6.57 (d, J = 8.0 Hz, 1H), 7.30-7.40 (m, 3H). MS (ES) m/z 451.9 (M + 1). |
|---|---|---|

| Example 21 | 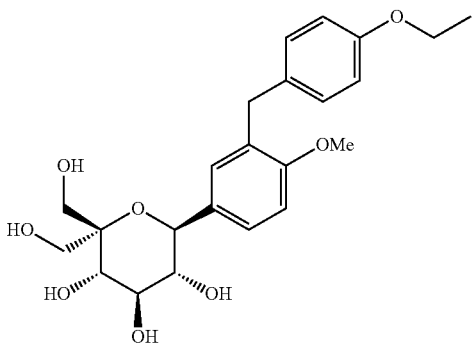 (3S,4R,5R,6S)-6-[3-(4-Ethoxy-benzyl)-4-methoxy-phenyl]-2,2-bis-hydroxymethyl-tetrahydro-pyran-3,4,5-triol | $^{1}$H NMR (400 MHz, CD$_{3}$OD): δ 1.34 (t, J = 7.2 Hz, 3H), 6.65-3.80 (m, 9H), 3.86 (d, J = 11.6 Hz, 2H), 3.94 (q, J = 7.2 Hz, 2H), 4.05 (d, J = 12.8 Hz, 1H), 4.40 (d, J = 9.6 Hz, 1H), 6.74 (d, J = 8.4 Hz, 2H), 6.89 (d, J = 8.4 Hz, 1H), 7.08 (d, J = 8.4 Hz, 2H), 7.22 (d, J = 1.6 Hz, 1H), 7.28 (dd, J = 8.0, 2.0 Hz, 1H). MS (ES) m/z 452.1 (M + 18). |
|---|---|---|
| Example 22 | 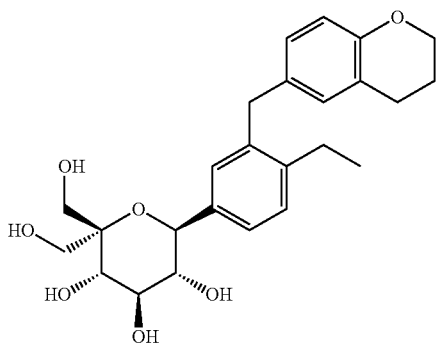 (3S,4R,5R,6S)-6-(3-Chroman-6-ylmethyl-4-ethyl-phenyl)-2,2-bis-hydroxymethyl-tetrahydro-pyran-3,4,5-triol | $^{1}$H NMR (400 MHz, CD$_{3}$OD): δ 1.06 (t, J = 7.6 Hz, 3H), 1.90-1.95 (m, 2H), 2.57 (q, J = 7.6, 15.2 Hz, 2H), 2.68 (t, J = 6.4 Hz, 2H), 3.29-3.36 (m, 2H), 3.67-3.80 (m, 4H), 3.90 (s, 2H), 4.05-4.10 (m, 3H), 4.45 (d, J = 9.2 Hz, 1H), 6.57 (d, J = 8.4 Hz, 1H), 6.77-6.80 (m, 2H), 7.15 (d, J = 8.0 Hz, 1H), 7.24 (s, 1H), 7.30 (dd, J = 2.0, 8.0 Hz, 1H). MS (ES) m/z 462.4 (M + 18). |

Following examples were prepared by using procedures analogous to those used to prepare Examples 1-2:

| Example 23 | 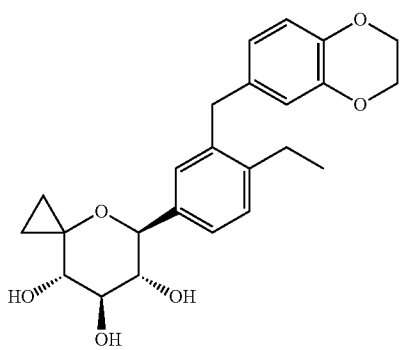 [SMILES: CCc1ccc([C@@H]2OC3(CC3)[C@@H](O)[C@H](O)[C@H]2O)cc1Cc1ccc2c(c1)OCCO2] (5S,6R,7R,8S)-5-[3-(2,3-Dihydro-benzo[1,4]dioxin-6-ylmethyl)-4-ethyl-phenyl]-4-oxa-spiro[2.5]octane-6,7,8-triol | $^{1}$H NMR (400 MHz, CD$_{3}$OD): δ 0.53-0.57 (m, 1H), 0.70-0.74 (m, 1H), 0.82-0.83 (m, 2H), 10.6 (t, J = 7.6 Hz, 3H), 2.56 (q, J = 7.6 Hz, 2H), 3.43-3.52 (m, 2H), 3.84 (d, J = 8.4 Hz, 1H), 3.88 (s, 2H), 4.12 (d, J = 8.8 Hz, 1H), 4.17 (s, 4H), 6.53-56.57 (m, 2H), 6.68 (d, J = 8.0 Hz, 1H), 7.12-7.19 (m, 3H); MS (ES) 430.3 (M + 18). |
|---|---|---|

| | | |
|---|---|---|
| Example 24 | 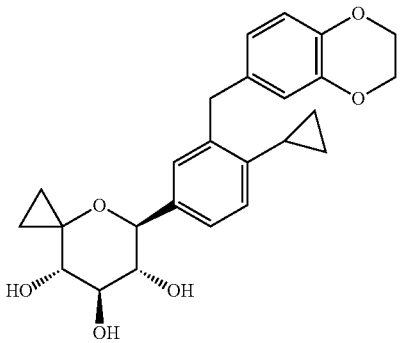 [SMILES: O[C@@H]1[C@@H](O)[C@H](O)C2(CC2)O[C@H]1c1ccc(C2CC2)c(Cc2ccc3c(c2)OCCO3)c1]<br><br>(5S,6R,7R,8S)-5-[4-Cyclopropyl-3-(2,3-dihydro-benzo[1,4]dioxin-6-ylmethyl)-phenyl]-4-oxa-spiro[2.5]octane-6,7,8-triol | $^1$H NMR (400 MHz, CD$_3$OD): δ 0.52-0.56 (m, 3H), 0.69-0.73 (m, 1H), 0.81-0.85 (m, 4H), 1.79-1.82 (m, 1H), 3.42-3.50 (m, 2H), 3.84 (d, J = 8.4 Hz, 1H), 4.01-4.15 (m, 2H), 4.16 (d, J = 9.2 Hz, 1H), 4.17 (s, 4H), 6.58-6.61 (m, 2H), 6.68 (d, J = 8.0 Hz, 1H), 6.95 (d, J = 7.6 Hz, 1H), 7.12-7.15 (m, 2H); MS (ES) m/z 442.4 (M + 18). |
| Example 25 | 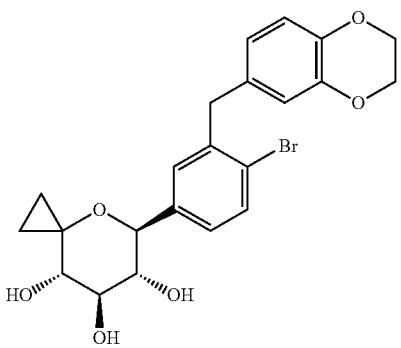 [SMILES: O[C@@H]1[C@@H](O)[C@H](O)C2(CC2)O[C@H]1c1ccc(Br)c(Cc2ccc3c(c2)OCCO3)c1]<br><br>(5S,6R,7R,8S)-5-[4-Bromo-3-(2,3-dihydro-benzo[1,4]dioxin-6-ylmethyl)-phenyl]-4-oxa-spiro[2.5]octane-6,7,8-triol | $^1$H NMR (400 MHz, CD$_3$OD): δ 0.52-0.55 (m, 1H), 0.70-0.73 (m, 1H), 0.79-0.855 (m, 2H), 3.30-3.46 (m, 2H), 3.82 (d, J = 8.8 Hz, 1H), 3.94-4.05 (m, 2H), 4.10 (d, J = 8.8 Hz, 1H), 4.18 (s, 4H), 6.61 (d, J = 6.8 Hz, 2H), 6.70 (d, J = 8.8 Hz, 1H), 7.12 (d, J = 8.4 Hz, 1H), 7.23 (s, 1H), 7.51 (d, J = 8.4 Hz, 1H), MS (ES) m/z 481 (M + 18). |
| Example 26 | 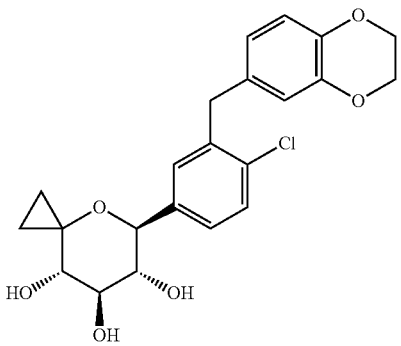<br><br>(5S,6R,7R,8S)-5-[4-Chloro-3-(2,3-dihydro-benzo[1,4]dioxin-6-ylmethyl)-phenyl]-4-oxa-spiro[2.5]octane-6,7,8-triol | $^1$H NMR (400 MHz, CD$_3$OD): δ 0.52-0.55 (m, 1H), 0.71-0.73 (m, 1H), 0.79-0.85 (m, 2H), 3.36-3.47 (m, 2H), 3.83 (d, J = 8.8 Hz, 1H), 3.91-4.00 (m, 2H), 4.12 (d, J = 9.6 Hz, 1H), 4.18 (s, 4H), 6.63 (d, J = 7.2 Hz, 2H), 6.70 (d, J = 8.8 Hz, 1H), 7.19-7.24 (m, 2H), 7.32 (d, J = 8.4 Hz, 1H), MS (ES) m/z 436.2 (M + 18). |

| Example 27 | 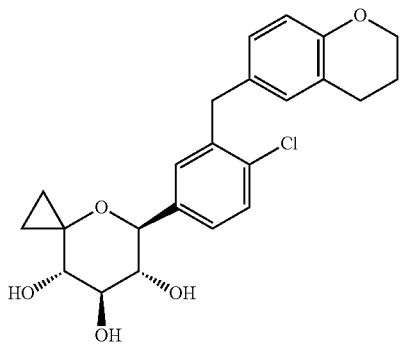 [SMILES: O[C@@H]1[C@@H](O)[C@H](O)C2(CC2)O[C@H]1c1ccc(Cl)c(Cc2ccc3c(c2)OCCO3)c1]
(5S,6R,7R,8S)-5-(4-Chloro-3-chroman-6-ylmethyl-phenyl)-4-oxa-spiro[2.5]octane-6,7,8-triol | ¹H NMR (400 MHz, CD₃OD): δ 0.51-0.57 (m, 1H), 0.70-0.74 (m, 1H), 0.79-0.86 (m, 2H), 1.91-1.97 (m, 2H), 2.71 (t, J = 6.4 Hz, 2H), 3.36-3.46 (m, 2H), 3.82 (d, J = 8.8 Hz, 1H), 3.92-4.05 (m, 2H), 4.09-4.12 (m, 3H), 6.60 (d, J = 8.4 Hz, 1H), 6.84-6.86 (m, 2H), 7.18-7.22 (m, 2H), 7.32 (d, J = 8.4 Hz, 1H), MS (ES) m/z 434.2 (M + 18). |
|---|---|---|
| Example 28 | 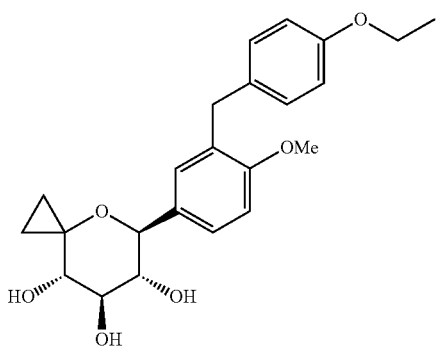 [SMILES: CCOc1ccc(Cc2cc([C@@H]3OC4(CC4)[C@@H](O)[C@H](O)[C@H]3O)ccc2OC)cc1]
(5S,6R,7R,8S)-5-[3-(4-Ethoxy-benzyl)-4-methoxy-phenyl]-4-oxa-spiro[2.5]octane-6,7,8-triol | ¹H NMR (400 MHz, CD₃OD): δ 0.51-0.54 (m, 2H), 0.67-0.71 (m, 2H), 1.34 (t, J = 6.8 Hz, 3H), 3.41-3.46 (m, 2H), 3.73-3.80 (m, 3H), 3.81-3.88 (m, 3H), 3.96 (q, J = 6.8 Hz, 2H), 4.07 (d, J = 8.8 Hz, 1H), 6.75 (d, J = 8.4 Hz, 2H), 6.89 (d, J = 8.4 Hz, 1H), 7.06-7.09 (m, 3H), 7.17 (dd, J = 2.4, 8.4 Hz, 1H). MS (ES) m/z: 418.2 (M + 18). |
Examples 29 and 30

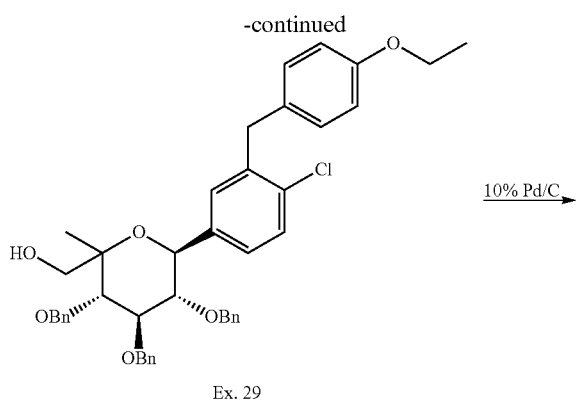

Ex. 29

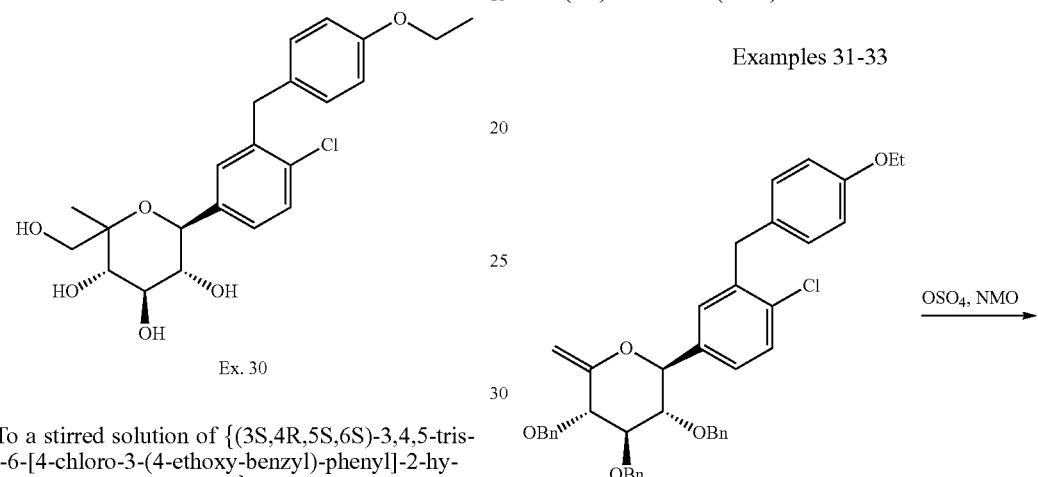

Step I. To a stirred solution of {(3S,4R,5S,6S)-3,4,5-tris-benzyloxy-6-[4-chloro-3-(4-ethoxy-benzyl)-phenyl]-2-hydroxymethyl-tetrahydro-pyran-2-yl}-methanol (Example 9, 500 mg, 0.7 mmol) in pyridine (15 mL) was added p-toluene sulfonyl chloride (670 mg, 3.5 mmol) and heated at 80° C. for 48 h. The volatiles were evaporated, the resulting residue was diluted with ethyl acetate and washed with 1N HCl, brine, dried over sodium sulfate and concentrated to give 580 mg of bis-tosylate of {(3S,4R,5S,6S)-3,4,5-tris-benzyloxy-6-[4-chloro-3-(4-ethoxy-benzyl)-phenyl]-2-hydroxymethyl-tetrahydro-pyran-2-yl}-methanol.

Example 29

{(3S,4R,5S,6S)-3,4,5-tris-benzyloxy-6-[4-chloro-3-(4-ethoxy-benzyl)-phenyl]-2-methyl-tetrahydro-pyran-2-yl}-methanol Step II. To a stirred solution of bis-tosylate of {(3S,4R,5S,6S)-3,4,5-Tris-benzyloxy-6-[4-chloro-3-(4-ethoxy-benzyl)-phenyl]-2-hydroxymethyl-tetrahydro-pyran-2-yl}-methanol (250 mg, 0.20 mmol) in dry THF (15 mL) was added lithium aluminum hydride (40 mg, 0.80 mmol) at 0° C. and heated at 70° C. for 16 hour. The excess lithium aluminum hydride was quenched with saturated aqueous sodium sulfate solution and filtered through celite bed. The filtrate was concentrated and purified by using silica gel column chromatography (30% ethyl acetate in hexane) to furnish 150 mg of {(3S,4R,5S,6S)-3,4,5-tris-benzyloxy-6-[4-chloro-3-(4-ethoxy-benzyl)-phenyl]-2-methyl-tetrahydro-pyran-2-yl}-methanol.

Example 30

(3S,4R,5R,6S)-6-[4-chloro-3-(4-ethoxy-benzyl)-phenyl]-2-hydroxymethyl-2-methyl-tetrahydro-pyran-3,4,5-triol Step III. To a stirred solution of {(3S,4R,5S,6S)-3,4,5-tris-benzyloxy-6-[4-chloro-3-(4-ethoxy-benzyl)-phenyl]-2-methyl-tetrahydro-pyran-2-yl}-methanol (150 mg, 0.21 mmol) in methanol (10 mL) was added 10% Pd/C (70 mg) and 2 drops of conc. HCl. The reaction mixture was stirred under hydrogen atmosphere (balloon pressure) at room temperature for 18 hours. The reaction mixture was filtered through cetlie bed, washed with methanol, filtrate was concentrated and purified by preparative chiral HPLC to furnish 35 mg of (3S,4R,5R,6S)-6-[4-chloro-3-(4-ethoxy-benzyl)-phenyl]-2-hydroxymethyl-2-methyl-tetrahydro-pyran-3,4,5-triol.

$^1$H-NMR (400 MHz, CD$_3$OD): δ 1.26 (s, 3H), 1.33 (t, J=5.6 Hz, 3H), 3.20 (t, J=9.6 Hz, 1H), 3.29-3.66 (m, 1H), 3.59-3.66 (m, 2H), 3.93-4.02 (m, 5H), 4.39 (d, J=9.6 Hz, 1H), 6.76-6.78 (m, 2H), 7.06 (d, J=8.8 Hz, 2H), 7.22-7.32 (m, 3H), MS (ES) m/z 423.2 (M+1).

Examples 31-33

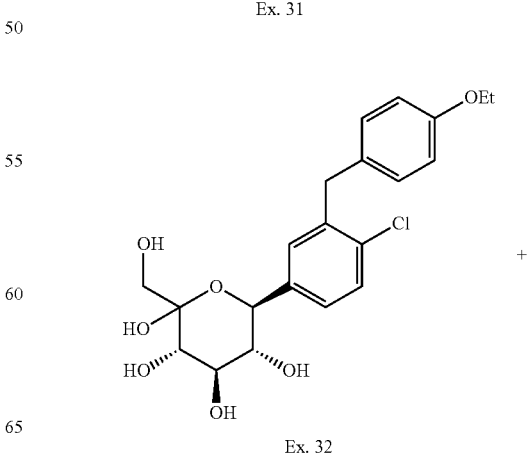

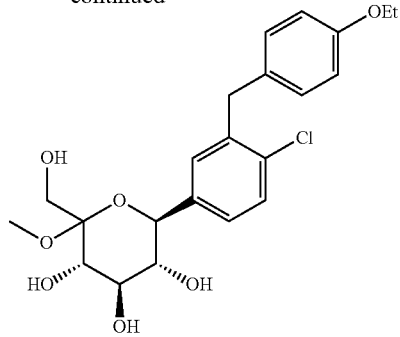

Ex. 33

Example 31

(3S,4R,5S,6S)-3,4,5-tris-benzyloxy-6-[4-chloro-3-(4-ethoxy-benzyl)-phenyl]-2-hydroxymethyl-tetrahydro-pyran-2-ol Step I. To a stirred solution of (2S,3S,4R,5S)-3,4,5-tris-benzyloxy-2-[4-chloro-3-(4-ethoxy-benzyl)-phenyl]-6-methylene-tetrahydro-pyran (100 mg, 0.15 mmol) in dry dichloromethane (10 mL) was added N-methyl morpholine N-oxide (103 mg, 0.30 mmol) and OsO$_4$ (1 mg) at room temperature. After stirring for overnight, reaction mixture was diluted with water, aqueous sodium metabisulfite and extracted with DCM. Organic layer was concentrated and purified by silica gel column chromatography (1% methanol in DCM) to furnish 110 mg of (3S,4R,5S,6S)-3,4,5-tris-benzyloxy-6-[4-chloro-3-(4-ethoxy-benzyl)-phenyl]-2-hydroxymethyl-tetrahydro-pyran-2-ol.

Example 32

(3S,4R,5R,6S)-6-[4-Chloro-3-(4-ethoxy-benzyl)-phenyl]-2-hydroxymethyl-tetrahydro-pyran-2,3,4,5-tetraol

And Example 33

(3S,4R,61:4,6S)-6-[4-Chloro-3-(4-ethoxy-benzyl)-phenyl]-2-hydroxymethyl-2-methoxy-tetrahydro-pyran-3,4,5-triol Step II. To a mixture of (3S,4R,5S,6S)-3,4,5-tris-benzyloxy-6-[4-chloro-3-(4-ethoxy-benzyl)-phenyl]-2-hydroxymethyl-tetrahydro-pyran-2-ol (see Example 1, step III, 100 mg, 0.14 mmol) in methanol (3 mL) was added 10% Pd/C (60 mg) and 2 drops of conc. HCl. and stirred under hydrogen atmosphere (balloon pressure) at room temperature for 18 h. The reaction mixture was filtered through a cetlie bed, washed with methanol, concentrated and purified by preparative HPLC to furnish (3S,4R,5R,6S)-6-[4-chloro-3-(4-ethoxy-benzyl)-phenyl]-2-hydroxymethyl-tetrahydro-pyran-2,3,4,5-tetraol (20 mg) and (3S,4R,5R,6S)-6-[4-chloro-3-(4-ethoxy-benzyl)-phenyl]-2-hydroxymethyl-2-methoxy-tetrahydro-pyran-3,4,5-triol (5 mg).

(3S,4R,5R,6S)-6-[4-Chloro-3-(4-ethoxy-benzyl)-phenyl]-2-hydroxymethyl-tetrahydro-pyran-2,3,4,5-tetraol:
$^1$H-NMR (400 MHz, CD$_3$OD): δ 1.38 (t, J=6.8 Hz, 3H), 3.29-3.33 (m, 1H), 3.52 (d, J=11.2 Hz, 1H), 3.61 (d, J=9.2 Hz, 1H), 3.70 (d, J=11.6 Hz, 1H), 3.75-3.79 (m, 1H), 3.98 (m, 4H), 4.64 (d, J=9.6 Hz, 1H), 6.81 (d, J=9.2 Hz, 2H), 7.11 (d, J=8.4 Hz, 2H), 7.34-7.37 (m, 3H); MS (ES) m/z 442.2 (M+18).

(3S,4R,5R,6S)-6-[4-chloro-3-(4-ethoxy-benzyl)-phenyl]-2-hydroxymethyl-2-methoxy-tetrahydro-pyran-3,4,5-triol;
$^1$H-NMR (400 MHz, CD$_3$OD): δ 1.38 (t, J=6.8 Hz, 3H), 3.31 (s, 3H), 3.74-3.77 (m, 4H), 3.97-4.06 (m, 5H), 4.32 (d, J=9.6 Hz, 1H), 6.82 (d, J=8.8 Hz, 2H), 7.12 (d, J=8.4 Hz, 2H) 7.35-7.39 (m, 3H); MS (ES) m/z 456.2 (M+18).

Examples 34-35

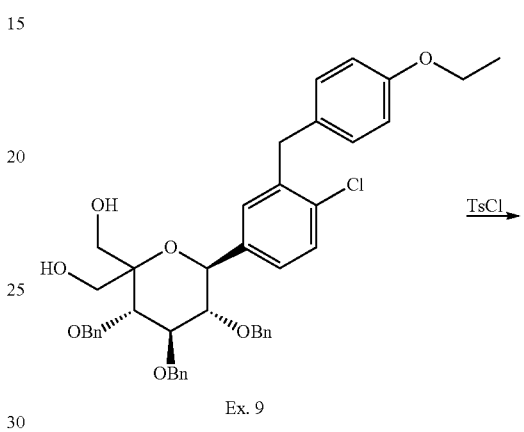

Ex. 9

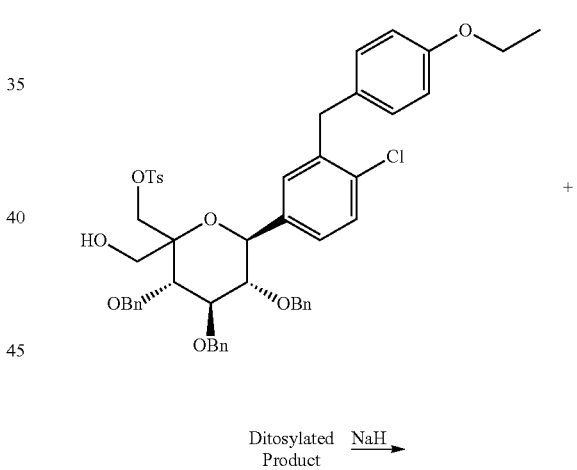

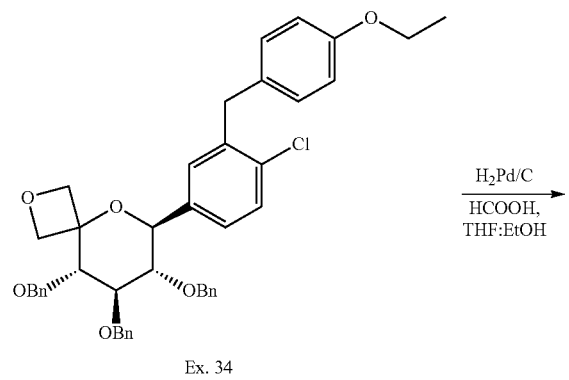

Ex. 34

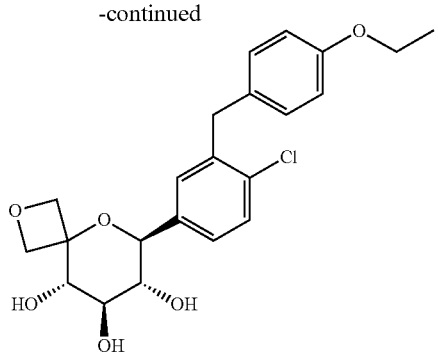

Ex. 35

Step I. To a stirred solution of {(3S,4R,5S,6S)-3,4,5-tris-benzyloxy-6-[4-chloro-3-(4-ethoxy-benzyl)-phenyl]-2-hydroxymethyl-tetrahydro-pyran-2-yl}-methanol (Example 9, 500 mg, 0.70 mmol) in pyridine (15 mL) was added p-toluene sulfonyl chloride (670 mg, 0.21 mmol). After stirring for overnight at room temperature, reaction mixture was heated to 80° C. for another 18 h. The volatiles were evaporated, resulting residue was taken in ethyl acetate and washed with 1N HCl, brine, concentrated to furnish toluene-4-sulfonic acid (3S,4R,5S,6S)-3,4,5-tris-benzyloxy-6-[4-chloro-3-(4-ethoxy-benzyl)-phenyl]-2-hydroxymethyl-tetrahydro-pyran-2-ylmethyl ester (580 mg). The crude product was used as such for next step without purification which also contains small amount of bis-tosylate.

Example 34

(6S,7S,8R,9S)-7,8,9-tris-benzyloxy-6-[4-chloro-3-(4-ethoxy-benzyl)-phenyl]-2,5-dioxa-spiro[3.5]nonane Step II. To a stirred solution of toluene-4-sulfonic acid (3S,4R,5S,6S)-3,4,5-tris-benzyloxy-6-[4-chloro-3-(4-ethoxy-benzyl)-phenyl]-2-hydroxymethyl-tetrahydro-pyran-2-ylmethyl ester (200 mg, 0.22 mmol) in THF (8 mL) was added NaH (60% in mineral oil, 21 mg, 0.44 mmol) and heated to 70° C. for overnight. Reaction mixture was diluted with ice water and extracted with ethyl acetate, concentrated and purified by silica gel column chromatography (30% ethyl acetate in hexanes) to furnish 60 mg of (6S,7S,8R,9S)-7,8,9-tris-benzyloxy-6-[4-chloro-3-(4-ethoxy-benzyl)-phenyl]-2,5-dioxa-spiro[3.5]nonane.

Example 35

(6S,7R,8R,9S)-6-[4-chloro-3-(4-ethoxy-benzyl)-phenyl]-2,5-dioxa-spiro[3.5]nonane-7,8,9-triol Step III. To a solution of (6S,7S,8R,9S)-7,8,9-tris-benzyloxy-6-[4-chloro-3-(4-ethoxy-benzyl)-phenyl]-2,5-dioxa-spiro[3.5]nonane (110 mg, 0.15 mmol) in THF:EtOH (1:1, 5 mL) was added 10% Pd/C (60 mg) followed by formic acid (0.46 mL, 12 mmol) and stirred under hydrogen atmosphere at room temperature for 8 hours. The reaction mixture was filtered through cetlie bed, neutralized with saturated aqueous NaHCO$_3$ solution, extracted with EtOAc, concentrated and purified by preparative HPLC to furnish 31 mg of (6S,7R,8R, 9S)-6-[4-chloro-3-(4-ethoxy-benzyl)-phenyl]-2,5-dioxa-spiro[3.5]nonane-7,8,9-triol.

$^1$H-NMR (400 M Hz, CD$_3$OD): δ 1.35 (t, J=6.8 Hz, 3H), 3.23-3.25 (m, 2H), 3.34-3.36 (m, 1H), 3.97 (q, J=7.3 Hz, 2H), 4.02-4.06 (m, 3H), 4.48 (d, J=6.8 Hz, 1H), 4.60 (d, J=6.8 Hz, 1H), 4.81 (d, J=6.8 Hz, 1H), 4.91 (d, J=6.8 Hz, 1H), 6.79 (d, J=8.8 Hz, 2H), 7.08 (d, J=8.8 Hz, 2H), 7.21-7.27 (m, 2H), 7.35 (d, J=8.0 Hz, 1H); MS (ES) m/z 438.3 (M+18).

Example 36

(6S,7R,8R,9S)-6-(3-Chroman-6-ylmethyl-4-ethyl-phenyl)-2,6-dioxa-spiro[3.5]nonane-7,8,9-triol

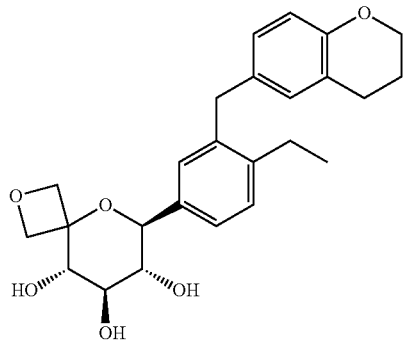 [SMILES: CCc1ccc([C@@H]2OC3(COC3)[C@@H](O)[C@H](O)[C@H]2O)cc1Cc1ccc2c(c1)CCCO2]

Example 36 was prepared by using procedures analogous to those used to prepare Examples 34 and 35.

$^1$H-NMR (400 M Hz, CD3OD): δ 1.08 (t, J=7.6 Hz, 3H), 1.91-1.96 (m, 2H), 2.59 (q, J=7.2 Hz, 2H), 2.69 (t, J=6.8 Hz, 2H), 3.24-3.86 (m, 3H), 3.90 (s, 2H), 4.04 (d, J=9.2 Hz, 1H), 4.09 (t, J=4.8 Hz, 2H), 4.49 (d, J=6.8 Hz, 1H), 4.63 (d, J=6.4 Hz, 1H), 4.82 (d, J=6.8 Hz, 1H), 4.92 (d, J=6.0 Hz, 1H), 6.59 (d, J=8.4 Hz, 1H), 6.77-6.81 (m, 2H), 7.16-7.23 (m, 3H); MS (ES) m/z 427.2 (M+1).

Examples 37 and 38

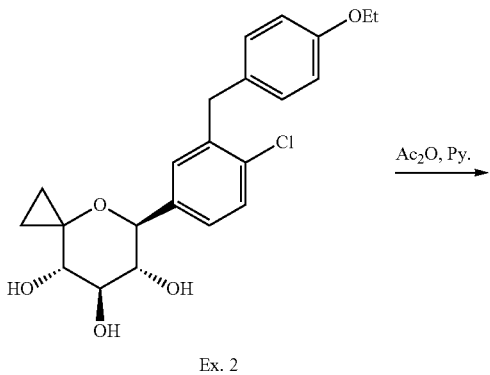

Ex. 2

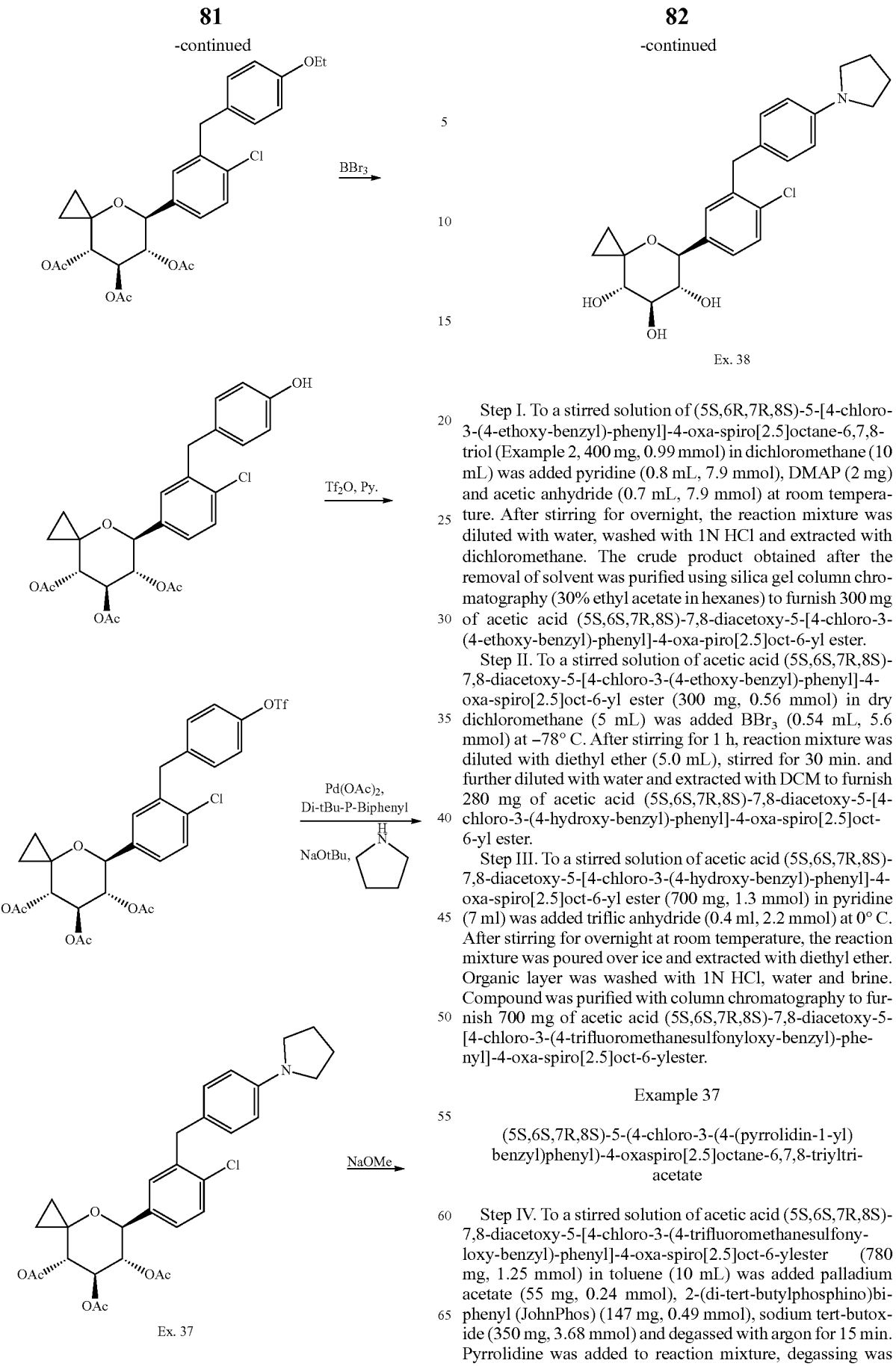

Step I. To a stirred solution of (5S,6R,7R,8S)-5-[4-chloro-3-(4-ethoxy-benzyl)-phenyl]-4-oxa-spiro[2.5]octane-6,7,8-triol (Example 2, 400 mg, 0.99 mmol) in dichloromethane (10 mL) was added pyridine (0.8 mL, 7.9 mmol), DMAP (2 mg) and acetic anhydride (0.7 mL, 7.9 mmol) at room temperature. After stirring for overnight, the reaction mixture was diluted with water, washed with 1N HCl and extracted with dichloromethane. The crude product obtained after the removal of solvent was purified using silica gel column chromatography (30% ethyl acetate in hexanes) to furnish 300 mg of acetic acid (5S,6S,7R,8S)-7,8-diacetoxy-5-[4-chloro-3-(4-ethoxy-benzyl)-phenyl]-4-oxa-piro[2.5]oct-6-yl ester.

Step II. To a stirred solution of acetic acid (5S,6S,7R,8S)-7,8-diacetoxy-5-[4-chloro-3-(4-ethoxy-benzyl)-phenyl]-4-oxa-spiro[2.5]oct-6-yl ester (300 mg, 0.56 mmol) in dry dichloromethane (5 mL) was added $BBr_3$ (0.54 mL, 5.6 mmol) at −78° C. After stirring for 1 h, reaction mixture was diluted with diethyl ether (5.0 mL), stirred for 30 min. and further diluted with water and extracted with DCM to furnish 280 mg of acetic acid (5S,6S,7R,8S)-7,8-diacetoxy-5-[4-chloro-3-(4-hydroxy-benzyl)-phenyl]-4-oxa-spiro[2.5]oct-6-yl ester.

Step III. To a stirred solution of acetic acid (5S,6S,7R,8S)-7,8-diacetoxy-5-[4-chloro-3-(4-hydroxy-benzyl)-phenyl]-4-oxa-spiro[2.5]oct-6-yl ester (700 mg, 1.3 mmol) in pyridine (7 ml) was added triflic anhydride (0.4 ml, 2.2 mmol) at 0° C. After stirring for overnight at room temperature, the reaction mixture was poured over ice and extracted with diethyl ether. Organic layer was washed with 1N HCl, water and brine. Compound was purified with column chromatography to furnish 700 mg of acetic acid (5S,6S,7R,8S)-7,8-diacetoxy-5-[4-chloro-3-(4-trifluoromethanesulfonyloxy-benzyl)-phenyl]-4-oxa-spiro[2.5]oct-6-ylester.

Example 37

(5S,6S,7R,8S)-5-(4-chloro-3-(4-(pyrrolidin-1-yl)benzyl)phenyl)-4-oxaspiro[2.5]octane-6,7,8-triyltriacetate Step IV. To a stirred solution of acetic acid (5S,6S,7R,8S)-7,8-diacetoxy-5-[4-chloro-3-(4-trifluoromethanesulfonyloxy-benzyl)-phenyl]-4-oxa-spiro[2.5]oct-6-ylester (780 mg, 1.25 mmol) in toluene (10 mL) was added palladium acetate (55 mg, 0.24 mmol), 2-(di-tert-butylphosphino)biphenyl (JohnPhos) (147 mg, 0.49 mmol), sodium tert-butoxide (350 mg, 3.68 mmol) and degassed with argon for 15 min. Pyrrolidine was added to reaction mixture, degassing was continued for another 15 min. After stirring for 24 h at room temperature, reaction mixture was filtered through celite bed, filtrate concentrated and used as such without any purification.

Example 38

5S,6R,7R,8S)-5-(4-chloro-3-[4-pyrrolidin-1-yl-benzyl)-phenyl]-4-oxa-spiro[2.5]octane-6,7,8-triol Step V. The crude reaction mixture obtained from step 1V was dissolved and stirred with methanol in the presence of sodium methoxide (75 mg) at room temperature for 3 h. The solvent was evaporated and the compound was purified by preparative HPLC to give 120 mg of 5S,6R,7R,8S)-5-[4-chloro-3-(4-pyrrolidin-1-yl-benzyl)-phenyl]-4-oxa-spiro [2.5]octane-6,7,8-triol, $^1$H NMR (400 MHz, CD$_3$OD): δ 0.50-0.54 (m, 1H), 0.69-0.72 (m, 1H), 0.81-0.82 (m, 2H), 1.96-2.10 (m, 4H), 3.10-3.25 (m, 4H), 3.30-3.46 (m, 2H), 3.82 (d, J=8.8 Hz, 1H), 3.94 (q, J=7.2, 15.0 Hz, 2H), 4.1 (d, J=9.6 Hz, 1H), 6.50 (dd, J=2.0, 6.8 Hz, 2H), 6.99 (d, J=8.0 Hz, 2H), 7.14 (m, 2H), 7.31 (d, J=8.4 Hz, 1H); MS (ES) m/z 430.0 (M+1).

Following examples were prepared by using procedures analogous to those used to prepare Examples 37 and 38.

Examples 41-44

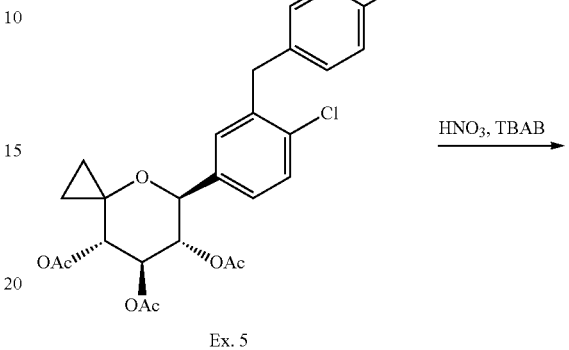

Ex. 5

| Example 39 | 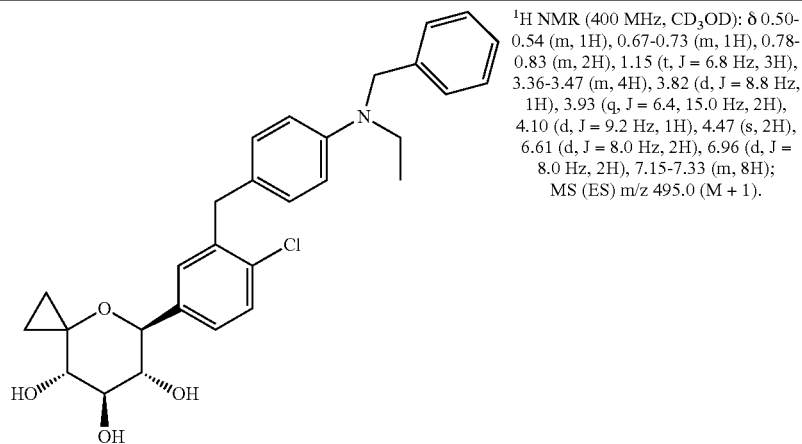 | $^1$H NMR (400 MHz, CD$_3$OD): δ 0.50-0.54 (m, 1H), 0.67-0.73 (m, 1H), 0.78-0.83 (m, 2H), 1.15 (t, J = 6.8 Hz, 3H), 3.36-3.47 (m, 4H), 3.82 (d, J = 8.8 Hz, 1H), 3.93 (q, J = 6.4, 15.0 Hz, 2H), 4.10 (d, J = 9.2 Hz, 1H), 4.47 (s, 2H), 6.61 (d, J = 8.0 Hz, 2H), 6.96 (d, J = 8.0 Hz, 2H), 7.15-7.33 (m, 8H); MS (ES) m/z 495.0 (M + 1). |
|---|---|---|
| | (5S,6R,7R,8S)-5-{3-[4-(Benzyl-ethyl-amino)-benzyl]-4-chloro-phenyl}-4-oxa-spiro[2.5]octane-6,7,8-triol | |
| Example 40 | 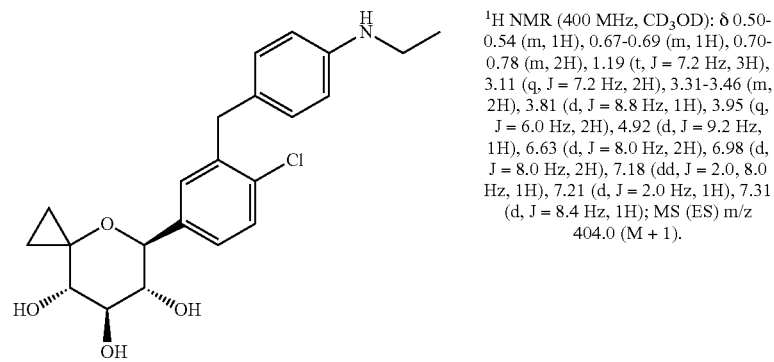 | $^1$H NMR (400 MHz, CD$_3$OD): δ 0.50-0.54 (m, 1H), 0.67-0.69 (m, 1H), 0.70-0.78 (m, 2H), 1.19 (t, J = 7.2 Hz, 3H), 3.11 (q, J = 7.2 Hz, 2H), 3.31-3.46 (m, 2H), 3.81 (d, J = 8.8 Hz, 1H), 3.95 (q, J = 6.0 Hz, 2H), 4.92 (d, J = 9.2 Hz, 1H), 6.63 (d, J = 8.0 Hz, 2H), 6.98 (d, J = 8.0 Hz, 2H), 7.18 (dd, J = 2.0, 8.0 Hz, 1H), 7.21 (d, J = 2.0 Hz, 1H), 7.31 (d, J = 8.4 Hz, 1H); MS (ES) m/z 404.0 (M + 1). |
| | (5S,6R,7R,8S)-5-[4-Chloro-3-(4-ethylamino-benzyl)-phenyl]-4-oxa-spiro[2.5]octane-6,7,8-triol | |

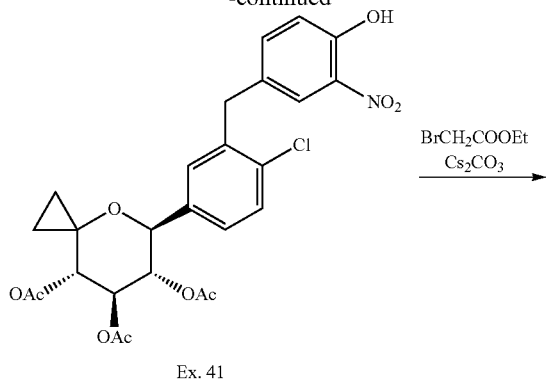

Ex. 41

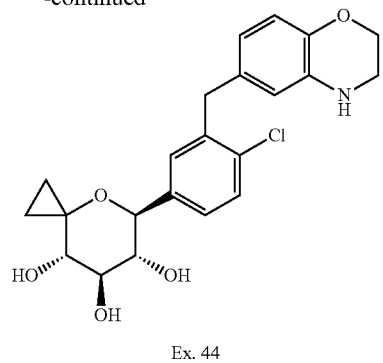

Ex. 44

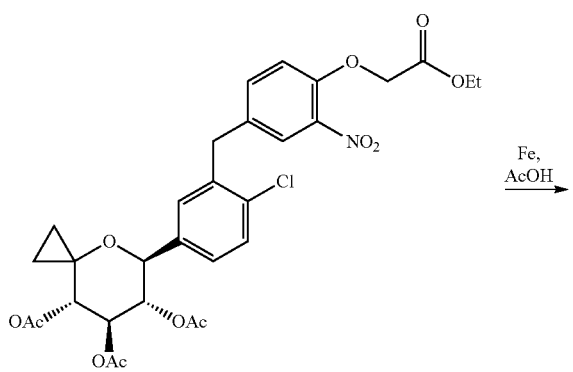

Ex. 42

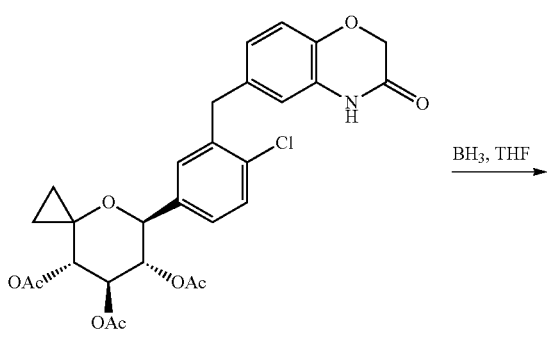

Ex. 43

Example 41

Acetic acid (5S,6S,7R,8S)-7,8-diacetoxy-5-[4-chloro-3-(4-hydroxy-3-nitro-benzyl)-phenyl]-4-oxa-spiro[2.5]oct-6-yl ester Step I. To a stirred solution of acetic acid (5S,6S,7R,8S)-7,8-diacetoxy-5-[4-chloro-3-(4-hydroxy-benzyl)-phenyl]-4-oxa-spiro[2.5]oct-6-yl ester (Example 5, 104 mg, 2 mmol) in dichloromethane (25 ml) was added $HNO_3$ (6% aqueous solution, 5.6 ml, 3.8 mmol) in a drop wise fashion, followed by the addition of tetrabutyl ammonium bromide (100 mg). The reaction mixture was stirred at room temperature until the complete conversion. The reaction mixture was diluted with DCM, washed with water, brine, concentrated and purified by silica gel chromatography to give 1.2 g of acetic acid (5S,6S,7R,8S)-7,8-diacetoxy-5-[4-chloro-3-(4-hydroxy-3-nitro-benzyl)-phenyl]-4-oxa-spiro[2.5]oct-6-yl ester.

Step II: To a stirred solution of acetic acid (5S,6S,7R,8S)-7,8-diacetoxy-5-[4-chloro-3-(4-hydroxy-3-nitro-benzyl)-phenyl]-4-oxa-spiro[2.5]oct-6-yl ester (1.2 g, 2.1 mmol) in anhydrous acetonitrile (40 mL) was added $Cs_2CO_3$ (3.0 g, 9.4 mmol) and bromoacetic acid ethyl ester (1.2 mL, 11.8 mmol). Reaction was heated to reflux under nitrogen atmosphere for 15 h. Reaction mixture was filtered, residue was washed with anhydrous acetonitrile and concentrated to obtain crude product. The crude product was purified by column chromatography to furnish {-4-[2-chloro-5-(5S,6S,7R,8S)-6,7,8-triacetoxy-4-oxa-spiro[2.5]oct-5-yl)-benzyl]-2-nitro-phenoxy}-acetic acid ethyl ester (515 mg).

Example 42

Acetic acid (5S,6S,7R,8S)-6,7-diacetoxy-5-[4-chloro-3-(3-oxo-3,4-dihydro-2H-benzo[1,4]oxazin-6-ylmethyl)-phenyl]-4-oxa-spiro[2.5]oct-8-yl ester Step III: To a stirred solution of {4-[2-chloro-5-(5S,6S,7R,8S)-6,7,8-triacetoxy-4-oxa-spiro[2.5]oct-5-yl)-benzyl]-2-nitro-phenoxy}-acetic acid ethyl ester (515 mg, 0.73 mmol) in glacial acetic acid (8 mL) was added iron powder (400 mg, 7.1 mmol) and stirred at 60° C. for overnight. Reaction mixture was cooled to room temperature, diluted with EtOAc (15 mL) and filtered through celite. Filtrate was concentrated and purified by column chromatography to furnish acetic acid (5S,6S,7R,8S)-6,7-diacetoxy-5-[4-chloro-3-(3-oxo-3,4-dihydro-2H-benzo[1,4]oxazin-6-ylmethyl)-phenyl]-4-oxa-spiro[2.5]oct-8-yl ester (265 mg)

Example 43

Acetic acid (5S,6S,7R,8S)-6,7-diacetoxy-5-[4-chloro-3-(3,4-dihydro-2H-benzo[1,4]oxazin-6-ylmethyl)-phenyl]-4-oxa-spiro[2.5]oct-8-yl ester Step IV: To a stirred solution of acetic acid (5S,6S,7R,8S)-6,7-diacetoxy-5-[4-chloro-3-(3-oxo-3,4-dihydro-2H-benzo[1,4]oxazin-6-ylmethyl)-phenyl]-4-oxa-spiro[2.5]oct-8-yl ester (100 mg, 0.18 mmol) in THF (6 mL) was added a solution of $BH_3$-THF (2.2 ml, 1.8 mmol) and heated to reflux overnight. Reaction was quenched with the addition of ethyl acetate. The solvent was evaporated and the crude product was purified by silica gel column chromatography to furnish the acetic acid (5S,6S,7R,8S)-6,7-diacetoxy-5-[4-chloro-3-(3,4-dihydro-2H-benzo[1,4]oxazin-6-ylmethyl)-phenyl]-4-oxa-spiro[2.5]oct-8-yl ester (56 mg).

Example 44

(5S,6R,7R,8S)-5-[4-chloro-3-(3,4-dihydro-2H-benzo[1,4]oxazin-6-ylmethyl)-phenyl]-4-oxa-spiro[2.5]octane-6,7,8-triol Step V: To a stirred solution of acetic acid (5S,6S,7R,8S)-6,7-diacetoxy-5-[4-chloro-3-(3,4-dihydro-2H-benzo[1,4]oxazin-6-ylmethyl)-phenyl]-4-oxa-spiro[2.5]oct-8-yl ester (100 mg, 0.18 mmol) in methanol (6 mL) was added sodium methoxide (39 mg, 0.73 mmol) and stirred at room temperature for 3 h. The solvent was evaporated and crude product purified by silica gel column chromatography to give 35 mg of (5S,6R,7R,8S)-5-[4-chloro-3-(3,4-dihydro-2H-benzo[1,4]oxazin-6-ylmethyl)-phenyl]-4-oxa-spiro[2.5]octane-6,7,8-triol as a white solid.

$^1$H NMR (400 MHz, $CD_3OD$): δ 0.51-0.55 (m, 1H), 0.70-0.77 (m, 1H), 0.80-0.84 (m, 2H), 3.12-3.3 (m, 2H), 3.25-3.49 (m, 2H), 3.82 (d, J=8.8 Hz, 1H), 3.91 (q, J=14.0 HZ, 2H), 4.12 (d, J=8.8 Hz, 1H), 4.14 (m, 2H), 6.4-6.44 (m, 2H), 6.56 (d, J=7.6 Hz, 1H), 7.1-7.23 (m, 2H), 7.31 (d, J=8.0 Hz, 1H), MS (ES) m/z 418.0 (M+1).

The below list of examples, but not limited to these, can also be synthesized following the general synthesis described herein above:

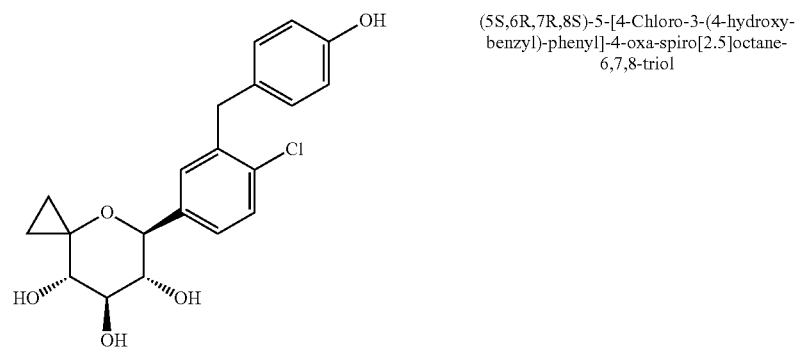

(5S,6R,7R,8S)-5-[4-Chloro-3-(4-hydroxy-benzyl)-phenyl]-4-oxa-spiro[2.5]octane-6,7,8-triol

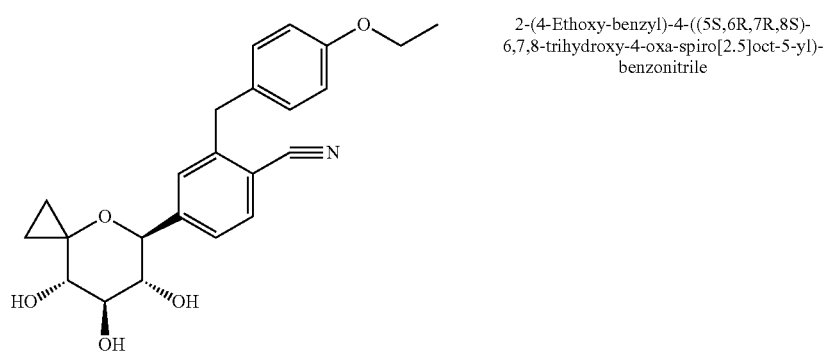

2-(4-Ethoxy-benzyl)-4-((5S,6R,7R,8S)-6,7,8-trihydroxy-4-oxa-spiro[2.5]oct-5-yl)-benzonitrile

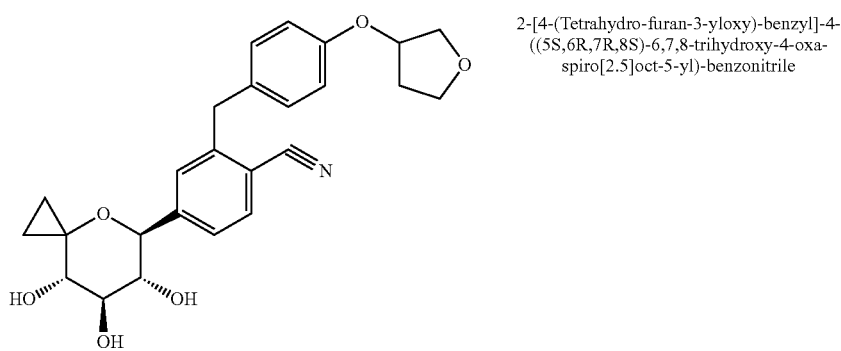
2-[4-(Tetrahydro-furan-3-yloxy)-benzyl]-4-((5S,6R,7R,8S)-6,7,8-trihydroxy-4-oxa-spiro[2.5]oct-5-yl)-benzonitrile
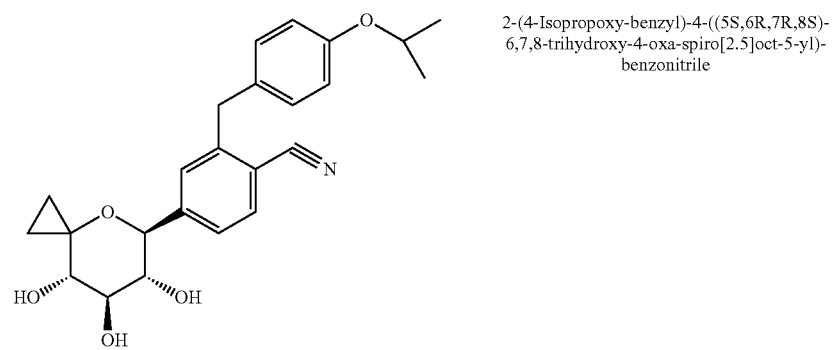
2-(4-Isopropoxy-benzyl)-4-((5S,6R,7R,8S)-6,7,8-trihydroxy-4-oxa-spiro[2.5]oct-5-yl)-benzonitrile
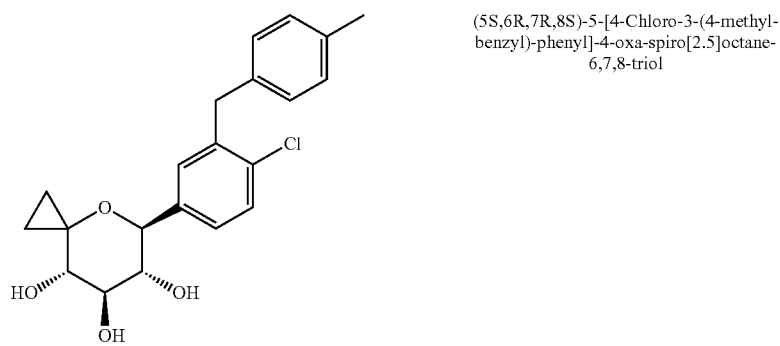
(5S,6R,7R,8S)-5-[4-Chloro-3-(4-methyl-benzyl)-phenyl]-4-oxa-spiro[2.5]octane-6,7,8-triol
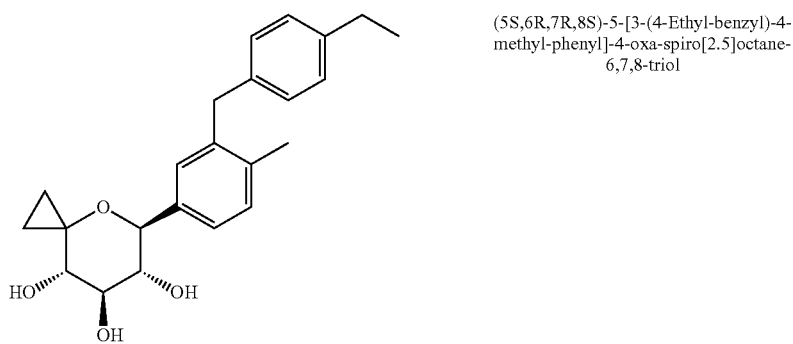
(5S,6R,7R,8S)-5-[3-(4-Ethyl-benzyl)-4-methyl-phenyl]-4-oxa-spiro[2.5]octane-6,7,8-triol

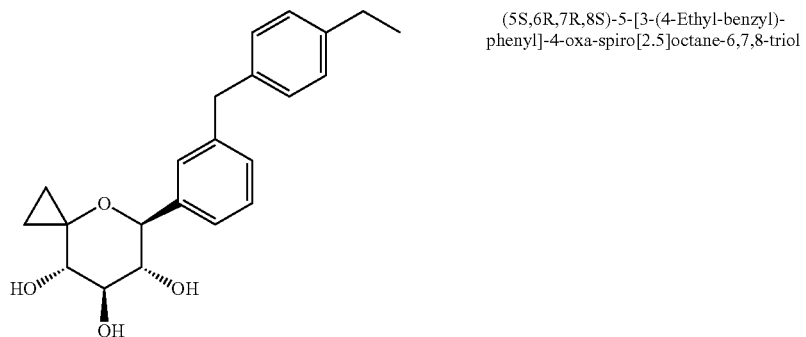
(5S,6R,7R,8S)-5-[3-(4-Ethyl-benzyl)-phenyl]-4-oxa-spiro[2.5]octane-6,7,8-triol
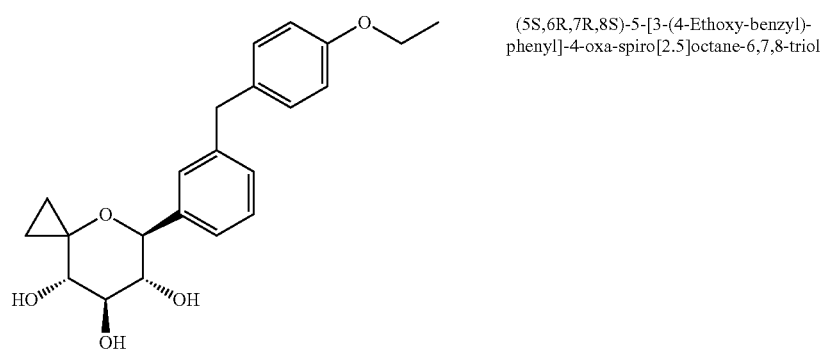
(5S,6R,7R,8S)-5-[3-(4-Ethoxy-benzyl)-phenyl]-4-oxa-spiro[2.5]octane-6,7,8-triol
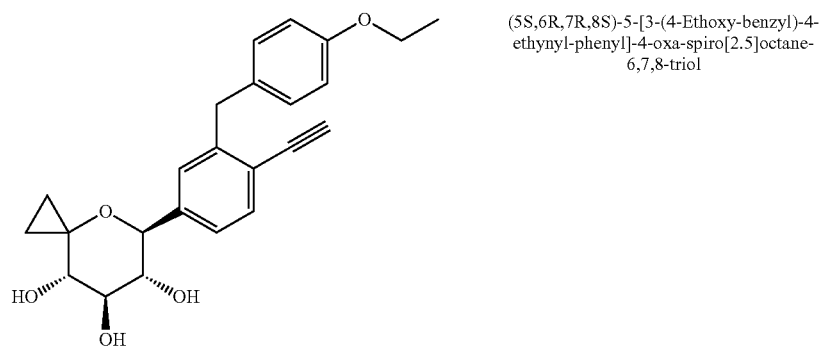
(5S,6R,7R,8S)-5-[3-(4-Ethoxy-benzyl)-4-ethynyl-phenyl]-4-oxa-spiro[2.5]octane-6,7,8-triol
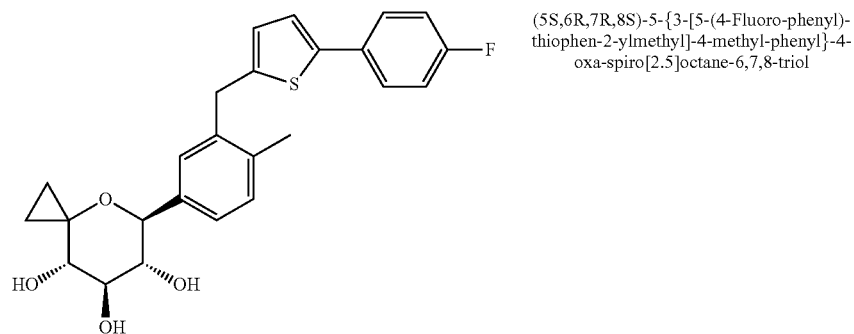
(5S,6R,7R,8S)-5-{3-[5-(4-Fluoro-phenyl)-thiophen-2-ylmethyl]-4-methyl-phenyl}-4-oxa-spiro[2.5]octane-6,7,8-triol

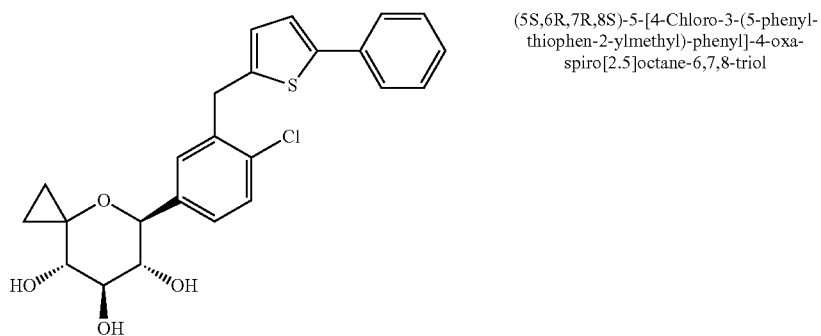
(5S,6R,7R,8S)-5-[4-Chloro-3-(5-phenyl-thiophen-2-ylmethyl)-phenyl]-4-oxa-spiro[2.5]octane-6,7,8-triol
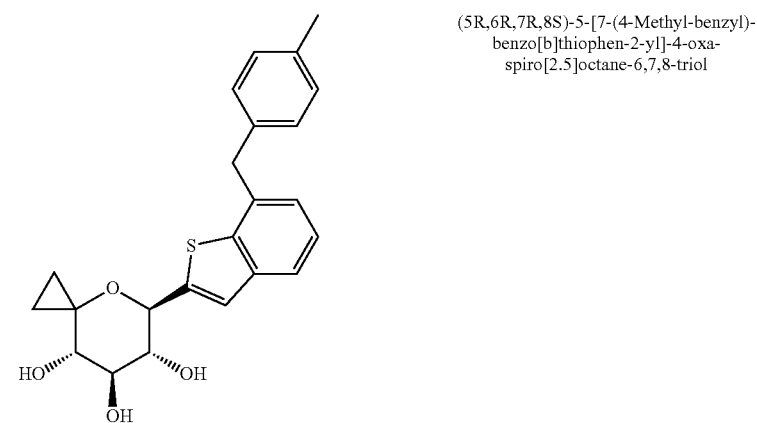
(5R,6R,7R,8S)-5-[7-(4-Methyl-benzyl)-benzo[b]thiophen-2-yl]-4-oxa-spiro[2.5]octane-6,7,8-triol
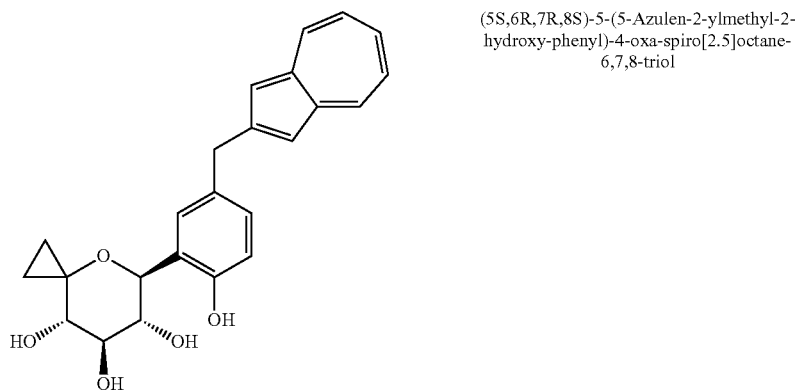
(5S,6R,7R,8S)-5-(5-Azulen-2-ylmethyl-2-hydroxy-phenyl)-4-oxa-spiro[2.5]octane-6,7,8-triol
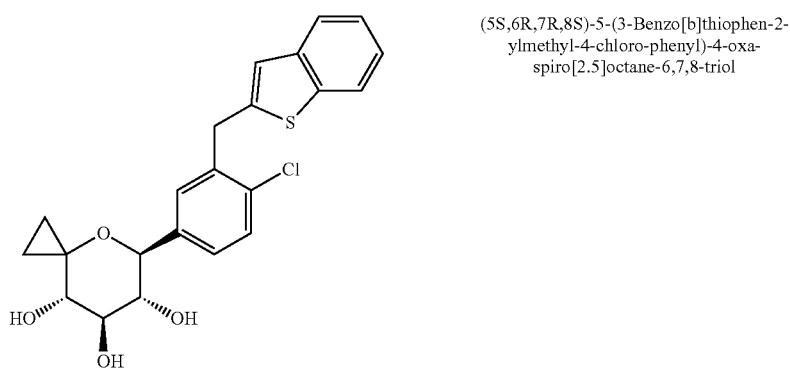
(5S,6R,7R,8S)-5-(3-Benzo[b]thiophen-2-ylmethyl-4-chloro-phenyl)-4-oxa-spiro[2.5]octane-6,7,8-triol -continued
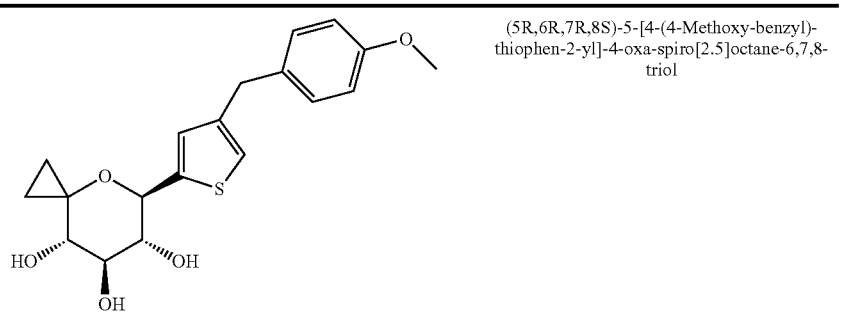
(5R,6R,7R,8S)-5-[4-(4-Methoxy-benzyl)-thiophen-2-yl]-4-oxa-spiro[2.5]octane-6,7,8-triol
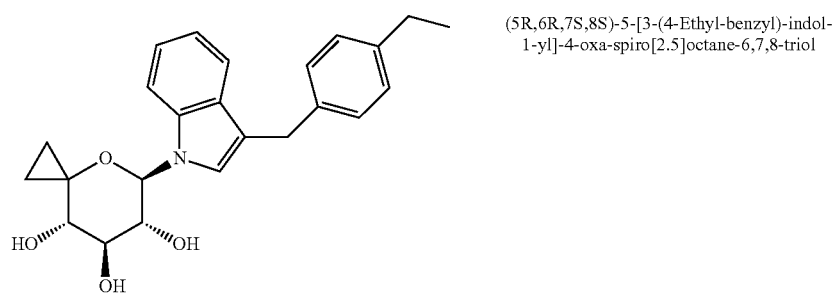
(5R,6R,7S,8S)-5-[3-(4-Ethyl-benzyl)-indol-1-yl]-4-oxa-spiro[2.5]octane-6,7,8-triol
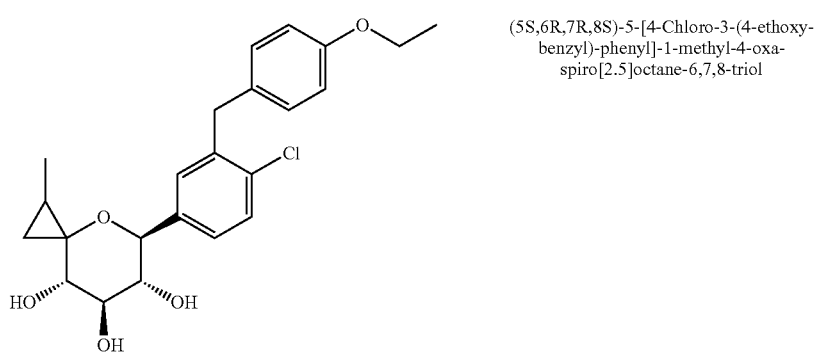
(5S,6R,7R,8S)-5-[4-Chloro-3-(4-ethoxy-benzyl)-phenyl]-1-methyl-4-oxa-spiro[2.5]octane-6,7,8-triol
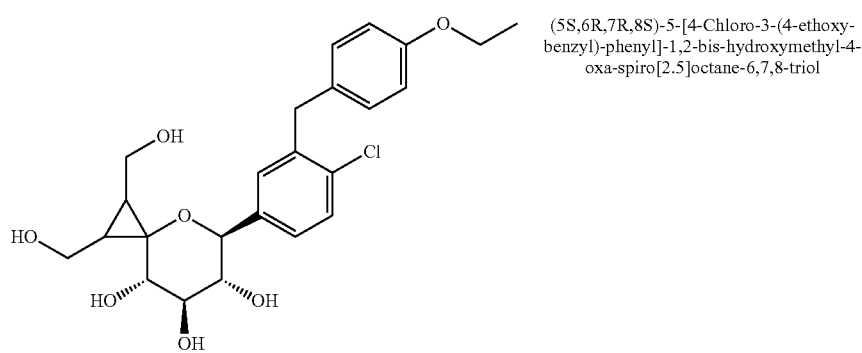
(5S,6R,7R,8S)-5-[4-Chloro-3-(4-ethoxy-benzyl)-phenyl]-1,2-bis-hydroxymethyl-4-oxa-spiro[2.5]octane-6,7,8-triol
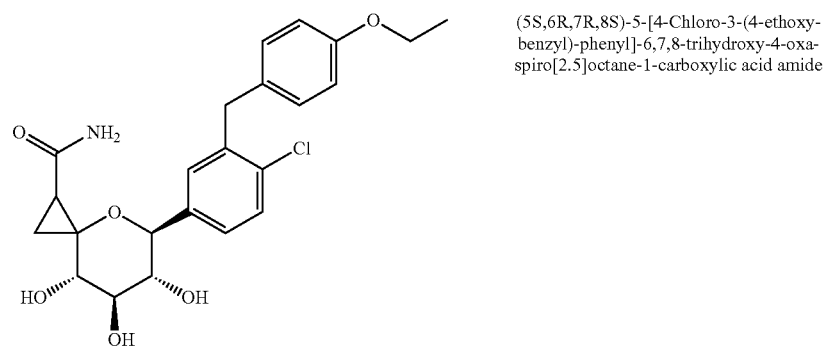
(5S,6R,7R,8S)-5-[4-Chloro-3-(4-ethoxy-benzyl)-phenyl]-6,7,8-trihydroxy-4-oxa-spiro[2.5]octane-1-carboxylic acid amide

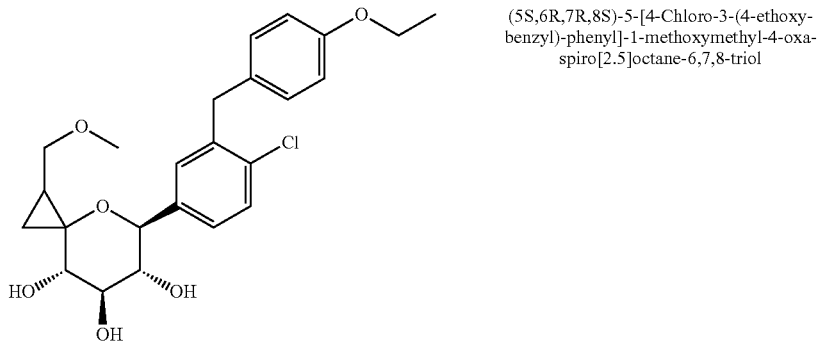
(5S,6R,7R,8S)-5-[4-Chloro-3-(4-ethoxy-benzyl)-phenyl]-1-methoxymethyl-4-oxa-spiro[2.5]octane-6,7,8-triol
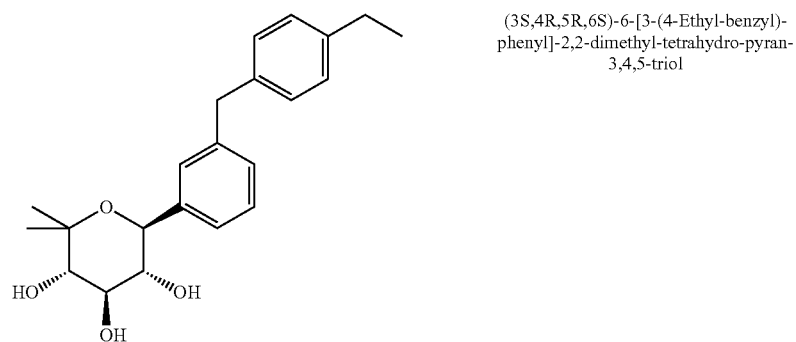
(3S,4R,5R,6S)-6-[3-(4-Ethyl-benzyl)-phenyl]-2,2-dimethyl-tetrahydro-pyran-3,4,5-triol
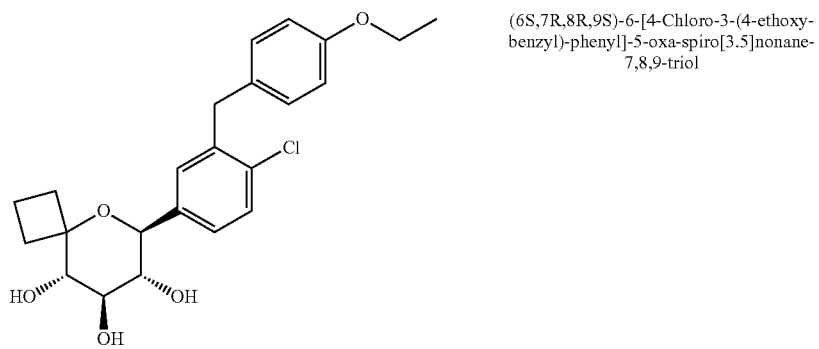
(6S,7R,8R,9S)-6-[4-Chloro-3-(4-ethoxy-benzyl)-phenyl]-5-oxa-spiro[3.5]nonane-7,8,9-triol
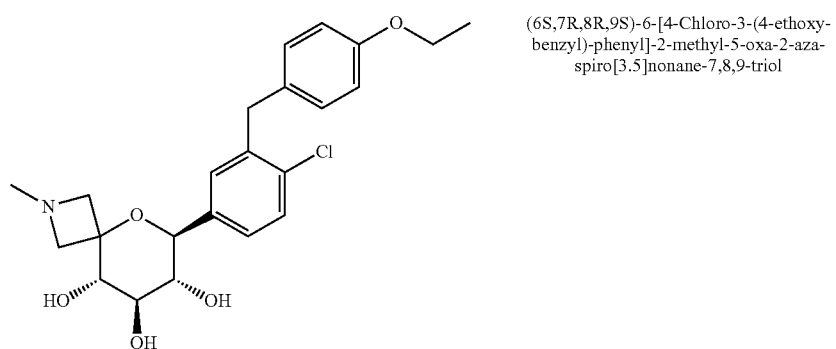
(6S,7R,8R,9S)-6-[4-Chloro-3-(4-ethoxy-benzyl)-phenyl]-2-methyl-5-oxa-2-aza-spiro[3.5]nonane-7,8,9-triol

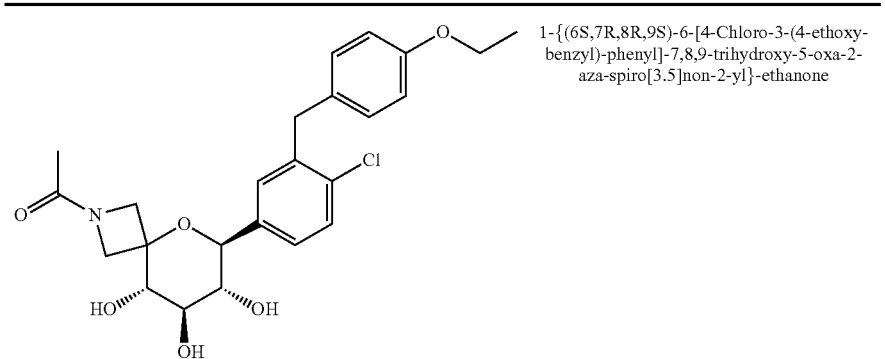
1-{(6S,7R,8R,9S)-6-[4-Chloro-3-(4-ethoxy-benzyl)-phenyl]-7,8,9-trihydroxy-5-oxa-2-aza-spiro[3.5]non-2-yl}-ethanone
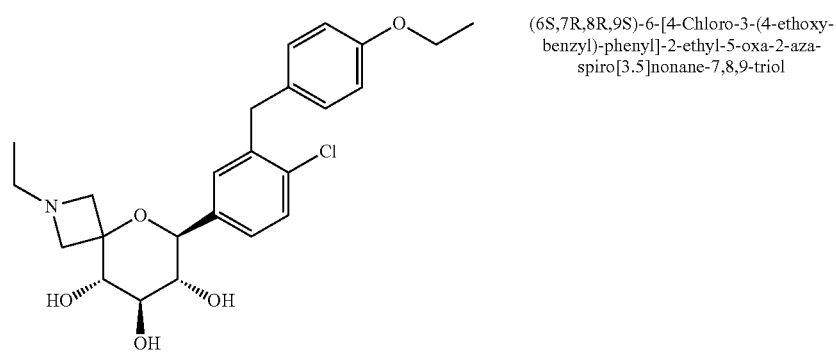
(6S,7R,8R,9S)-6-[4-Chloro-3-(4-ethoxy-benzyl)-phenyl]-2-ethyl-5-oxa-2-aza-spiro[3.5]nonane-7,8,9-triol
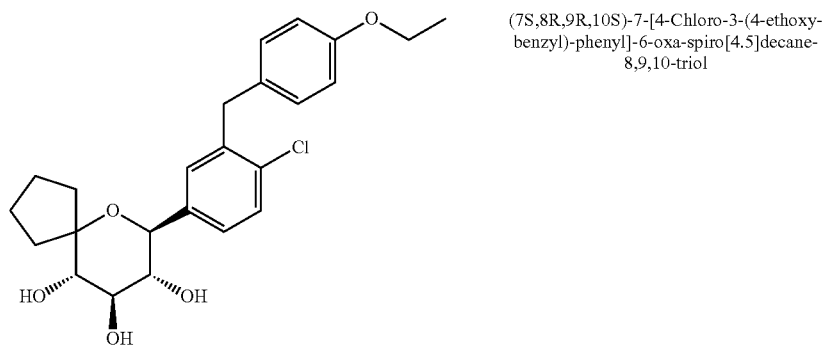
(7S,8R,9R,10S)-7-[4-Chloro-3-(4-ethoxy-benzyl)-phenyl]-6-oxa-spiro[4.5]decane-8,9,10-triol
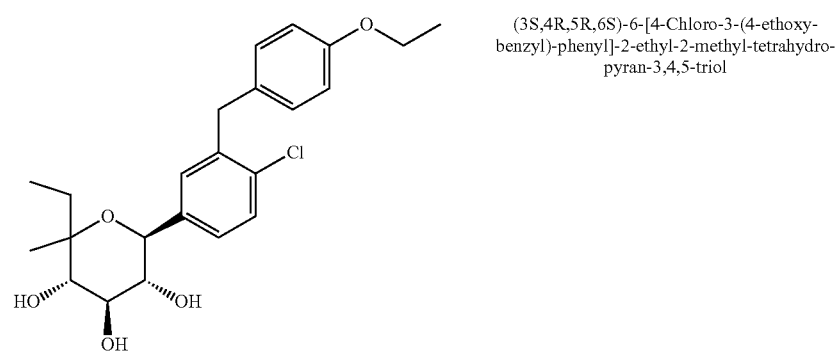
(3S,4R,5R,6S)-6-[4-Chloro-3-(4-ethoxy-benzyl)-phenyl]-2-ethyl-2-methyl-tetrahydro-pyran-3,4,5-triol

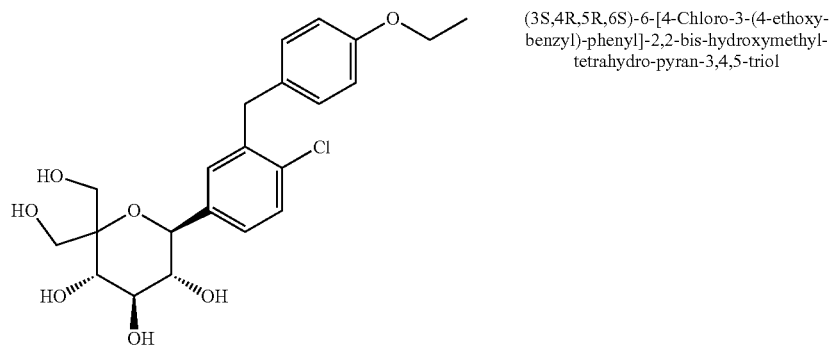
(3S,4R,5R,6S)-6-[4-Chloro-3-(4-ethoxy-benzyl)-phenyl]-2,2-bis-hydroxymethyl-tetrahydro-pyran-3,4,5-triol
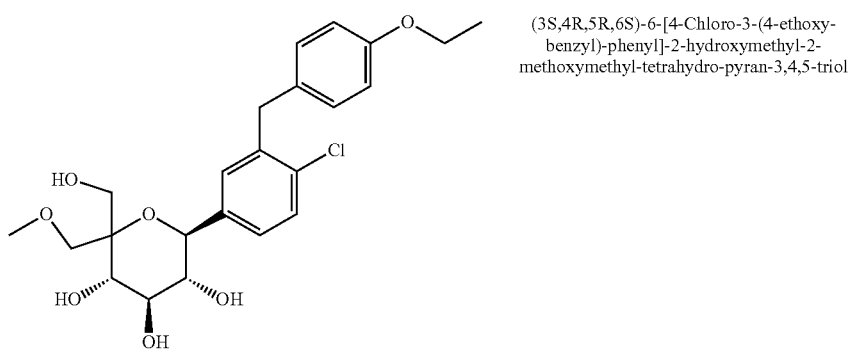
(3S,4R,5R,6S)-6-[4-Chloro-3-(4-ethoxy-benzyl)-phenyl]-2-hydroxymethyl-2-methoxymethyl-tetrahydro-pyran-3,4,5-triol
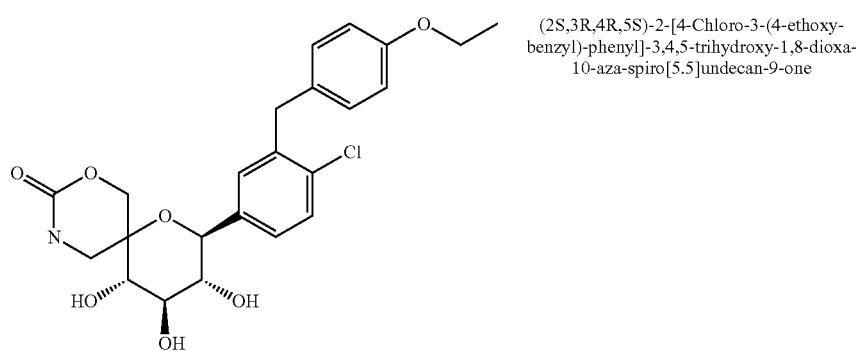
(2S,3R,4R,5S)-2-[4-Chloro-3-(4-ethoxy-benzyl)-phenyl]-3,4,5-trihydroxy-1,8-dioxa-10-aza-spiro[5.5]undecan-9-one
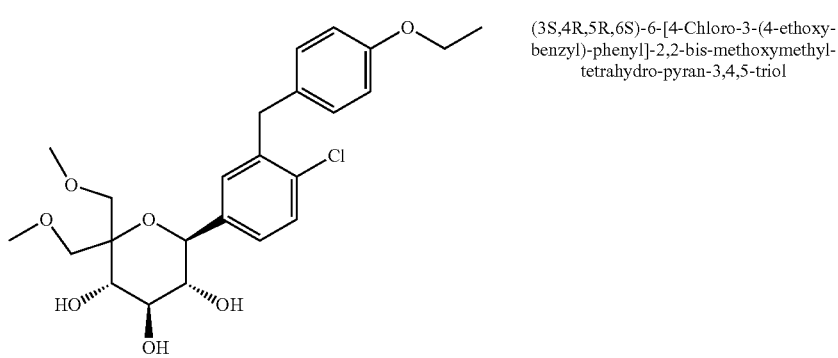
(3S,4R,5R,6S)-6-[4-Chloro-3-(4-ethoxy-benzyl)-phenyl]-2,2-bis-methoxymethyl-tetrahydro-pyran-3,4,5-triol

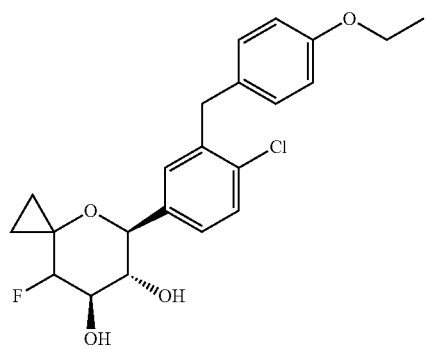 [SMILES: CCOc1ccc(Cc2cc([C@@H]3OC4(CC4)C(F)[C@H](O)[C@H]3O)ccc2Cl)cc1]
(5S,6R,7R)-5-[4-Chloro-3-(4-ethoxy-benzyl)-phenyl]-8-fluoro-4-oxa-spiro[2.5]octane-6,7-diol
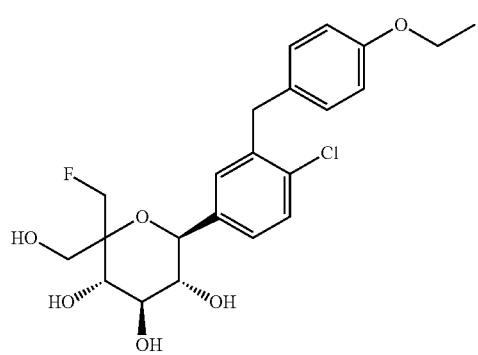 [SMILES: CCOc1ccc(Cc2cc([C@@H]3OC(CO)(CF)[C@@H](O)[C@H](O)[C@H]3O)ccc2Cl)cc1]
(3S,4R,5R,6S)-6-[4-Chloro-3-(4-ethoxy-benzyl)-phenyl]-2-fluoromethyl-2-hydroxymethyl-tetrahydro-pyran-3,4,5-triol
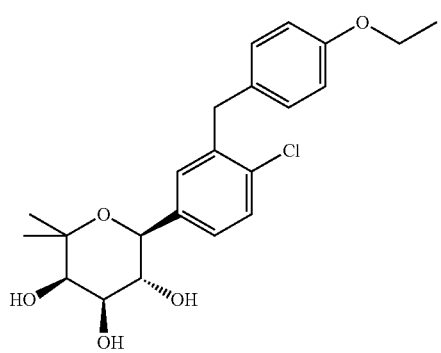 [SMILES: CCOc1ccc(Cc2cc([C@@H]3OC(C)(C)[C@H](O)[C@H](O)[C@H]3O)ccc2Cl)cc1]
(3R,4R,5R,6S)-6-[4-Chloro-3-(4-ethoxy-benzyl)-phenyl]-2,2-dimethyl-tetrahydro-pyran-3,4,5-triol
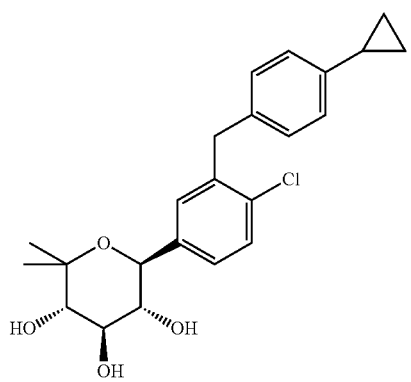 [SMILES: CC1(C)O[C@@H](c2ccc(Cl)c(Cc3ccc(C4CC4)cc3)c2)[C@H](O)[C@@H](O)[C@@H]1O]
(3S,4R,5R,6S)-6-[4-Chloro-3-(4-cyclopropyl-benzyl)-phenyl]-2,2-dimethyl-tetrahydro-pyran-3,4,5-triol

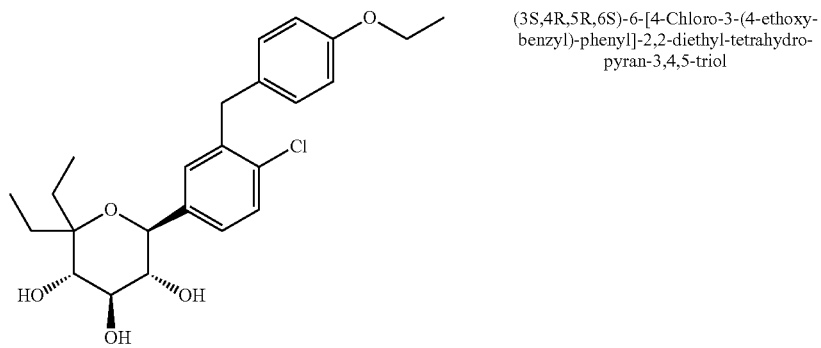
(3S,4R,5R,6S)-6-[4-Chloro-3-(4-ethoxy-benzyl)-phenyl]-2,2-diethyl-tetrahydro-pyran-3,4,5-triol
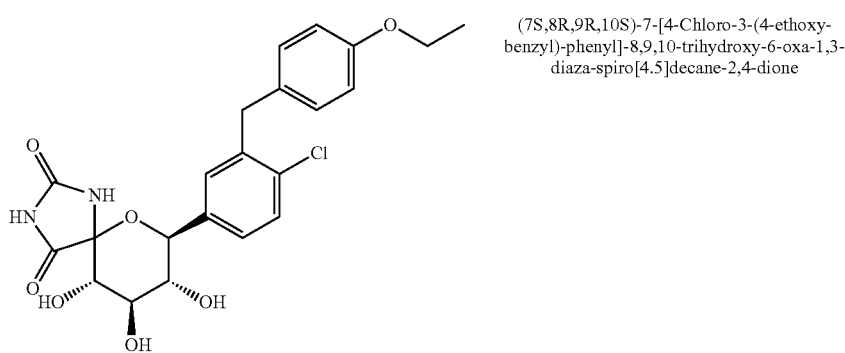
(7S,8R,9R,10S)-7-[4-Chloro-3-(4-ethoxy-benzyl)-phenyl]-8,9,10-trihydroxy-6-oxa-1,3-diaza-spiro[4.5]decane-2,4-dione
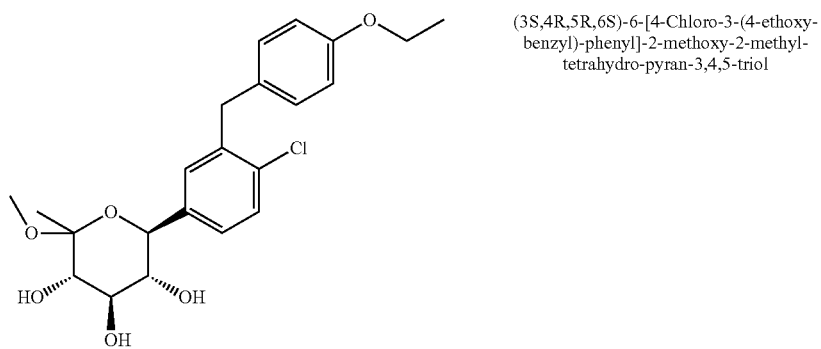
(3S,4R,5R,6S)-6-[4-Chloro-3-(4-ethoxy-benzyl)-phenyl]-2-methoxy-2-methyl-tetrahydro-pyran-3,4,5-triol
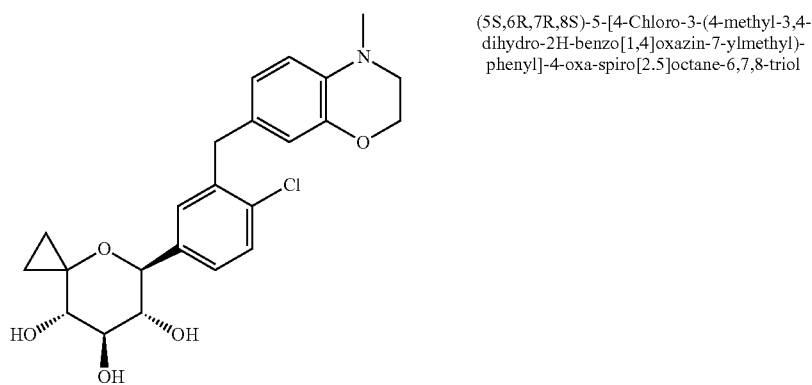
(5S,6R,7R,8S)-5-[4-Chloro-3-(4-methyl-3,4-dihydro-2H-benzo[1,4]oxazin-7-ylmethyl)-phenyl]-4-oxa-spiro[2.5]octane-6,7,8-triol

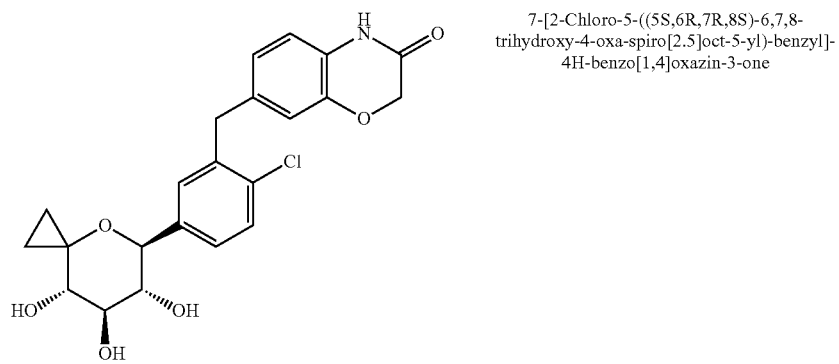
7-[2-Chloro-5-((5S,6R,7R,8S)-6,7,8-trihydroxy-4-oxa-spiro[2.5]oct-5-yl)-benzyl]-4H-benzo[1,4]oxazin-3-one
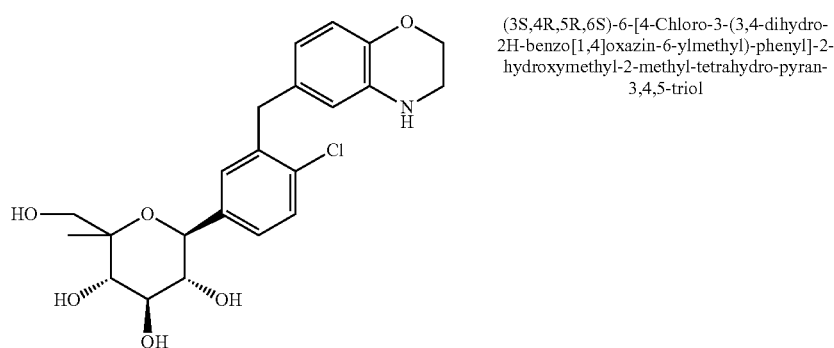
(3S,4R,5R,6S)-6-[4-Chloro-3-(3,4-dihydro-2H-benzo[1,4]oxazin-6-ylmethyl)-phenyl]-2-hydroxymethyl-2-methyl-tetrahydro-pyran-3,4,5-triol
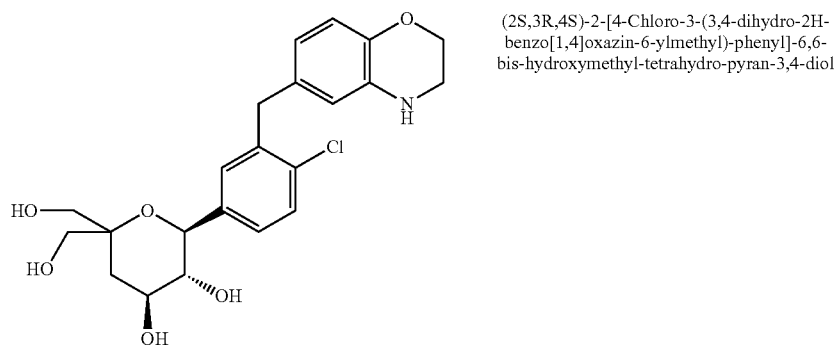
(2S,3R,4S)-2-[4-Chloro-3-(3,4-dihydro-2H-benzo[1,4]oxazin-6-ylmethyl)-phenyl]-6,6-bis-hydroxymethyl-tetrahydro-pyran-3,4-diol
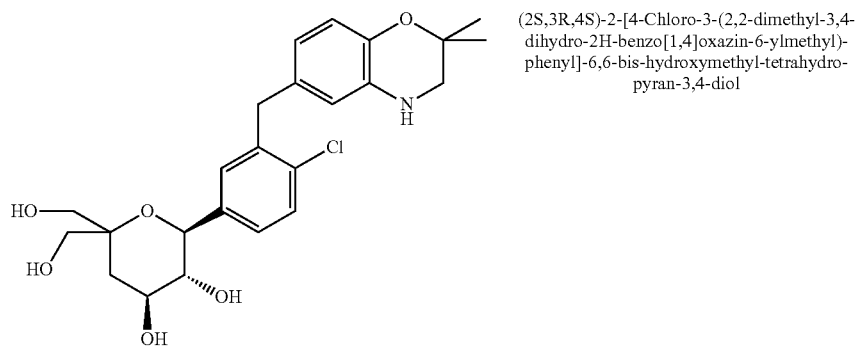
(2S,3R,4S)-2-[4-Chloro-3-(2,2-dimethyl-3,4-dihydro-2H-benzo[1,4]oxazin-6-ylmethyl)-phenyl]-6,6-bis-hydroxymethyl-tetrahydro-pyran-3,4-diol

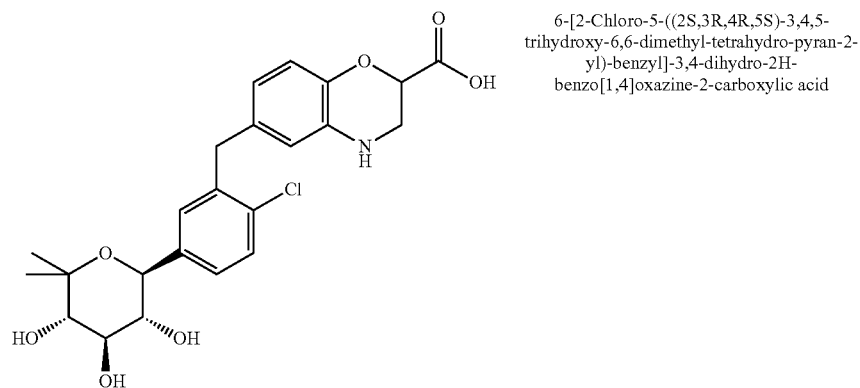

6-[2-Chloro-5-((2S,3R,4R,5S)-3,4,5-trihydroxy-6,6-dimethyl-tetrahydro-pyran-2-yl)-benzyl]-3,4-dihydro-2H-benzo[1,4]oxazine-2-carboxylic acid

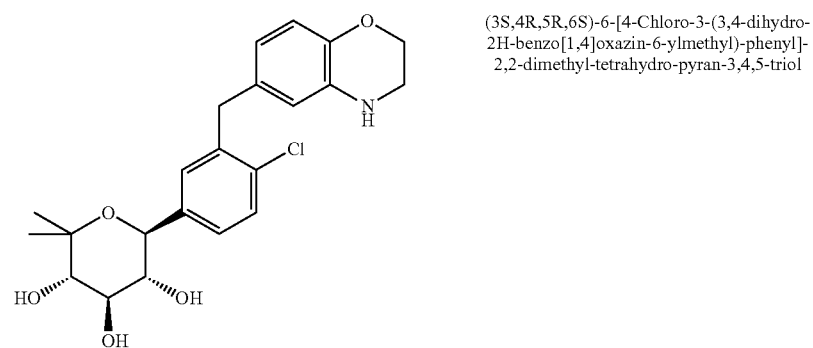

(3S,4R,5R,6S)-6-[4-Chloro-3-(3,4-dihydro-2H-benzo[1,4]oxazin-6-ylmethyl)-phenyl]-2,2-dimethyl-tetrahydro-pyran-3,4,5-triol

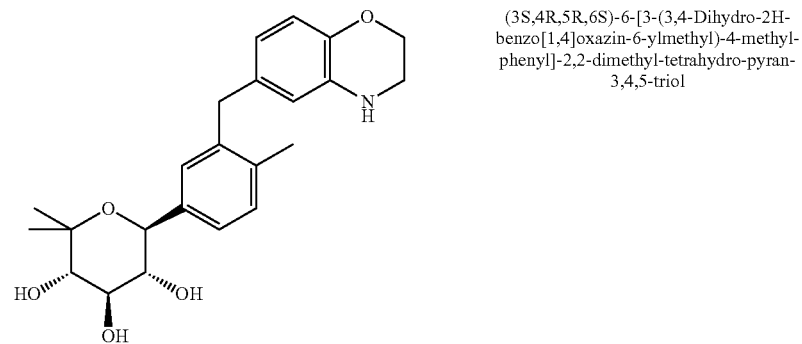

(3S,4R,5R,6S)-6-[3-(3,4-Dihydro-2H-benzo[1,4]oxazin-6-ylmethyl)-4-methyl-phenyl]-2,2-dimethyl-tetrahydro-pyran-3,4,5-triol

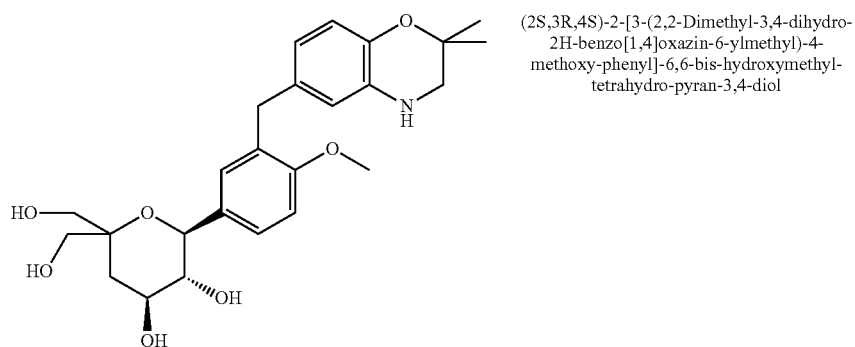

(2S,3R,4S)-2-[3-(2,2-Dimethyl-3,4-dihydro-2H-benzo[1,4]oxazin-6-ylmethyl)-4-methoxy-phenyl]-6,6-bis-hydroxymethyl-tetrahydro-pyran-3,4-diol

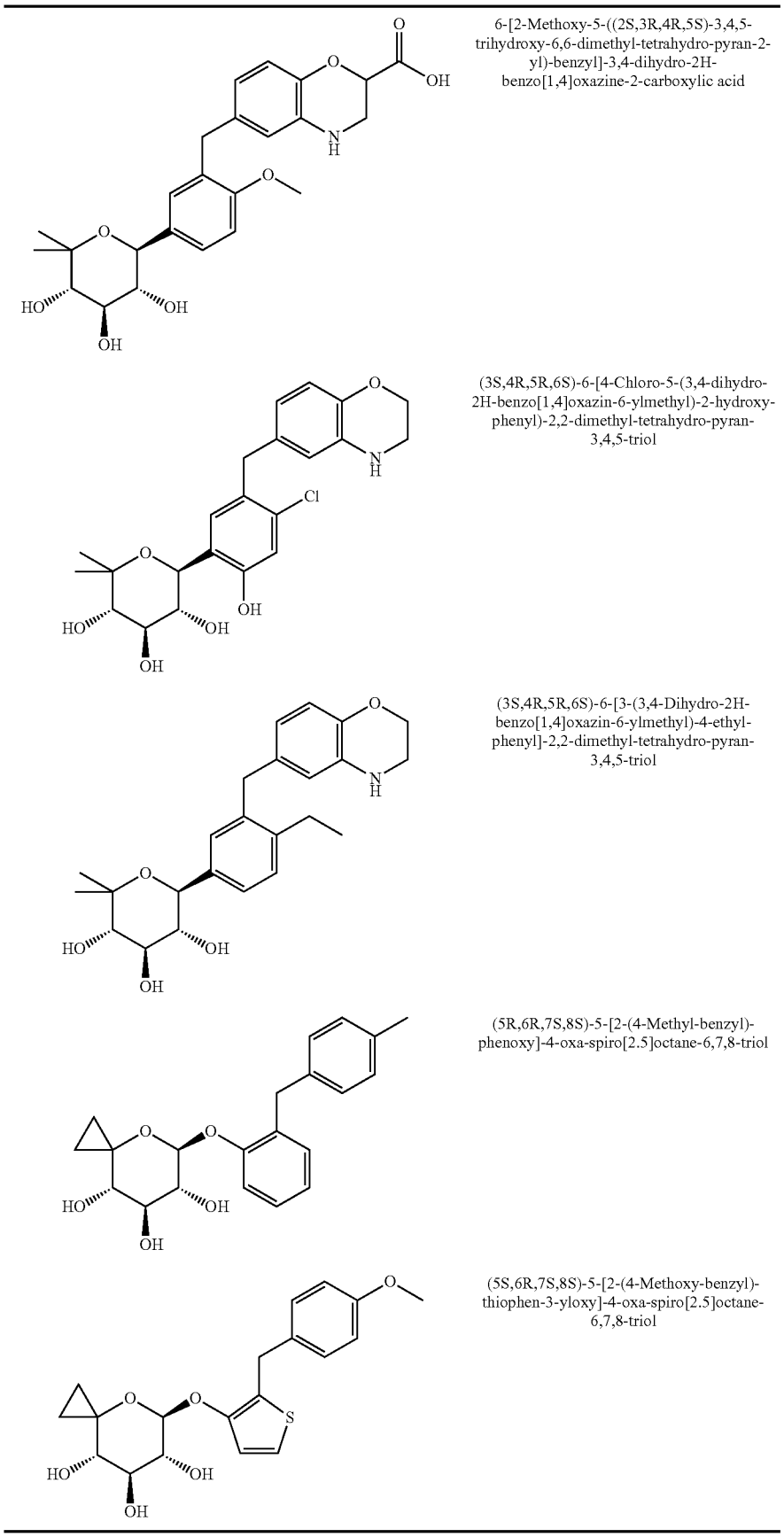

| | |
|---|---|
| | 6-[2-Methoxy-5-((2S,3R,4R,5S)-3,4,5-trihydroxy-6,6-dimethyl-tetrahydro-pyran-2-yl)-benzyl]-3,4-dihydro-2H-benzo[1,4]oxazine-2-carboxylic acid |
| | (3S,4R,5R,6S)-6-[4-Chloro-5-(3,4-dihydro-2H-benzo[1,4]oxazin-6-ylmethyl)-2-hydroxy-phenyl]-2,2-dimethyl-tetrahydro-pyran-3,4,5-triol |
| | (3S,4R,5R,6S)-6-[3-(3,4-Dihydro-2H-benzo[1,4]oxazin-6-ylmethyl)-4-ethyl-phenyl]-2,2-dimethyl-tetrahydro-pyran-3,4,5-triol |
| | (5R,6R,7S,8S)-5-[2-(4-Methyl-benzyl)-phenoxy]-4-oxa-spiro[2.5]octane-6,7,8-triol |
| | (5S,6R,7S,8S)-5-[2-(4-Methoxy-benzyl)-thiophen-3-yloxy]-4-oxa-spiro[2.5]octane-6,7,8-triol |

The inhibitory effect on the sodium-dependent glucose cotransporter SGLT, SGLT1 and SGLT2, of compounds of formula I may be demonstrated using the following test procedures:

The ability of the substances to inhibit the SGLT-2 activity may be demonstrated in a test set-up in which a CHO-K1 cell line (ATCC No. CCL 6 1) or alternatively an HEK293 cell line (ATCC No. CRL-1573), which is stably transfected with an expression vector pZeoSV (Invitrogen, EMBL accession number L36849), which contains the cDNA for the coding sequence of the human sodium glucose cotransporter 2 (Genbank Acc. No. NM_003041) (CHO-hSGLT2 or HEK-hSGLT2). These cell lines transport 14 C-labeled alpha-methyl-glucopyranoside (14 C-AMG, Amersham) into the interior of the cell in sodium-dependent manner.

The SGLT-2 assay is carried out as follows: CHO-hSGLT2 cells are cultivated in Ham's F12 Medium (BioWhittaker) with 10% fetal calf serum and 250 µg/mL zeocin (Invitrogen), and HEK293-hSGLT2 cells are cultivated in DMEM medium with 10% fetal calf serum and 250 µg/mL zeocin (Invitrogen). The cells are detached from the culture flasks by washing twice with PBS and subsequently treating with trypsin/EDTA. After the addition of cell culture medium the cells are centrifuged, resuspended in culture medium and counted in a Casy cell counter. Then 40,000 cells per well are seeded into a white, 96-well plate coated with poly-D-lysine and incubated overnight at 37° C., 5% CO2. The cells are washed twice with 250 µl of assay buffer (Hanks Balanced Salt Solution, 137 mM NaCl, 5.4 mM KCl, 2.8 mM CaCl2, 1.2 mM MgSO4 and 10 mM HEPES (pH 7.4), 50 µg/mL of gentamycin). 250 µl of assay buffer and 5 µl of test compound are then added to each well and the plate is incubated for a further 15 minutes in the incubator. 5 µl of 10% DMSO are used as the negative control. The reaction is started by adding 5 µl of 14 C-AMG (0.05 µCi) to each well. After 2 hours' incubation at 37° C., 5% CO2, the cells are washed again with 250 µl of PBS (200 C) and then lysed by the addition of 25 µl of 0.1 N NaOH (5 min. at 37° C.). 200 µl of MicroScint20 (Packard) are added to each well and incubation is continued for a further 20 min at 37° C. After this incubation the radioactivity of the 14 C-AMG absorbed is measured in a Topcount (Packard) using a 14 C scintillation program.

To determine the selectivity with respect to human SGLT1 an analogous test is set up in which the cDNA for hSGLTI (Genbank Acc. No. NM000343) instead of hSGLT2 cDNA is expressed in CHO-K1 or HEK293 cells.

The compounds according to the invention may for example have EC50 values below 1000 nM, particularly below 100 nM, most preferably below 10 nM.

The title compounds of the above Examples were evaluated in the above described assay and the results of which are collated in Table 1.

TABLE 1

| Example Number | SGLT2 IC$_{50}$ nM (n = 1-4) | SGLT1 IC$_{50}$ nM (n = 1-4) |
|---|---|---|
| 1 | 1.1 | 370 |
| 2 | 1 | 300 |
| 3 | 0.9 | 153 |
| 4 | 4.2 | 1215 |
| 5 | 5.2 | 3225 |
| 6 | 2.6 | 460 |
| 7 | 3.2 | 700 |
| 10 | 23 | >30000 |

It can be seen that the compounds of the invention are useful as inhibitors of SGLT2 and therefore useful in the treatment of diseases and conditions mediated by SGLT2 such as the metabolic disorders disclosed herein.

It will be understood that the invention has been described by way of example only and modifications may be made whilst remaining within the scope and spirit of the invention.

We claim:
1. A compound represented by Formula (I):

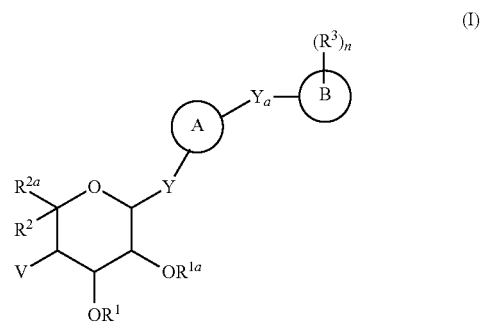

Ring A is an $C_{6-10}$aryl or a 5- to 10-membered heteroaryl; wherein the aryl or the heteroaryl is optionally substituted with one or more substituents independently selected from the group consisting of a halo, hydroxy, cyano, $C_{1-6}$alkyl, $C_{3-7}$cycloalkyl, $C_{2-6}$alkenyl, $C_{2-6}$alkynyl, $C_{1-6}$alkoxy, halo$C_{1-6}$alkoxy, a 5-membered heteroaryl and a 6-membered heteroaryl;

Ring B is a $C_{6-10}$aryl or a $C_{1-10}$heteroaryl;

Y is a direct bond or O;

$Y_a$ is a bond or a ($C_1$-$C_6$)alkylene which is optionally substituted with one or more substituents independently selected from halo, $C_{1-4}$alkyl, halo$C_{1-4}$alkyl;

V is hydrogen, halo or —OR$^{1b}$;

$R^1$, $R^{1a}$, and $R^{1b}$ are independently selected from hydrogen, $C_{1-6}$ alkyl, $C_{6-10}$aryl-$C_{1-4}$alkyl, —C(O)$C_{6-10}$aryl or —C(O)$C_{1-6}$alkyl;

$R^2$ and $R^{2a}$ are independently selected from the group consisting of $C_{1-6}$alkyl, and $C_{1-6}$alkoxy, wherein the alkyl and the alkoxy may be optionally substituted with one or more substituents which are independently selected from halo, hydroxy, $C_{1-4}$alkyl, and $C_{1-4}$alkoxy; provided that Y is a direct bond when $R^2$ and $R^{2a}$ are an optionally substituted alkyl; or $R^2$ and $R^{2a}$ taken together with the carbon to which they are attached may form a spiro 3- to 7-membered heterocyclyl or a spiro $C_{3-7}$cycloalkyl which may be optionally substituted with one or more substituents independently selected from halo, hydroxy, oxo, $C_{1-4}$alkyl, hydroxy$C_{1-4}$ alkyl, $C_{1-4}$alkoxy, $C_{1-4}$alkoxy$C_{1-4}$alkyl, halo$C_{1-4}$alkyl, $C_{1-6}$alkanoyl, carbamoyl, N—($C_{1-4}$alkyl)-carbamoyl, and N,N-di-($C_{1-4}$alkyl)-carbamoyl; and $R^3$, for each occurrence, is independently selected from the group consisting of halo, hydroxy, cyano, nitro, oxo, $C_{1-6}$alkyl, $C_{3-7}$cycloalkyl, $C_{3-7}$cycloalkyl$C_{1-4}$alkyl, $C_{6-10}$aryl, $C_{6-10}$aryl$C_{1-4}$alkyl, —C(O)OR$^6$, —C(O)R$^6$, —C(O)NR$^4$R$^5$, —NR$^4$R$^5$, —CH$_2$NR$^4$R$^5$, $C_{1-6}$ alkoxy, $C_{3-7}$cycloalkoxy, —S(O)$_p$R$^6$, —S(O)$_2$NR$^4$R$^5$, —OS(O)$_2$R$^6$, —CH$_2$C(O)OR$^6$, —CH$_2$C(O)NR$^4$R$^5$, —NR$^6$C(O)NR$^4$R$^5$, —NR$^6$C(O)OR$^6$, $C_{6-10}$aryloxy, $C_{2-10}$heterocyclyl, $C_{2-10}$heterocyclyl$C_{1-4}$alkyl, $C_{1-10}$heteroaryl$C_{1-4}$alkyl, $C_{1-10}$heteroaryl, $C_{1-10}$heteroaryloxy, or $C_{1-10}$heterocycloxy; wherein R$^3$ may, for each occurrence, be optionally substituted with one or more substituents which are independently selected from halo, hydroxy, $C_{1-4}$alkyl, and $C_{1-4}$alkoxy;

$R^6$, for each occurrence, is independently selected from hydrogen, $C_{1-6}$ alkyl, $C_{3-7}$ cycloalkyl, $C_{3-7}$ cycloalkyl$C_{1-4}$alkyl, $C_{6-10}$aryl, $C_{1-10}$heteroaryl, and $C_{2-10}$heterocyclyl;

$R^4$ and $R^5$, for each occurrence, are independently selected from hydrogen, $C_{1-6}$ alkyl, $C_{3-7}$ cycloalkyl, $C_{3-7}$ cycloalkyl$C_{1-4}$alkyl, $C_{6-10}$aryl$C_{1-4}$alkyl, $C_{6-10}$aryl, $C_{1-10}$heteroaryl, $C_{1-10}$heteroaryl$C_{1-4}$alkyl, $C_{2-10}$heterocyclyl, and $C_{2-10}$heterocyclyl$C_{1-4}$alkyl; or $R^4$ and $R^5$ taken together along with the nitrogen to which they are bound may form a monocyclic or a bicyclic heteroaryl or heterocyclyl which may be optionally substituted with one or more halo or $C_{1-4}$alkyl;

n is 0, 1, 2, 3, or 4;

or a pharmaceutically acceptable salt thereof.

2. The compound of claim 1, or a pharmaceutically acceptable salt thereof, wherein $R^2$ and $R^{2a}$ are selected from one of structures i to xix; wherein the black dot represents the point of attachment to the tetrahydropyran ring:

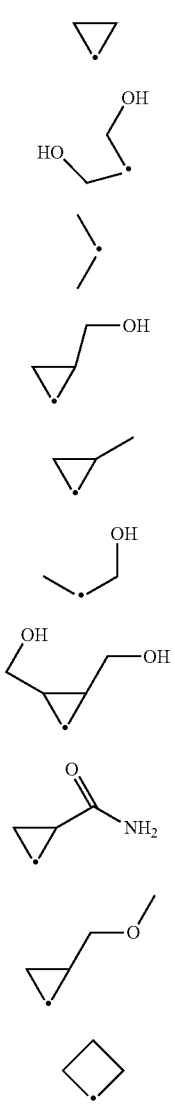

xi

xii

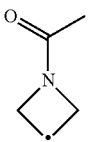

xiii

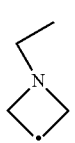

xiv

xv

xvi

xvii

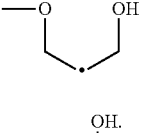

xvii

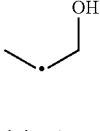

xix

3. The compound of claim 1, or a pharmaceutically acceptable salt thereof, wherein Ring A is indolyl, thiophenyl, benzothiophenyl or $C_{6-10}$aryl; wherein the indolyl, thiophenyl, benzothiophenyl or $C_{6-10}$aryl may be optionally substituted with one or more substituents which are independently selected from halo, hydroxy, cyano, $C_{1-6}$alkyl, $C_{3-7}$cycloalkyl, $C_{2-6}$alkenyl, $C_{2-6}$alkynyl, $C_{1-6}$alkoxy, halo$C_{1-6}$alkoxy, a 5-membered heteroaryl and a 6-membered heteroaryl.

4. The compound of claim 1, or a pharmaceutically acceptable salt thereof, wherein Ring B is a $C_{6-10}$aryl.

5. The compound of claim 1, or a pharmaceutically acceptable salt thereof, wherein Ring B is a $C_{1-10}$ heteroaryl.

6. The compound of claim 1, or a pharmaceutically acceptable salt thereof, wherein Ring B is bicyclic.

7. The compound of claim 4, wherein the compound is represented by Formula (IA):

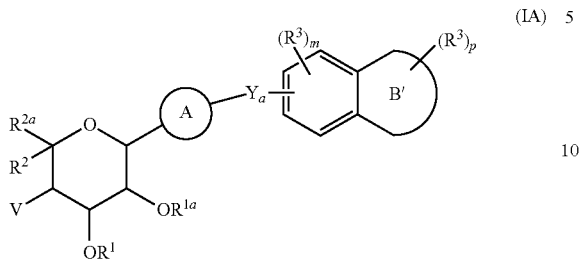

(IA)

Ring B' is a 5- or 6-membered heterocycyl;
m is 0, 1, 2, 3, or 4; and
p is 0, 1, 2, 3, or 4, provided that m+p is not greater than 4;
or a pharmaceutically acceptable salt thereof.

8. The compound of claim 1, or a pharmaceutically acceptable salt thereof, wherein Ring B is monocyclic.

9. The compound of claim 1, or a pharmaceutically acceptable salt thereof, wherein n is 0, 1 or 2 and, if present, m+p does not exceed the value of n.

10. The compound of claim 1, or a pharmaceutically acceptable salt thereof, wherein $R^3$, for each occurrence, is independently selected from the group consisting of halo, hydroxy, cyano, nitro, oxo, $C_{1-6}$alkyl, $C_{3-7}$cycloalkyl, $C_{6-10}$aryl, $C_{6-10}$aryl$C_{1-4}$alkyl, —C(O)OR$^6$, —C(O)R$^6$, —C(O)NR$^4$R$^5$, —NR$^4$R$^5$, —CH$_2$NR$^4$R$^5$, $C_{1-6}$alkoxy, $C_{3-7}$cycloalkoxy, —CH$_2$C(O)OR$^6$, —CH$_2$C(O)NR$^4$R$^5$, —NR$^6$C(O)NR$^4$R$^5$, —NR$^6$C(O)OR$^6$, $C_{6-10}$aryloxy, $C_{2-10}$heterocyclyl, $C_{1-10}$heteroaryl, $C_{1-10}$heteroaryloxy and $C_{1-10}$heterocycloxy; wherein $R^3$ may, for each occurrence, be optionally substituted with one or more substituents which are independently selected from halo, hydroxy, $C_{1-4}$alkyl, and $C_{1-4}$alkoxy.

11. A compound of claim 1, selected from the group consisting of:
(6S,7R,8S)-6,7,8-tris(benzyloxy)-5-(4-chloro-3-(4-ethoxybenzyl)phenyl)-4-oxaspiro[2.5]octane,
(5S,6R,7R,8S)-5-[4-Chloro-3-(4-ethoxy-benzyl)-phenyl]-4-oxa-spiro[2.5]octane-6,7,8-triol,
(5S,6R,7R,8S)-5-[3-(4-Ethoxy-benzyl)-4-methyl-phenyl]-4-oxa-spiro[2.5]octane-6,7,8-triol,
Acetic acid (5S,6S,7R,8S)-7,8-diacetoxy-5-[4-chloro-3-(4-ethoxy-benzyl)-phenyl]-4-oxa-spiro[2.5]oct-6-yl ester,
Acetic acid (5S,6S,7R,8S)-7,8-diacetoxy-5-[4-chloro-3-(4-hydroxy-benzyl)-phenyl]-4-oxa-spiro[2.5]oct-6-yl ester,
(5S,6R,7R,8S)-5-[4-Chloro-3-(4-hydroxy-benzyl)-phenyl]-4-oxa-spiro[2.5]octane-6,7,8-triol,
(5S,6S,7R,8S)-5-(4-chloro-3-(4-((S)-tetrahydrofuran-3-yloxy)benzyl)phenyl)-4-oxaspiro[2.5]octane-6,7,8-triyl triacetate,
(5S,6R,7R,8S)-5-(4-Chloro-3-{4-[(S)-(tetrahydro-furan-3-yl)oxy]-benzyl}-phenyl)-4-oxa spiro[2.5]octane-6,7,8-triol,
((3S,4R,5S,6S)-3,4,5-tris(benzyloxy)-6-(4-chloro-3-(4-ethoxybenzyl)phenyl)tetrahydro-2H-pyran-2,2-diyl)dimethanol,
(3S,4R,5R,6S)-6-[4-Chloro-3-(4-ethoxy-benzyl)-phenyl]-2,2-bis-hydroxymethyl-tetrahydro-pyran-3,4,5-triol,
(3S,4R,5R,6S)-6-[4-chloro-3-(4-ethoxy-benzyl)-phenyl]-2,2-dimethyl-tetrahydro-pyran-3,4,5-triol,
{(5S,6S,7R,8S)-6,7,8-Tris-benzyloxy-5-[4-chloro-3-(4-ethoxy-benzyl)-phenyl]-4-oxa-spiro[2.5]oct-1-yl}-methanol,
{(5S,6S,7R,8S)-6,7,8-Tris-benzyloxy-5-[3-(4-ethoxy-benzyl)-phenyl]-4-oxa-spiro[2.5]oct-1-yl}-methanol,
(5S,6R,7R,8S)-5-[4-Chloro-3-(4-ethoxy-benzyl)-phenyl]-1-hydroxymethyl-4-oxa-spiro[2.5]octane-6,7,8-triol,
(5S,6R,7R,8S)-5-[3-(4-Ethoxy-benzyl)-phenyl]-1-hydroxymethyl-4-oxa-spiro[2.5]octane-6,7,8-triol,
((3S,4S,5R,6S)-3,4,5-tris(benzyloxy)-6-(3-(4-ethylbenzyl)-1H-indol-1-yl)tetrahydro-2H-pyran-2,2-diyl)dimethanol,
(3S,4S,5R)-6-[(R)-3-(4-Ethyl-benzyl)-indol-1-yl]-2,2-bis-hydroxymethyl-tetrahydro-pyran-3,4,5-triol,
(6R,7S,8S)-6,7,8-tris(benzyloxy)-5-(2-(4-methoxybenzyl)phenoxy)-4-oxaspiro[2.5]octane,
(5R,6R,7S,8S)-5-[2-(4-Methoxy-benzyl)-phenoxy]-4-oxa-spiro[2.5]octane-6,7,8-triol,
(3S,4R,5R,6S)-6-[4-Chloro-3-(3,4-dihydro-2H-benzo[1,4]oxazin-6-ylmethyl)-phenyl]-2,2-bis-hydroxymethyl-tetrahydro-pyran-3,4,5-triol,
(3S,4R,5R,6S)-6-[3-(4-Ethoxy-benzyl)-4-methoxy-phenyl]-2,2-bis-hydroxymethyl-tetrahydro-pyran-3,4,5-triol,
(3S,4R,5R,6S)-6-(3-Chroman-6-ylmethyl-4-ethyl-phenyl)-2,2-bis-hydroxymethyl-tetrahydro-pyran-3,4,5-triol,
(5S,6R,7R,8S)-5-[3-(2,3-Dihydro-benzo[1,4]dioxin-6-ylmethyl)-4-ethyl-phenyl]-4-oxa-spiro[2.5]octane-6,7,8-triol,
(5S,6R,7R,8S)-5-[4-Cyclopropyl-3-(2,3-dihydro-benzo[1,4]dioxin-6-ylmethyl)-phenyl]-4-oxa-spiro[2.5]octane-6,7,8-triol,
(5S,6R,7R,8S)-5-[4-Bromo-3-(2,3-dihydro-benzo[1,4]dioxin-6-ylmethyl)-phenyl]-4-oxa-spiro[2.5]octane-6,7,8-triol,
(5S,6R,7R,8S)-5-[4-Chloro-3-(2,3-dihydro-benzo[1,4]dioxin-6-ylmethyl)-phenyl]-4-oxa-spiro[2.5]octane-6,7,8-triol,
(5S,6R,7R,8S)-5-(4-Chloro-3-chroman-6-ylmethyl-phenyl)-4-oxa-spiro[2.5]octane-6,7,8-triol,
(5S,6R,7R,8S)-5-[3-(4-Ethoxy-benzyl)-4-methoxy-phenyl]-4-oxa-spiro[2.5]octane-6,7,8-triol,
{(3S,4R,5S,6S)-3,4,5-tris-benzyloxy-6-[4-chloro-3-(4-ethoxy-benzyl)-phenyl]-2-methyl-tetrahydro-pyran-2-yl}-methanol,
(3S,4R,5R,6S)-6-[4-chloro-3-(4-ethoxy-benzyl)-phenyl]-2-hydroxymethyl-2-methyl-tetrahydro-pyran-3,4,5-triol,
(3S,4R,5S,6S)-3,4,5-tris-benzyloxy-6-[4-chloro-3-(4-ethoxy-benzyl)-phenyl]-2-hydroxymethyl-tetrahydro-pyran-2-ol,
(3S,4R,5R,6S)-6-[4-Chloro-3-(4-ethoxy-benzyl)-phenyl]-2-hydroxymethyl-tetrahydro-pyran-2,3,4,5-tetraol,
(3S,4R,5R,6S)-6-[4-Chloro-3-(4-ethoxy-benzyl)-phenyl]-2-hydroxymethyl-2-methoxy-tetrahydro-pyran-3,4,5-triol,
(6S,7S,8R,9S)-7,8,9-tris-benzyloxy-6-[4-chloro-3-(4-ethoxy-benzyl)-phenyl]-2,5-dioxa-spiro[3.5]nonane,
(6S,7R,8R,9S)-6-[4-chloro-3-(4-ethoxy-benzyl)-phenyl]-2,5-dioxa-spiro[3.5]nonane-7,8,9-triol, (6S,7R,8R,9S)-6-(3-Chroman-6-ylmethyl-4-ethyl-phenyl)-2,5-dioxa-spiro[3.5]nonane-7,8,9-triol, (5S,6S,7R,8S)-5-(4-chloro-3-(4-(pyrrolidin-1-yl)benzyl)phenyl)-4-oxaspiro[2.5]octane-6,7,8-triyl triacetate, (5S,6R,7R,8S)-5-[4-chloro-3-(4-pyrrolidin-1-yl-benzyl)-phenyl]-4-oxa-spiro[2.5]octane-6,7,8-triol, (5S,6R,7R,8S)-5-{3-[4-(Benzyl-ethyl-amino)-benzyl]-4-chloro-phenyl}-4-oxa-spiro[2.5]octane-6,7,8-triol, (5S,6R,7R,8S)-5-[4-Chloro-3-(4-ethylamino-benzyl)-phenyl]-4-oxa-spiro[2.5]octane-6,7,8-triol, (5S,6R,7R,8S)-5-[4-chloro-3-(3,4-dihydro-2H-benzo[1,4]oxazin-6-ylmethyl)-phenyl]-4-oxa-spiro[2.5]octane-6,7,8-triol, Acetic acid (5S,6S,7R,8S)-7,8-diacetoxy-5-[4-chloro-3-(4-hydroxy-3-nitro-benzyl)-phenyl]-4-oxa-spiro[2.5]oct-6-yl ester, Acetic acid (5S,6S,7R,8S)-6,7-diacetoxy-5-[4-chloro-3-(3-oxo-3,4-dihydro-2H-benzo[1,4]oxazin-6-ylmethyl)-phenyl]-4-oxa-spiro[2.5]oct-8-yl ester, Acetic acid (5S,6S,7R,8S)-6,7-diacetoxy-5-[4-chloro-3-(3,4-dihydro-2H-benzo[1,4]oxazin-6-ylmethyl)-phenyl]-4-oxa-spiro[2.5]oct-8-yl ester, and (5S,6R,7R,8S)-5-[4-chloro-3-(3,4-dihydro-2H-benzo[1,4]oxazin-6-ylmethyl)-phenyl]-4-oxa-spiro[2.5]octane-6,7,8-triol, or a pharmaceutically accept salt thereof.

12. The compound of claim 1 represented by Formula (I-i):

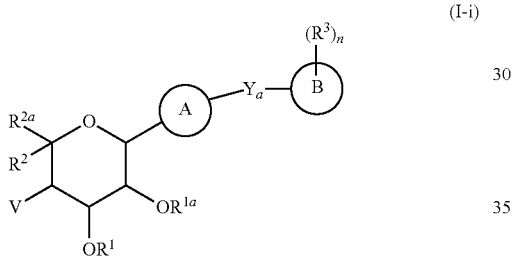

Ring A is an $C_{6-10}$aryl or a 5- to 10-membered heteroaryl; wherein the aryl or heteroaryl is optionally substituted with one or more substituents independently selected from the group consisting of a halo, hydroxy, cyano, $C_{1-6}$alkyl, $C_{3-7}$cycloalkyl, $C_{2-6}$alkenyl, $C_{2-6}$alkynyl, $C_{1-6}$alkoxy, halo$C_{1-6}$alkoxy, a 5-membered heteroaryl and a 6-membered heteroaryl;

Ring B is a $C_{6-10}$aryl or a $C_{1-10}$heteroaryl;

$Y_a$ is a bond or a $C_{1-3}$alkylene;

V is hydrogen, halo or $-OR^{1b}$;

$R^1$, $R^{1a}$, and $R^{1b}$ are independently selected from hydrogen, $C_{1-6}$ alkyl, $C_{6-10}$aryl-$C_{1-4}$alkyl, $-C(O)C_{6-10}$aryl or $-C(O)C_{1-6}$alkyl;

$R^2$ and $R^{2a}$ are independently selected from the group consisting of halo, $C_{1-3}$alkyl, and $C_{1-3}$alkoxy, wherein the alkyl and the alkoxy may be optionally substituted with one or more substituents which are independently selected from hydroxy, $C_{1-3}$alkyl, and $C_{1-3}$alkoxy; or $R^2$ and $R^{2a}$ taken together with the carbon to which they are attached may form a spiro 3- to 7-membered heterocyclyl or a spiro $C_{3-7}$cycloalkyl which may be optionally substituted with one or more substituents independently selected from halo, hydroxy, oxo, $C_{1-4}$alkyl, hydroxy$C_{1-4}$ alkyl, $C_{1-4}$alkoxy, $C_{1-4}$alkoxy$C_{1-4}$alkyl, halo$C_{1-4}$alkyl, $C_{1-6}$alkanoyl, carbamoyl, N—($C_{1-4}$alkyl)-carbamoyl, and N,N-di-($C_{1-4}$alkyl)-carbamoyl; and $R^3$, for each occurrence, is independently selected from the group consisting of halo, hydroxy, cyano, nitro, oxo, $C_{1-6}$alkyl, $C_{3-7}$cycloalkyl, $C_{3-7}$cycloalkyl$C_{1-4}$alkyl, $C_{6-10}$aryl, $C_{6-10}$aryl$C_{1-4}$alkyl, $-C(O)OR^6$, $-C(O)R^6$, $-C(O)NR^4R^5$, $-NR^4R^5$, $-CH_2NR^4R^5$, $C_{1-6}$ alkoxy, $C_{3-7}$ cycloalkoxy, $-S(O)_pR^6$, $-S(O)_2NR^4R^5$, $-OS(O)_2R^6$, $-CH_2C(O)OR^6$, $-CH_2C(O)NR^4R^5$, $-NR^6C(O)NR^4R^5$, $-NR^6C(O)OR^6$, $C_{6-10}$aryloxy, $C_{2-10}$heterocyclyl, $C_{2-10}$heterocyclyl$C_{1-4}$alkyl, $C_{1-10}$heteroaryl$C_{1-4}$alkyl, $C_{1-10}$heteroaryl, $C_{1-10}$heteroaryloxy, or $C_{1-10}$heterocycloxy; wherein $R^3$ may, for each occurrence, be optionally substituted with one or more substituents which are independently selected from halo, hydroxy, $C_{1-4}$alkyl, and $C_{1-4}$alkoxy;

$R^6$, for each occurrence, is independently selected from hydrogen, $C_{1-6}$ alkyl, $C_{3-7}$ cycloalkyl, $C_{3-7}$cycloalkyl$C_{1-4}$alkyl, $C_{6-10}$aryl, $C_{1-10}$heteroaryl, and $C_{2-10}$heterocyclyl;

$R^4$ and $R^5$, for each occurrence, are independently selected from hydrogen, $C_{1-6}$ alkyl, $C_{3-7}$ cycloalkyl, $C_{3-7}$cycloalkyl$C_{1-4}$alkyl, $C_{6-10}$aryl$C_{1-4}$alkyl, $C_{6-10}$aryl, $C_{1-10}$heteroaryl, $C_{1-10}$heteroaryl$C_{1-4}$alkyl, $C_{2-10}$heterocyclyl, and $C_{2-10}$heterocyclyl$C_{1-4}$alkyl; or $R^4$ and $R^5$ taken together along with the nitrogen to which they are bound may form a monocyclic or a bicyclic heteroaryl or heterocyclyl which may be optionally substituted with one or more halo or $C_{1-4}$alkyl;

n is 0, 1, 2, 3, or 4;

or a pharmaceutically acceptable salt thereof.

13. The compound of claim 1 represented by Formula (I-ii):

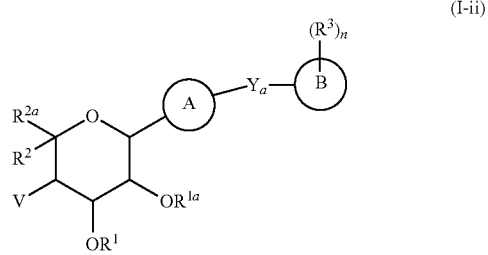

Ring A is an $C_{6-10}$aryl or a 5- to 10-membered heteroaryl; wherein the aryl or heteroaryl is optionally substituted with one or more substituents independently selected from the group consisting of a halo, hydroxy, cyano, $C_{1-6}$alkyl, $C_{3-7}$cycloalkyl, $C_{2-6}$alkenyl, $C_{2-6}$alkynyl, $C_{1-6}$alkoxy, halo$C_{1-6}$alkoxy, a 5-membered heteroaryl and a 6-membered heteroaryl;

Ring B is

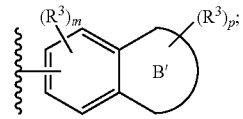

Ring B' is a 5- or 6-membered heterocycyl;

m is 0, 1, 2, 3, or 4;

p is 0, 1, 2, 3, or 4, provided that m+p is not greater than 4;

$Y_a$ is a bond or a $C_{1-3}$alkylene;

V is hydrogen, halo or $-OR^{1b}$;

$R^1$, $R^{1a}$, and $R^{1b}$ are independently selected from hydrogen, $C_{1-6}$ alkyl, $C_{6-10}$aryl-$C_{1-4}$alkyl, $-C(O)C_{6-10}$aryl or $-C(O)C_{1-6}$alkyl;

$R^2$ and $R^{2a}$ are independently selected from the group consisting of halo, $C_{1-6}$alkyl, and $C_{1-6}$alkoxy, wherein the alkyl and the alkoxy may be optionally substituted with one or more substituents which are independently selected from halo, hydroxy, $C_{1-4}$alkyl, and $C_{1-4}$alkoxy; or $R^2$ and $R^{2a}$ taken together with the carbon to which they are attached may form a spiro 4- to 6-membered heterocyclyl or a spiro $C_{3-5}$cycloalkyl which may be optionally substituted with one or more substituents independently selected from oxo, $C_{1-2}$alkyl, hydroxy$C_{1-2}$alkyl, $C_{1-2}$alkoxy$C_{1-2}$alkyl, $C_{1-3}$alkanoyl, carbamoyl, N—($C_{1-2}$alkyl)-carbamoyl, and N,N-di-($C_{1-2}$alkyl)-carbamoyl; and $R^3$, for each occurrence, is independently selected from the group consisting of halo, hydroxy, cyano, nitro, oxo, $C_{1-6}$alkyl, $C_{3-7}$cycloalkyl, $C_{3-7}$cycloalkyl$C_{1-4}$alkyl, $C_{6-10}$aryl, $C_{6-10}$aryl$C_{1-4}$alkyl, —C(O)OR$^6$, —C(O)R$^6$, —C(O)NR$^4$R$^5$, —NR$^4$R$^5$, —CH$_2$NR$^4$R$^5$, $C_{1-6}$ alkoxy, $C_{3-7}$ cycloalkoxy, —S(O)$_p$R$^6$, —S(O)$_2$NR$^4$R$^5$, —OS(O)$_2$R$^6$, —CH$_2$C(O)OR$^6$, —CH$_2$C(O)NR$^4$R$^5$, —NR$^6$C(O)NR$^4$R$^5$, —NR$^6$C(O)OR$^6$, $C_{6-10}$aryloxy, $C_{2-10}$heterocyclyl, $C_{2-10}$heterocyclyl$C_{1-4}$alkyl, $C_{1-10}$heteroaryl$C_{1-4}$alkyl, $C_{1-10}$heteroaryl, $C_{1-10}$heteroaryloxy, or $C_{1-10}$heterocycloxy; wherein $R^3$ may, for each occurrence, be optionally substituted with one or more substituents which are independently selected from halo, hydroxy, $C_{1-4}$alkyl, and $C_{1-4}$alkoxy;

$R^6$, for each occurrence, is independently selected from hydrogen, $C_{1-6}$ alkyl, $C_{3-7}$ cycloalkyl, $C_{3-7}$cycloalkyl$C_{1-4}$alkyl, $C_{6-10}$aryl, $C_{1-10}$heteroaryl, and $C_{2-10}$heterocyclyl;

$R^4$ and $R^5$, for each occurrence, are independently selected from hydrogen, $C_{1-6}$ alkyl, $C_{3-7}$ cycloalkyl, $C_{3-7}$cycloalkyl$C_{1-4}$-alkyl, $C_{6-10}$aryl$C_{1-4}$alkyl, $C_{6-10}$aryl, $C_{1-10}$heteroaryl, $C_{1-10}$heteroaryl$C_{1-4}$alkyl, $C_{2-10}$heterocyclyl, and $C_{2-10}$heterocyclyl$C_{1-4}$alkyl; or $R^4$ and $R^5$ taken together along with the nitrogen to which they are bound may form a monocyclic or a bicyclic heteroaryl or heterocyclyl which may be optionally substituted with one or more halo or $C_{1-4}$alkyl;

n is 0, 1, 2, 3, or 4;

or a pharmaceutically acceptable salt thereof.

14. The compound of claim 1 represented by Formula (I-iii):

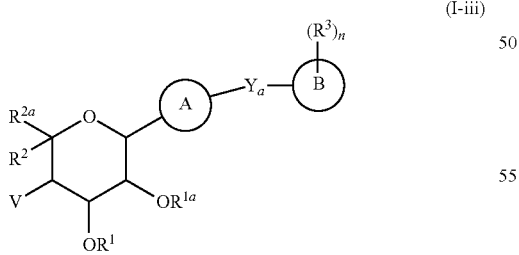

(I-iii)

Ring A is indolyl, thiophenyl, benzothiophenyl or $C_{6-10}$aryl; wherein the indolyl, thiophenyl, benzothiophenyl or $C_{6-10}$aryl may be optionally substituted with one or more substituents which are independently selected from halo, hydroxy, cyano, $C_{1-6}$alkyl, $C_{3-7}$cycloalkyl, $C_{2-6}$alkenyl, $C_{2-6}$alkynyl, $C_{1-6}$alkoxy, halo$C_{1-6}$alkoxy, a 5-membered heteroaryl and a 6-membered heteroaryl;

Ring B is

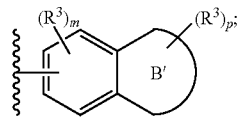

Ring B' is a 5- or 6-membered heterocycyl;
m is 0, 1, 2, 3, or 4;
p is 0, 1, 2, 3, or 4, provided that m+p is not greater than 4;
$Y_a$ is a bond or a $C_{1-3}$alkylene;
V is H, F or OH;
$R^1$ and $R^{1a}$ are both hydrogen;
$R^2$ and $R^{2a}$ are independently selected from the group consisting of halo, $C_{1-6}$alkyl, and $C_{1-6}$alkoxy, wherein the alkyl and the alkoxy may be optionally substituted with one or more substituents which are independently selected from halo, hydroxy, $C_{1-4}$alkyl, and $C_{1-4}$alkoxy; or $R^2$ and $R^{2a}$ taken together with the carbon to which they are attached may form a spiro 4- to 6-membered heterocyclyl or a spiro $C_{3-5}$cycloalkyl which may be optionally substituted with one or more substituents independently selected from oxo, $C_{1-2}$alkyl, hydroxy$C_{1-2}$alkyl, $C_{1-2}$alkoxy$C_{1-2}$alkyl, $C_{1-3}$alkanoyl, carbamoyl, N—($C_{1-2}$alkyl)-carbamoyl, and N,N-di-($C_{1-2}$alkyl)-carbamoyl; and $R^3$, for each occurrence, is independently selected from the group consisting of hydroxy, oxo, $C_{1-6}$alkyl, $C_{3-7}$cycloalkyl, $C_{6-10}$aryl, —C(O)OR$^6$, —C(O)R$^6$, $C_{1-6}$alkoxy and $C_{1-10}$heterocycloxy;

wherein $R^3$ may, for each occurrence, be optionally substituted with one or more substituents which are independently selected from halo, hydroxy, $C_{1-4}$alkyl, and $C_{1-4}$alkoxy;

$R^6$, for each occurrence, is independently selected from hydrogen, $C_{1-3}$ alkyl, $C_{3-7}$ cycloalkyl, $C_{3-7}$cycloalkyl$C_{1-3}$alkyl, $C_{6-10}$aryl, $C_{1-6}$heteroaryl, and $C_{2-6}$heterocyclyl;

n is 0, 1 or 2;

or a pharmaceutically acceptable salt thereof.

15. The compound of claim 1 represented by Formula (I-iv):

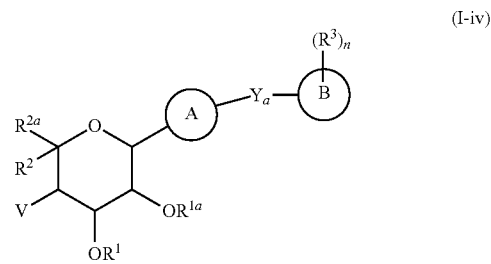

(I-iv)

Ring A is an $C_{6-10}$aryl or a 5- to 10-membered heteroaryl; wherein the aryl or heteroaryl is optionally substituted with one or more substituents independently selected from the group consisting of a halo, hydroxy, cyano, $C_{1-6}$alkyl, $C_{3-7}$cycloalkyl, $C_{2-6}$alkenyl, $C_{2-6}$alkynyl, $C_{1-6}$alkoxy, halo$C_{1-6}$alkoxy, a 5-membered heteroaryl and a 6-membered heteroaryl;

Ring B is a monocyclic $C_{6-10}$aryl or a $C_{1-10}$heteroaryl;

$Y_a$ is a bond or a $C_{1-3}$alkylene;

V is hydrogen, halo or —OR$^{1b}$;

$R^1$, $R^{1a}$, and $R^{1b}$ are independently selected from hydrogen, $C_{1-6}$ alkyl, $C_{6-10}$aryl-$C_{1-4}$alkyl, —C(O)$C_{6-10}$aryl or —C(O)$C_{1-6}$alkyl;

$R^2$ and $R^{2a}$ are independently selected from the group consisting of halo, $C_{1-6}$alkyl, and $C_{1-6}$alkoxy, wherein the alkyl and the alkoxy may be optionally substituted with one or more substituents which are independently selected from halo, hydroxy, $C_{1-4}$alkyl, and $C_{1-4}$alkoxy; or $R^2$ and $R^{2a}$ taken together with the carbon to which they are attached may form a spiro 4- to 6-membered heterocyclyl or a spiro $C_{3-5}$cycloalkyl which may be optionally substituted with one or more substituents independently selected from oxo, $C_{1-2}$alkyl, hydroxy$C_{1-2}$alkyl, $C_{1-2}$alkoxy$C_{1-2}$alkyl, $C_{1-3}$alkanoyl, carbamoyl, N—($C_{1-2}$alkyl)-carbamoyl, and N,N-di-($C_{1-2}$alkyl)-carbamoyl; and $R^3$, for each occurrence, is independently selected from the group consisting of halo, hydroxy, cyano, nitro, oxo, $C_{1-6}$alkyl, $C_{3-7}$cycloalkyl, $C_{3-7}$cycloalkyl$C_{1-4}$alkyl, $C_{6-10}$aryl, $C_{6-10}$aryl$C_{1-4}$alkyl, —C(O)OR$^6$, —C(O)R$^6$, —C(O)NR$^4$R$^5$, —NR$^4$R$^5$, —CH$_2$NR$^4$R$^5$, $C_{1-6}$ alkoxy, $C_{3-7}$ cycloalkoxy, —S(O)$_p$R$^6$, —S(O)$_2$NR$^4$R$^5$, —OS(O)$_2$R$^6$, —CH$_2$C(O)OR$^6$, —CH$_2$C(O)NR$^4$R$^5$, —NR$^6$C(O)NR$^4$R$^5$, —NR$^6$C(O)OR$^6$, $C_{6-10}$aryloxy, $C_{2-10}$heterocyclyl, $C_{2-10}$heterocyclyl$C_{1-4}$alkyl, $C_{1-10}$heteroaryl$C_{1-4}$alkyl, $C_{1-10}$heteroaryl, $C_{1-10}$heteroaryloxy, or $C_{1-10}$heterocycloxy; wherein $R^3$ may, for each occurrence, be optionally substituted with one or more substituents which are independently selected from halo, hydroxy, $C_{1-4}$alkyl, and $C_{1-4}$alkoxy;

$R^6$, for each occurrence, is independently selected from hydrogen, $C_{1-6}$ alkyl, $C_{3-7}$ cycloalkyl, $C_{3-7}$cycloalkyl$C_{1-4}$alkyl, $C_{6-10}$aryl, $C_{1-10}$heteroaryl, and $C_{2-10}$heterocyclyl;

$R^4$ and $R^5$, for each occurrence, are independently selected from hydrogen, $C_{1-6}$ alkyl, $C_{3-7}$ cycloalkyl, $C_{3-7}$cycloalkyl$C_{1-4}$alkyl, $C_{6-10}$aryl$C_{1-4}$alkyl, $C_{6-10}$aryl, $C_{1-10}$heteroaryl, $C_{1-10}$heteroaryl$C_{1-4}$alkyl, $C_{2-10}$heterocyclyl, and $C_{2-10}$heterocyclyl$C_{1-4}$alkyl; or $R^4$ and $R^5$ taken together along with the nitrogen to which they are bound may form a monocyclic or a bicyclic heteroaryl or heterocyclyl which may be optionally substituted with one or more halo or $C_{1-4}$alkyl;

n is 0, 1, 2, 3, or 4;

or a pharmaceutically acceptable salt thereof.

16. The compound of claim 1 represented by Formula (I-v):

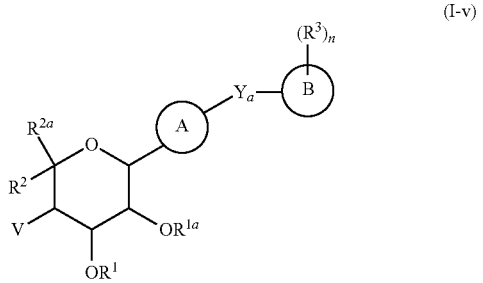

(I-v)

Ring A is indolyl, thiophenyl, benzothiophenyl or $C_{6-10}$aryl; wherein the indolyl, thiophenyl, benzothiophenyl or $C_{6-10}$aryl may be optionally substituted with one or more substituents which are independently selected from halo, hydroxy, cyano, $C_{1-6}$alkyl, $C_{3-7}$cycloalkyl, $C_{2-6}$alkenyl, $C_{2-6}$alkynyl, $C_{1-6}$alkoxy, halo$C_{1-6}$alkoxy, a 5-membered heteroaryl and a 6-membered heteroaryl;

Ring B is a monocyclic $C_{6-10}$aryl or a $C_{1-10}$heteroaryl;

$Y_a$ is a bond or a $C_{1-3}$alkylene;

V is H, F or OH;

$R^1$ and $R^{1a}$ are both hydrogen;

$R^2$ and $R^{2a}$ are independently selected from the group consisting of halo, $C_{1-6}$alkyl, and $C_{1-6}$alkoxy, wherein the alkyl and the alkoxy may be optionally substituted with one or more substituents which are independently selected from halo, hydroxy, $C_{1-4}$alkyl, and $C_{1-4}$alkoxy; or $R^2$ and $R^{2a}$ taken together with the carbon to which they are attached may form a spiro 4- to 6-membered heterocyclyl or a spiro $C_{3-5}$cycloalkyl which may be optionally substituted with one or more substituents independently selected from oxo, $C_{1-2}$alkyl, hydroxy$C_{1-2}$alkyl, $C_{1-2}$alkoxy$C_{1-2}$alkyl, $C_{1-3}$alkanoyl, carbamoyl, N—($C_{1-2}$alkyl)-carbamoyl, and N,N-di-($C_{1-2}$alkyl)-carbamoyl; and $R^3$, for each occurrence, is independently selected from the group consisting of hydroxy, oxo, $C_{1-6}$alkyl, $C_{3-7}$cycloalkyl, $C_{6-10}$aryl, —C(O)OR$^6$, —C(O)R$^6$, $C_{1-6}$alkoxy and $C_{1-10}$heterocycloxy;

wherein $R^3$ may, for each occurrence, be optionally substituted with one or more substituents which are independently selected from halo, hydroxy, $C_{1-4}$alkyl, and $C_{1-4}$alkoxy;

$R^6$, for each occurrence, is independently selected from hydrogen, $C_{1-3}$ alkyl, $C_{3-7}$ cycloalkyl, $C_{3-7}$cycloalkyl$C_{1-3}$alkyl, $C_{6-10}$aryl, $C_{1-6}$heteroaryl, and $C_{2-6}$heterocyclyl;

n is 0, 1 or 2;

or a pharmaceutically acceptable salt thereof.

17. A pharmaceutical composition comprising a compound according to claim 1, or a pharmaceutically acceptable salt thereof, and a pharmaceutically acceptable excipient.

18. A method of treating diabetes comprising administering a compound according to claim 1, or a pharmaceutically acceptable salt thereof, to a subject in need thereof.

* * * * *